US010280463B2

(12) United States Patent
Walker et al.

(10) Patent No.: US 10,280,463 B2
(45) Date of Patent: May 7, 2019

(54) IDENTIFICATION OF UNIQUE GENE EXPRESSION PROFILES IN CHILDREN WITH REGRESSIVE AUTISM SPECTRUM DISORDER (ASD) AND ILEOCOLITIS

(71) Applicants: WAKE FOREST UNIVERSITY HEALTH SCIENCES, Winston-Salem, NC (US); Arthur Krigsman, Far Rockaway, NY (US)

(72) Inventors: Stephen Walker, Winston-Salem, NC (US); Arthur Krigsman, Far Rockaway, NY (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 53 days.

(21) Appl. No.: 14/765,527

(22) PCT Filed: Feb. 6, 2014

(86) PCT No.: PCT/US2014/015144
§ 371 (c)(1),
(2) Date: Aug. 3, 2015

(87) PCT Pub. No.: WO2014/124166
PCT Pub. Date: Aug. 14, 2014

(65) Prior Publication Data
US 2015/0361499 A1    Dec. 17, 2015

Related U.S. Application Data

(60) Provisional application No. 61/761,510, filed on Feb. 6, 2013.

(51) Int. Cl.
*C12Q 1/68*     (2018.01)
*C12Q 1/6883*   (2018.01)
*G01N 33/68*    (2006.01)
*A61K 31/56*    (2006.01)
*A61K 31/606*   (2006.01)
*A61K 38/43*    (2006.01)

(52) U.S. Cl.
CPC ............ *C12Q 1/6883* (2013.01); *A61K 31/56* (2013.01); *A61K 31/606* (2013.01); *A61K 38/43* (2013.01); *G01N 33/6893* (2013.01); *G01N 33/6896* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

2005/0084880 A1* 4/2005 Duman ................ C12Q 1/6883
435/6.16

FOREIGN PATENT DOCUMENTS

WO  WO 2011/127219  10/2011
WO  WO 2012/174282  12/2012

OTHER PUBLICATIONS

NCBI dbSNP, rs1127155, ss76107542 (National Center for Biotechnology Information, National Library of Medicine, Bethesda, MD, USA). Aug. 28, 2007.*
Kuwano et al PLoS One. 2011. 6(9): e24723.*
Liu et al (Clinical Immunology. 2004. 112: 225-230.*
Coleman, R. Drug Discovery Today. 2003. 8: 233-235.*
Hanke et al. Clinical Chemistry. 2007. 53: 2070-2077.*
Palmer et al. BMC Genomics. 2006. 7:115.*
Min et al BMC Genomics. 2010. 11:96.*
Haynes et al Electrophoresis. 1998. 19: 1862-1871.*
Gokmen-Polar Cancer Research. 2001. 61: 1375-1381.*
Klopocki et al Annual Reviews Genomics Human Genetics. 2011. 12: 53-72.*
Al-Mulla J Clin Pathol. 2003. 56: 210-217.*
Sutherland et al. Acta Oncologica. 1995. 34: 651-656.*
Walker et al., PLosOne. Mar. 8, 2013. 8(3): e58058).*
Kirman et al Digestive Diseases and Sciences. Feb. 1995. 40(2): 291-295.*
Adams et al., "Gastrointestinal flora and gastrointestinal status in children with autism-comparisons to typical children and correlation with autism severity." *BMC Gastroenterol* 11:22. (2011).
Ashwood and Wakefield AJ. "Immune activation of peripheral blood and mucosal CD3+ lymphocyte cytokine profiles in children with autism and gastrointestinal symptoms." J Neuroimmunol 173: 126-134; (2006).
Ashwood et al. "Spontaneous mucosal lymphocyte cytokine profiles in children with autism and gastrointestinal symptoms: mucosal immune activation and reduced counter regulatory interleukin-10." J Clin Immunol 24: 664-673 (2004).
Balzola et al. "Panenteric IBD-like disease in a patient with regressive autism shown for the first time by the wireless capsule enteroscopy: another piece in the jigsaw of this gut-brain syndrome?" (2005) Am J Gastroenterol 100: 979-981.
Bauman "Medical comorbidities in autism: challenges to diagnosis and treatment." (2010) Neurotherapeutics 7(3): 320-327.
Black et al. "Relation of childhood gastrointestinal disorders to autism: nested case-control study using data from the UK General Practice Research Database." (2002) BMJ 325(24): 419-421.
Buie et al., (2010) "Evaluation, diagnosis, and treatment of gastrointestinal disorders in individuals with ASDs: a consensus report," *Pediatrics* 125 Suppl 1:S1-18.
Costello et al. "Dissection of the inflammatory bowel disease transcriptome using genome-wide cDNA microarrays." (2005) PLoS Med 2(8): e199.

(Continued)

*Primary Examiner* — Carla J Myers
(74) *Attorney, Agent, or Firm* — Saul Ewing Arnstein & Lehr LLP; Kathryn Doyle

(57) ABSTRACT

The invention provides compositions and methods for identifying autism and autism spectrum disorders in humans. The invention also includes compositions and methods for identifying unique gene expression profiles in children with regressive autism spectrum disorder (ASD) and ileocolitis.

2 Claims, 4 Drawing Sheets
Specification includes a Sequence Listing.

(56) References Cited

OTHER PUBLICATIONS

D'Eufemia et al. "Abnormal intestinal permeability in children with autism." (1996) Acta Paediatr 85: 1076-1079.
De Magistris et al. "Alterations of the intestinal barrier in patients with autism spectrum disorders and in their first-degree relatives." (2010) J Pediatr Gastroenterol Nutr 51: 418-424.
Finegold et al. "Gastrointestinal microflora studies in late-onset autism." (2002) Clin Infect Dis 35(Suppl 1): S6-S16.
Furlano et al. "Colonic CD8 and gamma delta T-cell infiltration with epithelial damage in children with autism." (2001) J Pediatr 138(3):366-372.
Galamb et al. "mRNA expression, functional profiling and multivariate classification of colon biopsy specimen by cDNA overall glass microarray." (2006) World J Gastroenterol 12(43): 6998-7006.
Galiatsatos et al. "Autistic enterocolitis: fact or fiction?" (2009) Can J Gastroenterol 23: 95-98.
Genuis et al., "Celiac Disease Presenting as Autism." *J. of Child Neurology* 25(1):114-119. (2010).
Gonzalez et al., "Caracteristicas Endoscópicas, Histológicas E Inmunológicas de la Mucosa Digestiva en niños Autistas Con Síntomas Gastrointestinales." (2005) Arch Venez Pueric Pediat 69: 19-25.
Horvath and Perman "Autistic disorder and gastrointestinal disease." (2002) Current Opinion in Pediatr 14: 583-587.
Horvath et al. "Gastrointestinal abnormalities in children with autistic disorder." (1999) J Pediatr 135: 559-563.
Jarocka-Cyrta et al. "Eosinophilic esophagitis as a cause of feeding problems in autistic boy. The first reported case." (2011) J Autism Dev Disord 41(3): 372-374.
Jyonouchi et al. "Proinflammatory and regulatory cytokine production associated with innate and adaptive immune responses in children with autism spectrum disorders and developmental regression." (2001) J Neuroimmunol 120(1-2): 170-179.
Jyonouchi et al. "Dysregulated innate immune responses in young children with autism spectrum disorders: their relationship to gastrointestinal symptoms and dietary intervention." (2005) Neuropsychobiology 51(2): 77-85.

Krigsman et al. Clinical Presentation and Histologic Findings at Ileocolonoscopy in Children with Autistic Spectrum Disorder and Chronic Gastrointestinal Symptoms (2010) Autism Insights 1: 1-11.
Lawrance et al. "Ulcerative colitis and Crohn's disease: distinctive gene expression profiles and novel susceptibility candidate genes." (2001) Hum Mol Genet 10(5): 445-456.
Levy "Relationship of dietary intake to gastrointestinal symptoms in children with autistic spectrum disorders." (2007) Biol Psychiatry 61: 492-497.
Merla et al. "Copy number variants at Williams-Beuren syndrome 7q11.23 region." (2010 Hum Genet 128:3-26.
Ming et al. "Autism spectrum disorders: concurrent clinical disorders." (2008) J Child Neurol 23: 6-13.
NCBI Accession No. NM_000417—published Nov. 28, 2009.
NCBI Accession No. NM_006546—published Dec. 3, 2004.
NCBI Accession No. NM_016639—published May 9, 2008.
Torrente et al. "Small intestinal enteropathy with epithelial IgG and complement deposition in children with regressive autism." (2002) Mol Psychiatry 7: 375-382.
Torrente et al. "Focal-enhanced gastritis in regressive autism with features distinct from Crohn's and Helicobacter pylori gastritis." (2004) Am J Gastroenterol 4: 598-605.
Valicenti-McDermott et al., "Frequency of gastrointestinal symptoms in children with autistic spectrum disorders and association with family history of autoimmune disease." (2006) J Dev Behav Pediatr 27(2 Suppl): S128-136.
Vargas et al., "Neuroglial activation and neuroinflammation in the brain of patients with autism." (2005) Ann Neurol 57(1): 67-81. Erratum in: Ann Neurol. 2005;57(2): 304.
Von Stein et al., "Multigene analysis can discriminate between ulcerative colitis, Crohn's disease, and irritable bowel syndrome." *Gastroentorology* 134(7):1869-1881. (2008).
Williams et al., "Impaired carbohydrate digestion and transport and mucosal dysbiosis in the intestines of children with autism and gastrointestinal disturbances." (2011) PLoS One 6(9): e24585.
Wright, "Using the new UK-WHOHO growth charts." BMJ 2010;340:c1140 (2010).
Wu et al., "Genome-wide Gene Expression Differences in Crohn's Disease and Ulcerative Colitis from Endoscopic Pinch Biopsies: Insights into Distinctive Pathogenesis." (2007) Inflamm Bowel Dis 13(7): 807-821.

\* cited by examiner

IDENTIFICATION OF UNIQUE GENE EXPRESSION PROFILES IN CHILDREN WITH REGRESSIVE AUTISM SPECTRUM DISORDER (ASD) AND ILEOCOLITIS

CROSS-REFERENCE TO RELATED APPLICATIONS

This application is the U.S. national phase application filed under 35 U.S.C. § 371 claiming priority to International Patent Application No. PCT/US2014/015144, filed Feb. 6, 2014, which claims priority under 35 U.S.C. § 119(e) to U.S. Provisional Application No. 61/761,510, filed Feb. 6, 2013, all of which applications are hereby incorporated by reference in their entireties.

BACKGROUND OF THE INVENTION

Gastrointestinal (GI) symptoms are common in children with autism spectrum disorders (ASD). Recent studies report an increased frequency of GI symptoms in ASD children compared with typically developing children and those with other developmental delays (Valicenti-McDermott et al. (2006) J Dev Behav Pediatr 27(2 Suppl): S128-136; Ming et al. (2008) J Child Neurol 23: 6-13; Buie et al. (2010) Pediatrics 125 Suppl 1: S1-18; Bauman (2010) Neurotherapeutics 7(3): 320-327). Prospective, controlled studies suggest that as many as 70% of autistic children exhibit chronic GI-related symptoms (Valicenti-McDermott et al. (2006) J Dev Behav Pediatr 27(2 Suppl): S128-136; Horvath and Perman (2002) Current Opinion in Ped 14: 583-587; Levy (2007) Biol Psychiatry 61: 492-497) including diarrhea, laxative-dependent constipation, abdominal distension, failure to thrive, weight loss, feeding problems, and abdominal pain related to extreme irritability, aggression, and self-injury. These symptoms can be minimized or disappear following treatment of the underlying GI disorder (Jarocka-Cyrta et al. (2011) J Autism Dev Disord 41(3): 372-374). Retrospective chart review studies have shown no increase in GI symptoms in ASD children compared to neurotypical children (Black et al. (2002) BMJ 325(24): 419-421).

Gastrointestinal symptoms in children with autism spectrum disorder (ASD) are often associated with mucosal inflammatory infiltrates of the small and large intestine. Although distinct histologic and immunohistochemical properties of this inflammatory infiltrate have been previously described in this $ASD^{IC}$ group, molecular characterization of these lesions has not been reported. In ASD children with GI symptoms who undergo endoscopic and histologic examinations, inflammatory pathology is reported with high frequency (Horvath et al. (1999) J Pediatr 135: 559-563; Ashwood et al. (2004) J Clin Immunol 24: 664-673; Gonzalez et al. (2005) Arch Venez Pueric Pediat 69: 19-25; Krigsman et al. (2010) Autism Insights 1: 1-11). Features of the GI disease reported originally—ileocolonic lymphoid nodular hyperplasia (LNH) and ileocolitis—have since been expanded to include esophagitis (Horvath et al. (1999) J Pediatr 135: 559-563), atypical focal gastritis (Torrente et al. (2004) Am J Gastroenterol 4: 598-605), and enteritis (Torrente et al. (2004) Am J Gastroenterol 4: 598-60514; Torrente et al. (2002) Mol Psychiatry 7: 375-382; Balzola et al. (2005) Am J Gastroenterol 100: 979-981). Further analyses of the inflammatory infiltrate in the mucosa and the associated mucosal cytokine profiles have not only confirmed the presence of disease, but suggest characteristic features that distinguish the lesions in ASD children from the more well-described inflammatory bowel diseases (IBDs), i.e. Crohn's disease and ulcerative colitis (Ashwood et al. (2004) J Clin Immunol 24: 664-673; Torrente et al. (2004) Am J Gastroenterol 4: 598-605; Torrente et al. (2002) Mol Psychiatry 7: 375-382; Furlano et al. (2001) J Pediatr 38: 366-372). In parallel, disturbances in mucosal function (D'Eufemia et al. (1996) Acta Paediatr 85: 1076-1079; De Magistris et al. (2010) J Pediatr Gastroenterol Nutr 51: 418-424) and intestinal microflora (Finegold et al. (2002) Clin Infect Dis 35(Suppl 1): S6-S16; Williams et al. (2011) PLoS One 6(9): e24585) have been reported and may contribute to the GI pathology in ASD. A recent consensus report regarding GI disorders in individuals with ASDs concluded that ASD children with classic gastrointestinal symptoms often have a chronic inflammatory process "characterized by nodular lymphoid hyperplasia (NLH), enterocolitis, and mucosal infiltration by immune cells along the length of the gastrointestinal tract" (Buie et al. (2010) Pediatrics 125 Suppl 1: S1-18). While the clinical significance of these findings is still under investigation, it appears that the immunologic and inflammatory activity in the bowel may be part of a larger, systemic multi-organ immunopathology (Jyonouchi et al. (2001) J Neuroimmunol 120(1-2): 170-179; Jyonouchi et al. (2005) Neuropsychobiology 51(2): 77-85; Vargas et al. (2005) Ann Neurol 57(1): 67-81. Erratum in: Ann Neurol. 2005; 57(2): 304).

Currently, it is not clear whether the mucosal inflammatory changes seen in $ASD^{IC}$ children represent a milder variant of inflammatory bowel disease or whether a novel pathogenic process is underway. It is possible that a thorough molecular characterization of inflamed gastrointestinal tissue from ASD children and children with established IBD will help to answer this question. Several studies have described the use of gene expression profiling of biopsy-derived gastrointestinal tissue to provide molecular signatures for, and to distinguish between, Crohn's disease and ulcerative colitis (e.g., Wu et al. (2007) Inflamm Bowel Dis 13(7): 807-821; Galamb et al. (2006) World J Gastroenterol 12(43): 6998-7006; Costello et al. (2005) PLoS Med 2(8): e199; Lawrance et al. (2001) Hum Mol Genet 10(5): 445-456). Using this approach, one group identified a biomarker panel that could be used to distinguish IBD (Crohn's disease (CD) and ulcerative colitis (UC)) from "non-IBD" (in this case irritable bowel syndrome; IBS). The study further identified a subset of transcripts, consisting of seven genes, whose differential expression was useful in distinguishing the IBD subtypes, Crohn's disease and ulcerative colitis, with a high degree of sensitivity and specificity (von Stein et al. (2008) Gastroenterology 134(7): 1869-1881). Gene expression analysis has been recently utilized in the investigation of gastrointestinal dysfunction in ASD children. Building upon prior findings of mucosal brush border enzyme deficiencies in GI symptomatic ASD children, transcript levels of ileal disaccharidases were measured and found to be deficient in those patients (Williams et al. (2011) PLoS One 6(9): e24585. Epub 2011 Sep. 16). Using pyrosequencing analysis of mucoepithelial bacteria, a significant multi-component dysbiosis in the same ASD cohort was also reported.

Despite the published evidence (Horvath et al. (1999) J Pediatr 135: 559-563: Ashwood et al. (2004) J Clin Immunol 24: 664-673: Gonzalez et al. (2005) Arch Venez Pueric Pediat 69: 19-25: Krigsman et al. (2010) Autism Insights 1: 1-11: Torrente et al. (2004) Am J Gastroenterol 4: 598-605: Torrente et al. (2002) Mol Psychiatry 7: 375-382: Furlano et al. (2001) J Pediatr 38: 366-372), the debate still continues (Buie et al. (2010) Pediatrics 125 Suppl 1: S1-18; Galiatsatos et al. (2009) Can J Gastroenterol 23: 95-98: Wright (2010) BMJ 340: c1807) as to whether children with ASD and GI symptoms and non-specific mucosal infiltrates have conventionally recognized forms of IBD, a novel IBD phenotype, or no disease at all.

Detailed molecular information, generated from clinical specimens derived from ASD$^{IC}$ children, has the potential to provide valuable clarification of some of these issues. At a minimum, the analysis of differential gene expression in relevant tissue from this group of affected children will lead to a better understanding of the molecular processes involved in their inflammatory disease, including pathways that have been significantly impacted. This in turn may provide a more detailed understanding of the biology that underlies this condition.

Therefore, there is a need in the art for a molecular characterization of children with ASD and GI symptoms and for methods of diagnosing ASD, and GI disorders in children with ASD. The present invention satisfies this unmet need.

SUMMARY OF THE INVENTION

In one aspect, the invention provides a method of diagnosing a gastrointestinal disorder in a subject, involving measuring the levels of one or more biomarkers provided in Tables 6, 9, and 10 (e.g., IL2RA, IGF2BP1, and TNFRSF12A) in a biological sample from the subject, where an alteration in the level of the one or more biomarkers relative to a reference indicates that the subject has a gastrointestinal disorder.

In another aspect, the invention provides a method of diagnosing a gastrointestinal disorder in a subject, involving detecting one or more rs1127155 and rs6460055 polymorphisms in a biological sample from the subject, where the presence of one or more rs1127155 and rs6460055 polymorphisms indicates that the subject has or is at risk of having a gastronintestinal disorder. In a related aspect the method, further involves measuring the levels of biomarker NM_152559.

In still another aspect, the invention provides a method of diagnosing autism spectrum disorder (ASD) in a subject, involving measuring the levels of one or more biomarkers in Tables 6, 9, and 10 (e.g., IL2RA, IGF2BP1, and TNFRSF12A) in a biological sample from the subject, where an alteration in the level of the one or more biomarkers relative to a reference indicates that the subject has autism spectrum disorder.

In yet another aspect, the invention provides a method of diagnosing autism spectrum disorder (ASD) in a subject, involving detecting one or more rs1127155 and rs6460055 polymorphisms in a biological sample from the subject, where the presence of one or more rs1127155 and rs6460055 polymorphisms indicates that the subject has or is at risk of having autism spectrum disorder.

In an additional aspect, the invention provides a kit for the diagnosis of a gastrointestinal and/or autism spectrum disorder, the kit containing at least one agent capable of specifically binding or hybridizing to a polypeptide or nucleic acid molecule of a biomarker in Tables 6, 9, or 10 (e.g., IL2RA, IGF2BP1, and TNFRSF12A, and directions for using the agent for the diagnosis of a gastrointestinal and/or autism spectrum disorder.

In still another aspect, the invention provides a kit for the diagnosis of a gastrointestinal and/or autism spectrum disorder, the kit containing at least one agent capable of specifically binding or hybridizing to polymorphism rs1127155 or rs6460055, and directions for using the agent for the diagnosis of a gastrointestinal and/or autism spectrum disorder.

In various embodiments of any of the aspects delineated herein, the subject is a child (i.e., a human from newborn to age 21). In additional embodiments, the subject has an autism spectrum disorder (e.g., autism). In various embodiments, the gastrointestinal disorder is ileocolitis, ileitis, colitis, enteritis, duodenitis, gastritis, and/or esophagitis.

In various embodiments of any of the aspects delineated herein, the method involves measuring the levels of biomarker NM_152559. In various embodiments of any of the aspects delineated herein, the method involves measuring the levels of a biomarker selected from IL2RA, IGF2BP1 and TNFRSF12A or a biomarker in Tables 6, 9, and 10. In various embodiments, the biological sample is from the colon, ileum, small bowel, stomach, and/or esophagus. In various embodiments of any of the aspects delineated herein, measuring comprises PCR assays or microarrays.

In various embodiments of any of the aspects delineated herein, the method involves using the results obtained from the diagnostic assay to selecting or administering a treatment. In various embodiments, the treatment involves administering corticosteroids, immunomodulators, 5-aminosalicylic acid preparations, cytokine specific antagonists, dietary restrictions, antimicrobials, probiotics, and/or supplemental digestive enzymes.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 3A. There were 1409 unique DETs (differentially-expressed transcripts) in the ASD$^{IC}$ versus control comparison in TI mucosa. FIG. 3B. There were 1189 unique DETs in the ASD$^{IC}$ versus control comparison in colonic mucosa. FIG. 3C. The overlap between those two lists is displayed in this Venn diagram. There are a total of 178 DETs shared in ASD$^{IC}$ tissues (Table 9). This list of 178 DETs was imported into Ingenuity Pathway Analysis software for further analysis.

Figure 1:
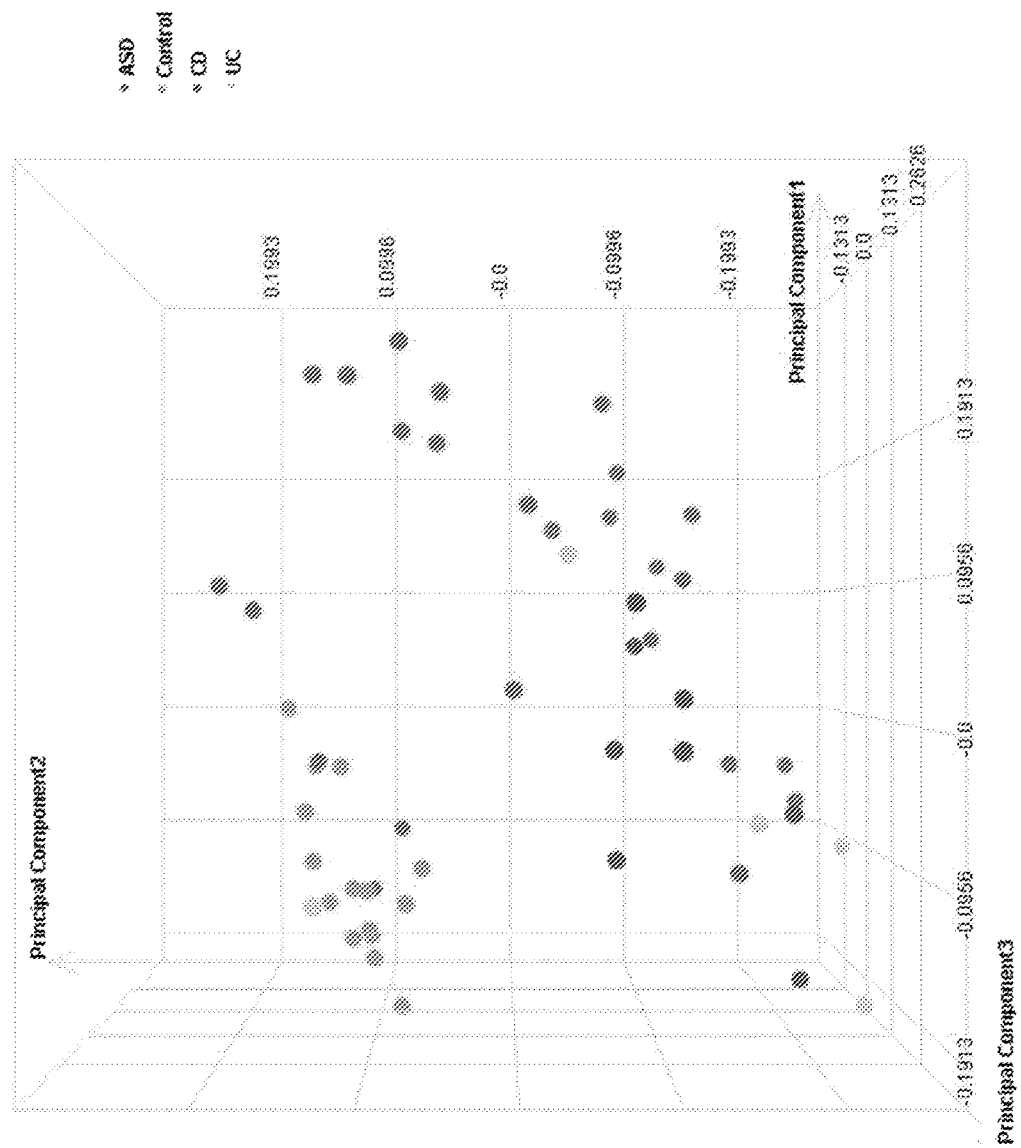
FIG. 1 is an image depicting a Principal Component Analysis (PCA) scatterplot representing 53 individual microarray datasets from terminal ileum tissues. Each circle represents the cumulative gene expression profile for an individual sample. Samples with similar profiles cluster together in the three-dimensional space.

In this dendogram, related groups are indicated by the length of the horizontal line (shorter=more related), joined by the vertical lines (e.g. in the colon: UC and Crohn's samples are most similar to each other, followed by ASDGI, and then the control group. This pattern is identical in the terminal ileum sample groups).

DETAILED DESCRIPTION

The present invention relates generally to diagnostic methods and markers, prognostic methods and markers, and therapy evaluators for autism. In one embodiment, the markers of the invention make up a gene expression profile unique to children (i.e., newborn to age 21) with autism spectrum disorder (ASD) who have comorbid gastrointestinal inflammation (referred herein as "$ASD^{IC}$").

In one embodiment, the present invention relates to biomarkers of $ASD^{IC}$, methods for diagnosis of $ASD^{IC}$, methods of determining predisposition to $ASD^{IC}$, methods of monitoring progression/regression of $ASD^{IC}$, methods of assessing efficacy of compositions for treating $ASD^{IC}$, methods of screening compositions for activity in modulating biomarkers of $ASD^{IC}$, methods of treating $ASD^{IC}$, as well as other methods based on biomarkers of $ASD^{IC}$.

In one embodiment, the markers of the invention are useful for discriminating between different inflammatory disorders including but is not limited to Crohn's disease, ulcerative colitis, inflammatory bowel disease (IBD), and $ASD^{IC}$.

In one embodiment, the markers of the invention diagnose ASD-associated IBD variant, or, alternatively, a prodromal phase of typical inflammatory bowel disease.

In one embodiment, the present invention relates to biomarkers of ASD-associated IBD variant, methods for diagnosis of ASD-associated IBD variant, methods of determining predisposition to ASD-associated IBD variant, methods of monitoring progression/regression of ASD-associated IBD variant, methods of assessing efficacy of compositions for treating ASD-associated IBD variant, methods of screening compositions for activity in modulating biomarkers of ASD-associated IBD variant, methods of treating ASD-associated IBD variant, as well as other methods based on biomarkers of ASD-associated IBD variant.

The invention also provides a method for permitting refinement of disease diagnosis, disease risk prediction, and clinical management of patients associated with ASD-associated inflammatory disease. That is, the biomarkers of the invention can be used as a marker for the disease state or disease risk. For example, the presence of the selective biomarkers of the invention permits refinement of disease diagnosis, disease risk prediction, and clinical management of patients being treated with agents that are associated with a particular ASD-associated inflammatory disease.

The invention also provides a method of diagnosing, treating, and monitoring autism, even without accompanying inflammatory bowel disease.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element. "About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

By "alteration" is meant an increase or decrease. An alteration may be by as little as 1%, 2%, 3%, 4%, 5%, 10%, 20%, 30%, or by 40%, 50%, 60%, or even by as much as 75%, 80%, 90%, or 100%.

"Amplification" refers to any means by which a polynucleotide sequence is copied and thus expanded into a larger number of polynucleotide sequences, e.g., by reverse transcription, polymerase chain reaction or ligase chain reaction, among others.

An "analyte", as used herein refers to any substance or chemical constituent that is undergoing analysis. For example, an "analyte" can refer to any atom and/or molecule; including their complexes and fragment ions. The term may refer to a single component or a set of components. In the case of biological molecules/macromolecules, such analytes include but are not limited to: polypeptides, polynucleotides, proteins, peptides, antibodies, DNA, RNA, carbohydrates, steroids, and lipids, and any detectable moiety thereof, e.g. immunologically detectable fragments. In some instances, an analyte can be a biomarker.

The term "assessing" includes any form of measurement, and includes determining if an element is present or not. The terms "determining," "measuring," "evaluating," "assessing," and "assaying" are used interchangeably and include quantitative and qualitative determinations. Assessing may be relative or absolute. "Assessing the presence of" includes determining the amount of something present, and/or determining whether it is present or absent.

The term "autism spectrum disorder (ASD)" refers to a group of developmental brain disorders, having a wide range of symptoms characterized by social deficits and communication difficulties, stereotyped or repetitive behaviors and interests, and in some cases, cognitive delays. ASD is typically diagnosed according to guidelines listed in the American Psychiatric Association's *Diagnostic and Statistical Manual of Mental Disorders 5th edition* (DSM-5). ASDs include autism and Asperger syndrome. To various degrees, the psychiatric diagnosis of ASDs is subjective in nature as it based solely on observed behaviors and not on any quantifiable biologic, physiologic, immunologic, histologic processes or organ imaging technique.

The term "biomarker" is a characteristic that is objectively measured and evaluated as an indicator of normal biological processes, pathological processes, or pharmacological responses to a therapeutic intervention. The biomarker can for example describe a substance whose detection indicates a particular disease state. The biomarker may be a peptide that causes disease or is associated with susceptibility to disease. In some instances, the biomarker may be a gene that causes disease or is associated with susceptibility to disease. In other instances, the biomarker is a metabolite. In any event, the biomarker can be differentially present (i.e., increased or decreased) in a biological sample from a subject or a group of subjects having a first phenotype (e.g., having a disease) as compared to a biological sample from a subject or group of subjects having a second phenotype (e.g., not having the disease). A biomarker is preferably differentially present at a level that is statistically significant (i.e., a p-value less than 0.05 and/or a q-value of less than 0.10 as determined using either Welch's T-test or Wilcoxon's rank-sum Test).

By "capture reagent" is meant a reagent that specifically binds a nucleic acid molecule or polypeptide to select or isolate the nucleic acid molecule or polypeptide.

By "decreases" is meant a negative alteration of at least 10%, 25%, 50%, 75%, 100%, 200%, 300%, 400%, 500%, 1000%, or more.

By "detect" refers to identifying the presence, absence, level, or concentration of an agent.

By "detectable" is meant a moiety that when linked to a molecule of interest renders the latter detectable. Such detection may be via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health. Preferably, the animal is a mammal. More preferably, the mammal is a human.

A disease or disorder is "alleviated" if the severity of a sign or symptom of the disease or disorder, the frequency with which such a sign or symptom is experienced by a patient, or both, is reduced.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "expression" as used herein is defined as the transcription and/or translation of a particular nucleotide sequence driven by its promoter.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "genotype" is meant the genetic composition of a cell, organism, or individual. By "IGF2BP1 nucleic acid molecule" is meant a polynucleotide encoding an IGF2BP1 polypeptide (e.g., NP_006537). An exemplary IGF2BP1 nucleic acid molecule is provided at NCBI Accession No. NM_006546. An exemplary IGF2BP1 mRNA transcript is provided below (SEQ ID NO: 1):

```
  1 atttagaggc ggcgccaggg cggccgcgga gaaacgtgac acaccagccc tctcggaggg
 61 gtttcggacc gaagggaaga agctgcgccg tgtcgtccgt ctccctgcgc gccgcgggca
121 cttctcctgg gctctccccg aactctcccg cgacctctgc gcgccctcag gccgccttcc
181 ccgccctggg ctcgggacaa cttctggggt ggggtgcaaa gaaagtttgc ggctcctgcc
241 gccggcctct ccgcctcttg gcctaggagg ctcgccgccc gcgcccgctc gttcggcctt
301 gcccgggacc gcgtcctgcc ccgagaccgc caccatgaac aagctttaca tcggcaacct
361 caacgagagc gtgaccccca cggacttgga gaaagtgttt gcggagcaca agatctccta
421 cagcggccag ttcttggtca aatccggcta cgccttcgtg gactgcccgg acgagcactg
481 ggcgatgaag gccatcgaaa ctttctccgg gaaagtagaa ttacaaggaa aacgcttaga
541 gattgaacat tcggtgccca aaaaacaaag gagccggaaa attcaaatcc gaaatattcc
601 accccagctc cgatgggaag tactggacag cctgctggct cagtatggta cagtagagaa
661 ctgtgagcaa gtgaacaccg agagtgagac ggcagtggtg aatgtcacct attccaaccg
```

-continued

```
 721 ggagcagacc aggcaagcca tcatgaagct gaatggccac cagttggaga accatgccct
 781 gaaggtctcc tacatccccg atgagcagat agcacaggga cctgagaatg ggcgccgagg
 841 gggctttggc tctcggggtc agccccgcca gggctcacct gtggcagcgg gggcccagc
 901 caagcagcag caagtggaca tcccccttcg gctcctggtg cccacccagt atgtgggtgc
 961 cattattggc aaggaggggg ccaccatccg caacatcaca aaacagaccc agtccaagat
1021 agacgtgcat aggaaggaga acgcaggtgc agctgaaaaa gccatcagtg tgcactccac
1081 ccctgagggc tgctcctccg cttgtaagat gatcttggag attatgcata aagaggctaa
1141 ggacaccaaa acggctgacg aggttcccct gaagatcctg gcccataata actttgtagg
1201 gcgtctcatt ggcaaggaag gacggaacct gaagaaggta gagcaagata ccgagacaaa
1261 aatcaccatc tcctcgttgc aagaccttac cctttacaac cctgagagga ccatcactgt
1321 gaagggggcc atcgagaatt gttgcagggc cgagcaggaa ataatgaaga aagttcggga
1381 ggcctatgag aatgatgtgg ctgccatgag cctgcagtct cacctgatcc ctggcctgaa
1441 cctggctgct gtaggtcttt tcccagcttc atccagcgca gtcccgccgc ctcccagcag
1501 cgttactggg gctgctccct atagctcctt tatgcaggct cccgagcagg agatggtgca
1561 ggtgtttatc cccgcccagg cagtgggcgc catcatcggc aagaaggggc agcacatcaa
1621 acagctctcc cggtttgcca gcgcctccat caagattgca ccacccgaaa cacctgactc
1681 caaagttcgt atggttatca tcactggacc gccagaggcc caattcaagg ctcagggaag
1741 aatctatggc aaactcaagg aggagaactt ctttggtccc aaggaggaag tgaagctgga
1801 gacccacata cgtgtgccag catcagcagc tggccgggtc attggcaaag gtggaaaaac
1861 ggtgaacgag ttgcagaatt tgacggcagc tgaggtggta gtaccaagag accagacccc
1921 tgatgagaac gaccaggtca tcgtgaaaat catcggacat ttctatgcca gtcagatggc
1981 tcaacggaag atccgagaca tcctggccca ggttaagcag cagcatcaga agggacagag
2041 taaccaggcc caggcacgga ggaagtgacc agcccctccc tgtcccttcg agtccaggac
2101 aacaacgggc agaaatcgag agtgtgctct ccccggcagg cctgagaatg agtgggaatc
2161 cgggacacct gggccgggct gtagatcagg tttgcccact tgattgagaa agatgttcca
2221 gtgaggaacc ctgatctctc agccccaaac acccacccaa ttggcccaac actgtctgcc
2281 cctcggggtg tcagaaattc tagcgcaagg cacttttaaa cgtggattgt ttaaagaagc
2341 tctccaggcc ccaccaagag ggtggatcac acctcagtgg gaagaaaaat aaaatttcct
2401 tcaggtttta aaaacatgca gagaggtgtt ttaatcagcc ttaaaggatg gttcatttct
2461 tgaccttaat gttttttccaa tcttcttccc cctacttggg taattgatta aaatacctcc
2521 atttacggcc tctttctata tttacactaa ttttttttatc tttattgcta ccagaaaaaa
2581 atgcgaacga atgcattgct ttgcttacag tattgactca agggaaaaga actgtcagta
2641 tctgtagatt aattccaatc actccctaac caataggtac aatacgaaat gaagaagagg
2701 ggaaaatggg gagaaagatg gttaaaatac ataataatcc acgtttaaaa ggagcgcact
2761 tgtggctgat ctatgccaga tcaccatctt caaattggca caactgaaat ttccccactc
2821 tgttggggct tccccaccac attcatgtcc ctctcccgtg taggtttcac attatgtcca
2881 ggtgcacata ggtggtattg aatgctcagc agggtagggg ctgaccactg tccctgattc
2941 ccatcgttct caggcggatt ttatattttt ttaaagtcta ttttaatgat tggatatgag
3001 cactgggaag gggacgctaa ctccccttga taaagtctcg gttccatgga ggacttgagt
3061 ggccccaaag gctgccacgg tgccctcacc ccagcccatg tgctcccata agggctggtt
3121 cctagaggca ggggttgtgg ggcactccca gccacggcac tgttaccttg gtggtgggac
```

-continued

```
3181 ttggaacccaaccctgagctcccgataaagctaaagtccatcatctggcaaattcagtaa
3241 attggagagtacttgcttctgtttgtatctgagaggaatttttaactgacggcttctgtc
3301 tccatgaatcattatcagcatgatgaaaggtgtgtctaaaaaacaattcagaataccagc
3361 agcattgtacagcaaggggtaaataagcttaatttattaatttaccaggcttaattaaga
3421 tcccatggagtgtttagccctttgtgggagacagaagccatcagttaaatgaggttaggcc
3481 tctcctcctaatatactgattgacaatgcatattagccaggtaatgcactttagctaccc
3541 tggacaatgctatcaagtgtgctgggaagggaggaaggcctctctacatatggaaaagcc
3601 catgcgtggagttcccctcctttcaacattgcaacaacagtaacaacaagacaaccgcaa
3661 catgtgggcgtagtcaggcaatgctgtgtgcgaagtaaactacctcaaggtatgaagtta
3721 cctcagcaatttattttccttttttgttccccccaacccccattaaaaaaattttttttgat
3781 ttttgttttttgcagcttgctgatatttttatataaaaaagaaaagcaaagcaaagaga
3841 agctgatagtcttgaatattttatttttttaatgaaaagaaaaaacaagaagttatgtt
3901 tcataatttcttacaacatgagccagtaaccctttaggaactctctatggagaacaggcc
3961 tggtgggaaaggctttggggggctgccccctttaggaggaggctagtgctaagagggaaggc
4021 ccaggtttgagagagcccagaggggcagagcccagagcctttgtttggccctgatctctga
4081 cttctagagccccagctgctggcggctgctggaatatcctacctgataggattaaaaggc
4141 ctagtggagctgggggctctcagtggttaaacaatgcccacaaccaaccagctggccct
4201 tggtctcctctcttcctcctttggttaaaagagcatctcagccagcttttcccaccagtg
4261 gtgctgttgagatattttaaaatattgcctccgttttatcgaggagagaaataataacta
4321 aaaaatatacccttttaaaaaaacctatattctctgtctaaaaatatgggagctgagatt
4381 ccgttcgtggaaaaaagacaaggccaccctctcgccctcagagaggtccacctggtttgt
4441 cattgcaatgcttttcattttttttttttgttattgtttcatttcagttccgtcttgcta
4501 ttcttcctaatctatatccatagatctaaggggcaaacagatactagttaactgccccca
4561 cctctgtctccctgtcttctttagatcggtctgattgattttaaaagtggacccaaactt
4621 agggaattctctgatttagggtggctggtggcaaggaggggcaggggatatggggacgtga
4681 ctgggacaggttcctgccttatcatttctccctaggacattcccttgtagcccccagaa
4741 ttgtctggcccaaattgaatagaagcagaaaaacatttagggataacatcaggccagtag
4801 aattaagcctctccacctgtcccaaccataaaagggtctcccagctttccatctctggc
4861 tctatatgcttatcccaaaacaaagcagataacgttcagacgtcggccatttagtaatt
4921 taaagcgaatttccagcagcaagcatgcttgatatctggttcagactatcatcaggaag
4981 aaaaaaaaatcccacagtacctgaaatgtgattgttgcagtgttcagtttccttggggcc
5041 ctgctcccttcacaccttgagcccaagtccttttccgttgctgattcagctcccagaag
5101 agacgaggaagtgtgtggcaagggactggaaaacttcacttgcttggattaggcaaggct
5161 ccactcattgttgatatttgcccagcaggaaaatcatgtaagttataccaccagaaagca
5221 aaaggagcatggtttggtggttaaggtttagtgggatgaaggacctgtcttggtgggccg
5281 ggccctcttgtgccccgtagctaggtcttagggcaactccttgccctcctgctcagcac
5341 ctccatttccccatccttggtgagataacaagctatcgcgaaaagcacttgggagatttg
5401 gatgatttgagaagagtgacttaaaaaaaatgcttctgtgctctaagatatatatgtgtg
5461 tgtgtgtgctacatatatatttttaagaaaggaccatctctttaggatatattttaaat
5521 tctttgaaacacataaccaaaatggtttgattcactgactgactttgaagctgcatctgc
```

-continued

```
5581 cagttacacc ccaaatggct ttaatccct ctcgggtctg gttgccttt gcagtttggg 5641 ttgtggactc agctcctgtg aggggtctgg ttaggagaga gccattttta aggacaggga 5701 gttttatagc cctttctac tttcctcccc tcctcccagt ccttatcaat cttttttcct 5761 ttttcctgac cccctccttc tggaggcagt tgggagctat ccttgtttat gcctcactat 5821 tggcagaaaa gaccccattt aaaacccaga gaacactgga ggggatgct ctagttggtt 5881 ctgtgtccat tttcctctgt gccaaagaca gacagacaga ggctgagaga ggctgttcct 5941 gaatcaaagc aatagccagc tttcgacaca tacctggctg tctgaggagg aaggcctcct 6001 ggaaactggg agctaagggc gaggcccttc ccttcagagg ctcctggggg attagggtgt 6061 ggtgtttgcc aagccaaggg gtagggagcc gagaaattgg tctgtcggct cctggttgca 6121 ctttgggaa ggagaggaag tttgggctc caggtagctc cctgttgtgg gactgctctg 6181 tcccctgccc ctactgcaga gatagcactg ccgagttccc ttcaggcctg gcagacgggc 6241 agtgaggagg ggcctcagtt agctctcaag ggtgccttcc cctcctccca acccagacat 6301 accctctgcc aaactgggaa ccagcagtgc tagtaactac ctcacagagc cccagagggc 6361 ctgcttgagc cttcttgctc cacaggagaa gctggtgcct ctaggcaacc ccttcctccc 6421 acctctcatc agggtggg gttctccttt ctttccctg aagtgtttat ggggagatcc 6481 tagtggcttt gccattcaaa ccactcgact gtttgcctgt ttcttgaaaa ccagtagaag 6541 ggaaacagca cagcctgtca cagtaattgc aggaagattg aagaaaaatc ctcatcaatg 6601 ccaggggaca taaaagccat ttccccttcca aatactcgac aatttagatg cagaacattt 6661 ctctgtattc agactagag taacaccagc tgaaaactgc agtttctttc ctttggatac 6721 ataaggcttc tctatcgggg tacgggacag ggaggaggcc tcatgtctga agggggattt 6781 aggggcgaga gccccagccc tgacccctcgg tcctgtgcac cgctttggg cacagtctga 6841 tggcgccttt gctggcgcct tagtatggtt gactccggat ggacaaaaga aaaaaatttt 6901 tttttcttga atgaaatagc aggaagctcc tcgggagcat gtgttttgat taaccgcagg 6961 tgatggatgc tacgagtata aatggattaa ctacctcaat ccttacagta agattggaac 7021 taagggcagg gactcatgca taagggtatg aatcccagcc aggacaagtg agttgaggct 7081 tgtgccacaa aaggtttgtc cttggggaac aggcaggcct gccaggatcc ccccatatc 7141 gattgggctg ggaggggctgg ccatgaggtc cccactttct gctttccttg cccatgtgtc 7201 accccttggg cctccagctt gtccctctct cactttctat agctttgttg gaccagatgg 7261 tgaggaaagg aatggcctct tcccttctag aggggctgg ctggagtgag acctgggct 7321 tggcctggaa cccaccacac agccccaaag tcaggaagcc tgggaaacc agagctgaga 7381 cctcttcaac agggtttctt tgagatccta cacctccatt gggccctttt tcagtcttca 7441 atgggggccc agttggctct agaaggagaa gaggtgaagc aggatccttt gccctggggg 7501 agtctgaggg cgcggtcctt ggactcattc aggccgtctt tgtagttggg ggagttccac 7561 tgggcgatcc cagcccctcc ccacccaccc tctaatggac ctcctcatag aagccccatt 7621 tcacttttgt tttatctacc tcttagcaaa acaatagata aattaggtag tggcagctcc 7681 acttgcttag gttagggggg gaaaagagatt tctttttcca aggaaaaaaa atattccctt 7741 gagaatactt tccaaaaaat aaaattaaaa aaaaaaaaac caaaaaaaaa aatttttttt 7801 taaagggag acattttcca gtgaccactg gattgttta atttcccaag cttttttttc 7861 ccccataaat aagtttcact cttggcgat tttcttcact tgtttaagat aacgtgctag 7921 ctattccaac aggtaacagc tttcacagtc tgcccctggc ctgtctcacc ccatccccca 7981 ccctattcct gccagtgagt ccttcctgtg cttctctccc ttctcccctc ccagccagct
```

-continued

```
8041 gacttcagtc acccctgtcc cccctcccct gccaataagc tcccccagga ataaaggctt 8101 tgttttgggg atgcttaaat cttgactggc acttcccggc tgtgggggct ggggagccac 8161 ttgtaacatt tctgtgcaga ttttatgtta gccactgcta tgtaaaagca cgttcaaaat 8221 gaatttcagc agattatgtg ttaccataat gaataaacgt cctctatcac catttggagt 8281 ctccctttc tccaggatct tgatcctggt ccccaaaacc agagtgaatc aaaagagctt 8341 cctcccctga ggcaaagtgg atttgtaagc agttctgaaa catcacttac tcagaagagg 8401 gaacgatgta ttttgatgag tgcaaattgg gaagagctgg aggcctactg cttgggacag 8461 ttttttttt tttttttttt ttaaatatga gtgctagctt attctgtaat tgcggcaact 8521 ttgaaaattg tattttactg gaaatctgcc agccatcacc acccgatttt gattgtatcc 8581 ttcctcccat cctttaatct gttcattgct ttgggggagg tgggcagct ggctcacacg 8641 ttggagtttg ttctttgatg gatgaacgaa cactccagtt ttctttcccg tgaaggttgt 8701 ttcagccaca aaccacttca ttttgctgtt tcaatttcaa aataaaagga aacttatatt 8761 gaaagacaa
```

By "IL2RA nucleic acid molecule" is meant a polynucleotide encoding an IL2RA polypeptide (e.g., NP_000408). An exemplary IL2RA nucleic acid molecule is provided at NCBI Accession No. NM_000417. An exemplary IL2RA mRNA transcript is provided below (SEQ ID NO: 2):

```
   1 ggcagtttcc tggctgaaca cgccagccca atacttaaag agagcaactc ctgactccga 61 tagagactgg atggacccac aagggtgaca gcccaggcgg accgatcttc ccatcccaca 121 tcctccggcg cgatgccaaa agaggctga cggcaactgg gccttctgca gagaaagacc 181 tccgcttcac tgccccggct ggtcccaagg gtcaggaaga tggattcata cctgctgatg 241 tggggactgc tcacgttcat catggtgcct ggctgccagg cagagctctg tgacgatgac 301 ccgccagaga tcccacacgc cacattcaaa gccatggcct acaaggaagg aaccatgttg 361 aactgtgaat gcaagagagg tttccgcaga ataaaagcg ggtcactcta tatgctctgt 421 acaggaaact ctagccactc gtcctgggac aaccaatgtc aatgcacaag ctctgccact 481 cggaacacaa cgaaacaagt gacacctcaa cctgaagaac agaaagaag gaaaaccaca 541 gaaatgcaaa gtccaatgca gccagtggac caagcgagcc ttccaggtca ctgcagggaa 601 cctccaccat gggaaaatga agccacagag agaatttatc atttcgtggt ggggcagatg 661 gtttattatc agtgcgtcca gggatacagg gctctacaca gaggtcctgc tgagagcgtc 721 tgcaaaatga cccacgggaa gacaaggtgg acccagcccc agctcatatg cacaggtgaa 781 atggagacca gtcagtttcc aggtgaagag aagcctcagg caagcccga aggccgtcct 841 gagagtgaga cttcctgcct cgtcacaaca acagattttc aaatacagac agaaatggct 901 gcaaccatgg agacgtccat atttacaaca gagtaccagg tagcagtggc cggctgtgtt 961 ttcctgctga tcagcgtcct cctcctgagt gggctcacct ggcagcggag acagaggaag 1021 agtagaagaa caatctagaa aaccaaaaga acaagaattt cttggtaaga agccgggaac 1081 agacaacaga agtcatgaag cccaagtgaa atcaaaggtc ctaaatggtc gcccaggaga 1141 catccgttgt gcttgcctgc gttttggaag ctctgaagtc acatcacagg acacggggca 1201 gtggcaacct tgtctctatg ccagctcagt cccatcagag agcgagcgct acccacttct 1261 aaatagcaat ttcgccgttg aagaggaagg gcaaaccac tagaactctc catcttattt 1321 tcatgtatat gtgttcatta aagcatgaat ggtatggaac tctctccacc ctatatgtag
```

```
1381 tataaagaaa agtaggttta cattcatctc attccaactt cccagttcag gagtcccaag 1441 gaaagcccca gcactaacgt aaatacacaa cacacacact ctaccctata caactggaca 1501 ttgtctgcgt ggttcctttc tcagccgctt ctgactgctg attctcccgt tcacgttgcc 1561 taataaacat ccttcaagaa ctctgggctg ctacccagaa atcattttac ccttggctca 1621 atcctctaag ctaaccccct tctactgagc cttcagtctt gaatttctaa aaacagagg 1681 ccatggcaga ataatctttg ggtaacttca aaacgggca gccaaaccca tgaggcaatg 1741 tcaggaacag aaggatgaat gaggtcccag gcagagaatc atacttagca aagttttacc 1801 tgtgcgttac taattggcct ctttaagagt tagtttcttt gggattgcta tgaatgatac 1861 cctgaatttg gcctgcacta atttgatgtt tacaggtgga cacacaaggt gcaaatcaat 1921 gcgtacgttt cctgagaagt gtctaaaaac accaaaaagg gatccgtaca ttcaatgttt 1981 atgcaaggaa ggaaagaaag aaggaagtga agagggagaa gggatggagg tcacactggt 2041 agaacgtaac cacggaaaag agcgcatcag gcctggcacg gtggctcagg cctataaccc 2101 cagctcccta ggagaccaag gcgggagcat ctcttgaggc caggagtttg agaccagcct 2161 gggcagcata gcaagacaca tccctacaaa aaattagaaa ttggctggat gtggtggcat 2221 acgcctgtag tcctagccac tcaggaggct gaggcaggag gattgcttga gcccaggagt 2281 tcgaggctgc agtcagtcat gatggcacca ctgcactcca gcctgggcaa cagagcaaga 2341 tcctgtcttt aaggaaaaaa agacaagatg agcataccag cagtccttga acattatcaa 2401 aaagttcagc atattagaat caccggagg ccttgttaaa agagttcgct gggcccatct 2461 tcagagtctc tgagttgttg gtctggaata gagccaaatg ttttgtgtgt ctaacaattc 2521 ccaggtgctg ttgctgctgc tactattcca ggaacacact ttgagaacca ttgtgttatt 2581 gctctgcacg cccacccact ctcaactccc acgaaaaaaa tcaacttcca gagctaagat 2641 ttcggtggaa gtcctggttc catatctggt gcaagatctc ccctcacgaa tcagttgagt 2701 caacattcta gctcaacaac atcacacgat taacattaac gaaaattatt catttgggaa 2761 actatcagcc agttttcact tctgaagggg caggagagtg ttatgagaaa tcacggcagt 2821 tttcagcagg gtccagattc agattaaata actattttct gtcatttctg tgaccaacca 2881 catacaaaca gactcatctg tgcactctcc ccctcccct tcaggtatat gttttctgag 2941 taaagttgaa aagaatctca gaccagaaaa tatagatata tatttaaatc ttacttgagt 3001 agaactgatt acgacttttg ggtgttgagg ggtctataag atcaaaactt ttccatgata 3061 atactaagat gttatcgacc atttatctgt ccttctctca aaagtgtatg gtggaatttt 3121 ccagaagcta tgtgatacgt gatgatgtca tcactctgct gttaacatat aataaattta 3181 ttgctattgt ttataaaaga ataaatgata tttttt
```

By "TNFRSF12A nucleic acid molecule" is meant a polynucleotide encoding an TNFRSF12A polypeptide (e.g., NP_057723). An exemplary TNFRSF12A nucleic acid molecule is provided at NCBI Accession No. NM_016639. An exemplary TNFRSF12A mRNA transcript is provided below (SEQ ID NO: 3):

```
  1 aaggcggggg cggggcggg gcggcggccg tgggtccctg ccggccggcg gcgggcgcag 61 acagcggcgg gcgcaggacg tgcactatgg ctcggggctc gctgcgccgg ttgctgcggc 121 tcctcgtgct ggggctctgg ctggcgttgc tgcgctccgt ggccggggag caagcgccag 181 gcaccgcccc ctgctcccgc ggcagctcct ggagcgcgga cctggacaag tgcatggact 241 gcgcgtcttg cagggcgcga ccgcacagcg acttctgcct gggctgcgct gcagcacctc 301 ctgcccccct tccggctgct tggcccatcc ttgggggcgc tctgagcctg accttcgtgc
```

```
 361 tggggctgct ttctggcttt ttggtctgga gacgatgccg caggagagag aagttcacca 421 cccccataga ggagaccggc ggagagggct gcccagctgt ggcgctgatc cagtgacaat 481 gtgcccctg ccagccgggg ctcgcccact catcattcat tcatccattc tagagccagt 541 ctctgcctcc cagacgcggc gggagccaag ctcctccaac cacaaggggg gtgggggcg 601 gtgaatcacc tctgaggcct gggcccaggg ttcagggaa ccttccaagg tgtctggttg 661 ccctgcctct ggctccagaa cagaaggga gcctcacgct ggctcacaca aaacagctga 721 cactgactaa ggaactgcag catttgcaca ggggaggggg gtgccctcct tcctagaggc 781 cctgggggcc aggctgactt ggggggcaga cttgacacta ggccccactc actcagatgt 841 cctgaaattc caccacgggg gtcaccctgg ggggttaggg acctattttt aacactaggg 901 ggctggccca ctaggagggc tggccctaag atacagaccc ccccaactcc ccaaagcggg 961 gaggagatat ttattttggg gagagtttgg aggggaggga gaatttatta ataaaagaat 1021 ctttaacttt aaaaaaaaaa aaaaaaa
```

By "increases" is meant a positive alteration of at least 10%, 25%, 50%, 75%, 100%, 200%, 300%, 400%, 500%, 1000%, or more.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

The terms "marker" and "epigenetic marker" are used interchangeably herein to refer to a distinguishing or characteristic substance that may be found in a biological material. The substance may, for example, be a protein, an enzyme, an RNA molecule or a DNA molecule. Non-limiting examples of such a substance include a kinase, a methylase, and an acetylase. The terms also refer to a specific characteristic of the substance, such as, but not limited to, a specific phosphorylation, methylation, or acetylation event or pattern, making the substance distinguishable from otherwise identical substances. The terms further refer to a specific modification, event or step occurring in a signaling pathway or signaling cascade, such as, but not limited to, the deposition or removal of a specific phosphate, methyl, or acetyl group.

By "marker profile" is meant a characterization of the expression or expression level of two or more polypeptides or polynucleotides "Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein a "nucleic acid or oligonucleotide probe" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. It will be understood by one of skill in the art that probes may bind target sequences lacking complete complementarity with the probe sequence depending upon the stringency of the hybridization conditions. The probes are preferably directly labeled with isotopes, for example, chromophores, lumiphores, chromogens, or indirectly labeled with biotin to which a streptavidin complex may later bind. By assaying for the presence or absence of the probe, one can detect the presence or absence of a target gene of interest.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "quantitative trait" refer to a phenotype or characteristics of an individual that can be attributed to the effect two or more genes.

As used herein, "quantitative trait locus (QTL)" refers to a DNA sequence or segment located within the genome containing or linked to the genes that underlie a quantitative trait.

As used herein, "expression quantitative trait loci (eQTLs)" are genomic loci that regulate expression levels of mRNAs or proteins. The abundance of a gene transcript is directly modified by polymorphisms in regulatory elements that alter the level of a gene transcript. These can be mapped and the level of a gene transcript can be used as a quantitative trait. Mapping eQTLs is performed using standard QTL mapping methods that test the linkage between variation in expression and genetic polymorphisms. In one embodiment, eQTL is determined by statistical regression of the genotype of an SNP and the expression for the transcript.

By "reference" is meant a standard or control condition. In one embodiment, the level of gene expression in a tissue sample of a subject having GI Symptomatic ASD is compared to the gene expression in a tissue sample from a control subject.

"Sample" or "biological sample" as used herein means a biological material isolated from a subject, including any tissue, cell, fluid, or other material obtained or derived from the subject (e.g., a human). The biological sample may contain any biological material suitable for detecting the desired analytes, and may comprise cellular and/or non-cellular material obtained from the subject. In various embodiments, the biological sample may be obtained from the small bowel, stomach, or esophagus. In particular embodiments, the biological sample is obtained from the ileum or colon . . . .

By "single nucleotide polymorphism" or "SNP" is meant a DNA sequence variation occurring when a single nucleotide in the genome differs between members of a biological species or paired chromosomes in an individual. SNPs are used as genetic markers for variant alleles.

By "specifically binds" is meant a compound or antibody that recognizes and binds a polypeptide of the invention, but which does not substantially recognize and bind other molecules in a sample.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and most preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "target nucleic acid molecule" is meant a nucleic acid or biomarker of the sample that is to be detected.

A "therapeutic" treatment is a treatment administered to a subject who exhibits a sign or symptom of pathology, for the purpose of diminishing or eliminating that sign or symptom.

As used herein, "treating a disease or disorder" means reducing the frequency with which a sign or symptom of the disease or disorder is experienced by a patient.

The phrase "therapeutically effective amount," as used herein, refers to an amount that is sufficient or effective to prevent or treat (delay or prevent the onset of, prevent the progression of, inhibit, decrease or reverse) a disease or disorder associated with ASD, including alleviating signs and symptoms of such diseases or disorders.

By "variant" as is meant a polynucleotide or polypeptide sequence that differs from a wild-type or reference sequence by one or more nucleotides or one or more amino acids.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art.

Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. C in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS.

Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to the identification of biomarkers that are associated with an ASD-associated inflammatory disorder. The invention is partly based on the comparison of gene expression profiles (differentially expressed transcripts) in both ileal and colonic tissues in GI symptomatic ASD children ($ASD^{IC}$) and non-ASD control groups (Crohn's disease, ulcerative colitis, and normal).

In one embodiment, the biomarkers of the invention are useful for discriminating between different inflammatory disorders.

Such biomarkers could be used for ASD-associated inflammatory disorder screening and diagnosis, as well as potentially for designing novel pharmaceuticals that would target the genes responsible for the DETs, and in assessing response to new therapies. Given the probability of multiple underlying pathogenic mechanisms of some ASD-associated inflammatory disorders, the present invention provides novel biomarkers present in the biological sample of a subject. The biomarkers of the invention allow a more accurate diagnosis, prognosis, or treatment strategy of an ASD-associated inflammatory disorder.

In one embodiment, the present inventive includes a method of screening for an Autism Spectrum Disorder in a patient by analyzing differential gene expression patterns comprising the steps of: obtaining a nucleic acid sample from cells of a patient; performing a nucleic acid analysis on the nucleic acid samples to obtain a gene expression analysis data set; and comparing said data set to a control data set corresponding to a gene ensemble of differentially expressed genes indicative of autism spectrum disorder, wherein autism spectrum disorder is indicated upon observing statistically significant differential gene expression. In one embodiment, the nucleic acid sample is obtained from cells of the gastrointestinal tract of a patient.

In some embodiments of the invention, one can observe an expression profile of at least, 2, 3, 4, 5, 6, 7, 8, 9 or 10 or more genes whose expression is shown to be dysregulated in autism spectrum disorders (e.g. using microarray technologies). In certain embodiments of the invention, the method is performed on a plurality of individuals and the results are then categorized based upon similarities or differences in their gene expression profiles. Optionally, the expression profile(s) is observed and/or collected and/or stored using a computer system comprising a processor element and a memory storage element adapted to process and store data from one or more expression profiles (e.g. in a library of such profiles). In this context, certain embodiments of the invention comprise an electronically searchable library of profiles, wherein the profiles include an individual's gene expression data in combination with other diagnostic data, for example assessments of behavior associated with autism spectrum disorders.

In one embodiment, the invention relates to one or more biomarkers of ASD. The invention is partly based upon the discovery of differentially expressed transcripts (DETs) detected in samples obtained from subjects with $ASD^{IC}$, compared to samples obtained from either non-disease control subjects, subjects with Crohn's disease, or subjects with ulcerative colitis. In one embodiment, the biomarker of the invention is one listed in Table 6. In another embodiment, the biomarker of the invention is one listed in Table 9. In one embodiment, the biomarker of the invention is detected to have decreased expression in a subject with ASD compared to a control sample. In another embodiment, the biomarker of the invention is detected to have increased expression in a subject with ASD compared to a control sample.

Diagnostic Methods

The methods of the invention also include the use of a biomarker to detect a gastrointestinal disorder and/or autism spectrum disorder in a subject (e.g., a human subject). As described herein, altered gene expression of transcripts indicated the presence of a gastrointestinal disorder in ASD individuals. The molecular evidence indicated an overlapping, yet unique, IBD-like condition in ASD children.

Biological samples include tissue samples (e.g., cell samples, biopsy samples), such as tissue from colon or ileum. Biological samples also include bodily fluids, including, but not limited to, blood, blood serum, plasma, saliva, and urine. Elevated levels of a biomarker alone or in combination with one or more additional markers are considered a positive indicator of a gastrointestinal and/or austism spectrum disorder. In general, an increase in polypeptide or polynucleotide levels is indicative Any suitable method can be used to detect one or more of the markers described herein. Successful practice of the invention can be achieved with one or a combination of methods that can detect and, preferably, quantify the markers. These methods include, without limitation, hybridization-based methods, including those employed in biochip arrays, mass spectrometry (e.g., laser desorption/ionization mass spectrometry), fluorescence (e.g. sandwich immunoassay), surface plasmon resonance, ellipsometry and atomic force microscopy. Expression levels of markers (e.g., polynucleotides or polypeptides) are compared by procedures well known in the art, such as RT-PCR, Northern blotting, Western blotting, flow cytometry, immunocytochemistry, binding to magnetic and/or antibody-coated beads, in situ hybridization, fluorescence in situ hybridization (FISH), flow chamber adhesion assay, ELISA, microarray analysis, or colorimetric assays. Methods may further include, one or more of electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)", atmospheric pressure photoionization mass spectrometry (APPI-MS), APPI-MS/MS, and APPI-(MS)n, quadrupole mass spectrometry, fourier transform mass spectrometry (FTMS), and ion trap mass spectrometry, where n is an integer greater than zero. Detection methods may include use of a biochip array. Biochip arrays useful in the invention include protein and polynucleotide arrays. One or more markers are captured on the biochip array and subjected to analysis to detect the level of the markers in a sample.

Markers may be captured with capture reagents immobilized to a solid support, such as a biochip, a multiwell microtiter plate, a resin, or a nitrocellulose membrane that is subsequently probed for the presence or level of a marker. Capture can be on a chromatographic surface or a biospecific surface. For example, a sample containing the markers, such as serum, may be used to contact the active surface of a biochip for a sufficient time to allow binding. Unbound molecules are washed from the surface using a suitable eluant, such as phosphate buffered saline. In general, the more stringent the eluant, the more tightly the proteins must be bound to be retained after the wash.

Upon capture on a biochip, analytes can be detected by a variety of detection methods selected from, for example, a gas phase ion spectrometry method, an optical method, an electrochemical method, atomic force microscopy and a radio frequency method. In one embodiment, mass spectrometry, and in particular, SELDI, is used. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and nonimaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

Mass spectrometry (MS) is a well-known tool for analyzing chemical compounds. Thus, in one embodiment, the methods of the present invention comprise performing quantitative MS to measure the serum peptide marker. The method may be performed in an automated (Villanueva, et al., Nature Protocols (2006) 1(2):880-891) or semi-automated format. This can be accomplished, for example with MS operably linked to a liquid chromatography device (LC-MS/MS or LC-MS) or gas chromatography device (GC-MS or GC-MS/MS). Methods for performing MS are known in the field and have been disclosed, for example, in US Patent Application Publication Nos: 20050023454; 20050035286; U.S. Pat. No. 5,800,979 and references disclosed therein.

In an additional embodiment of the methods of the present invention, multiple markers are measured. The use of multiple markers increases the predictive value of the test and provides greater utility in diagnosis, patient stratification and patient monitoring. The process called "Pattern recognition" detects the patterns formed by multiple markers greatly improves the sensitivity and specificity of clinical markers for predictive medicine. Subtle variations in data from clinical samples indicate that certain patterns of protein expression can predict phenotypes such as the presence or absence of a certain disease, a particular stage of disease-progression, or a positive or adverse response to drug treatments. In the present invention, additional markers may include cytokine profiles and/or serum antibodies directed against gut microbes.

Expression levels of particular nucleic acids or polypeptides are correlated with a gastrointestinal disorder and/or autistic spectrum disorder and thus are useful in diagnosis. Methods for measuring levels of polypeptide include immunoassay, ELISA, western blotting and radioimmunoassay. Oligonucleotides or longer fragments derived from a nucleic acid sequence described herein, antibodies that bind a polypeptide described herein, or any other method known in the art may be used to monitor expression of a polynucleotide or polypeptide of interest. In other embodiments, a 1.5, 2, 3, 4, 5, or 6-fold change in the level of a marker of the invention is indicative of a gastrointestinal and/or autistic spectrum disorder. In yet another embodiment, an expression profile that characterizes alterations in the expression two or more markers is correlated with a particular disease state (e.g., gastrointestinal and/or autistic spectrum disorder).

The diagnostic methods described herein can be used individually or in combination with any other diagnostic method described herein for a more accurate diagnosis of the presence of a gastrointestinal and/or autistic spectrum disorder. The diagnostic methods described herein can also be used to reliably distinguish ileoclitis in an individual having autism spectrum disorder from Crohn's disease or inflammatory bowel disease.

As indicated above, the invention provides methods for aiding diagnosis of a gastrointestinal and/or autism spectrum disorder using one or more markers, as specified herein. These markers can be used alone, in combination with other markers in any set, or with entirely different markers in aiding diagnosis. The measurement of markers may also involve quantifying the markers to correlate the detection of markers with a diagnosis of a gastrointestinal and/or autism spectrum disorder. Thus, if the amount of the markers detected in a subject being tested is different compared to a control amount (i.e., higher than the control), then the subject being tested has a higher probability of having a gastrointestinal and/or autism spectrum disorder. The correlation may take into account the amount of the marker or markers in the sample compared to a control amount of the marker or markers (e.g., in normal subjects). A control can be, e.g., the average or median amount of marker present in comparable samples of normal subjects in normal subjects or in subjects such as where the disease or disorder is undetectable. The control amount is measured under the same or substantially similar experimental conditions as in measuring the test amount. As a result, the control can be employed as a reference standard, where the normal (non-disease) phenotype is known, and each result can be compared to that standard, rather than re-running a control.

Accordingly, a marker profile may be obtained from a subject sample and compared to a reference marker profile obtained from a reference population, so that it is possible to classify the subject as belonging to or not belonging to the reference population. The correlation may take into account the presence or absence of the markers in a test sample and the frequency of detection of the same markers in a control. The correlation may take into account both of such factors to facilitate diagnosis of a gastrointestinal and/or autism spectrum disorder.

In certain embodiments of the methods of qualifying a disorder, the methods further comprise managing subject treatment based on the status. The invention also provides for such methods where the markers (or specific combination of markers) are measured again after subject management. In these cases, the methods are used to monitor the status of the disorder or progression of the disorder.

Any marker, individually, is useful in aiding in the diagnosis of a gastrointestinal and/or autistic spectrum disorder. First, the selected marker is detected in a subject sample using the methods described herein. Then, the result is compared with a control that distinguishes disorder status from non-disorder status. As is well understood in the art, the techniques can be adjusted to increase sensitivity or specificity of the diagnostic assay depending on the preference of the diagnostician.

The diagnosis of a gastrointestinal and/or autistic spectrum disorder can be used to inform treatment selection. Treatments for such ASD or ASD inflammatory disorders include without limitation treatment with corticosteroids, immunomodulators, 5-aminosalicylic acid preparations, cytokine specific antagonists, dietary restrictions, antimicrobials, probiotics, and supplemental digestive enzymes. Additionally, treatment for such ASD or ASD inflammatory disorders may include targeted therapies that decrease or eliminate the expression of any of the nucleic acid molecules or polypeptides of the genes responsible for the unique transcriptomes described herein.

While individual markers are useful diagnostic markers, in some instances, a combination of markers provides greater predictive value than single markers alone. The detection of a plurality of markers (or absence thereof, as the case may be) in a sample can increase the percentage of true positive and true negative diagnoses and decrease the percentage of false positive or false negative diagnoses. Thus, preferred methods of the present invention comprise the measurement of more than one marker.

Microarrays

As reported herein, a number of biomarkers have been identified that are associated with a gastrointestinal and/or autistic spectrum disorder. In particular, the invention provides diagnostic methods and compositions useful for identifying an expression profile that identifies a subject as having a gastrointestinal and/or autistic spectrum disorder. Such assays can be used to measure an alteration in the level of a gene transcript or polypeptide encoded by the transcript.

The polypeptides and nucleic acid molecules of the invention are useful as hybridizable array elements in a microarray. The array elements are organized in an ordered fashion such that each element is present at a specified location on the substrate. Useful substrate materials include membranes, composed of paper, nylon or other materials, filters, chips, glass slides, and other solid supports. The ordered arrangement of the array elements allows hybridization patterns and intensities to be interpreted as expression levels of particular genes or proteins. Methods for making nucleic acid microarrays are known to the skilled artisan and are described, for example, in U.S. Pat. No. 5,837,832, Lockhart, et al. (Nat. Biotech. 14: 1675-1680, 1996), and Schena, et al. (Proc. Natl. Acad. Sci. 93: 10614-10619, 1996), herein incorporated by reference. Methods for making polypeptide microarrays are described, for example, by Ge (Nucleic Acids Res. 28: e3 . . . i-e3. vii, 2000), MacBeath et al., (Science 289: 1760-1763, 2000), Zhu et al. (Nature Genet. 26:283-289), and in U.S. Pat. No. 6,436,665, hereby incorporated by reference.

Nucleic Acid Microarrays

To produce a nucleic acid microarray, oligonucleotides may be synthesized or bound to the surface of a substrate using a chemical coupling procedure and an ink jet application apparatus, as described in PCT application WO95/251116 (Baldeschweiler et al.), incorporated herein by reference. Alternatively, a gridded array may be used to arrange and link cDNA fragments or oligonucleotides to the surface of a substrate using a vacuum system, thermal, UV, mechanical or chemical bonding procedure.

A nucleic acid molecule (e.g. RNA or DNA) derived from a biological sample may be used to produce a hybridization probe as described herein. The biological samples are generally derived from a patient, preferably as a bodily fluid (such as blood, blood serum, plasma, saliva, urine, seminal fluids, and ejaculate) or tissue sample (e.g. a tissue sample obtained by biopsy). For some applications, cultured cells or other tissue preparations may be used. The mRNA is isolated according to standard methods, and cDNA is produced and used as a template to make complementary RNA suitable for hybridization. Such methods are known in the art. The RNA is amplified in the presence of fluorescent nucleotides, and the labeled probes are then incubated with the microarray to allow the probe sequence to hybridize to complementary oligonucleotides bound to the microarray.

Incubation conditions are adjusted such that hybridization occurs with precise complementary matches or with various degrees of less complementarity depending on the degree of stringency employed. For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37 C, and most preferably of at least about 42° C.

Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/μl denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

The removal of nonhybridized probes may be accomplished, for example, by washing. The washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

A detection system may be used to measure the absence, presence, and amount of hybridization for all of the distinct nucleic acid sequences simultaneously (e.g., Heller et al., Proc. Natl. Acad. Sci. 94:2150-2155, 1997). Preferably, a scanner is used to determine the levels and patterns of fluorescence.

Detection of the presence of rs1127155 and/or rs6460055 single nucleotide polymorphisms was associated with gastrointestinal disorder in autistic children. Methods for detecting polymorphisms are known in the art, and are detailed below.

Polymerase Chain Reaction (PCR)

Polymerase chain reaction (PCR) is widely known in the art. For example, U.S. Pat. Nos. 4,683,195, 4,683,202, and 4,800,159; K. Mullis, Cold Spring Harbor Symp. Quant. Biol., 51:263-273 (1986); and C. R. Newton & A. Graham, Introduction to Biotechniques: PCR, 2nd Ed., Springer-Verlag (New York: 1997), the disclosures of which are incorporated herein by reference, describe processes to amplify a nucleic acid sample target using PCR amplification extension primers which hybridize with the sample target. As the PCR amplification primers are extended, using a DNA polymerase (preferably thermostable), more sample target is made so that more primers can be used to repeat the process, thus amplifying the sample target sequence. Typically, the reaction conditions are cycled between those conducive to hybridization and nucleic acid polymerization, and those that result in the denaturation of duplex molecules.

In the first step of the reaction, the nucleic acid molecules of the sample are transiently heated, and then cooled, in order to denature double stranded molecules. Forward and reverse primers are present in the amplification reaction mixture at an excess concentration relative to the sample target. When the sample is incubated under conditions conducive to hybridization and polymerization, the primers hybridize to the complementary strand of the nucleic acid molecule at a position 3' to the sequence of the region desired to be amplified that is the complement of the sequence whose amplification is desired. Upon hybridization, the 3' ends of the primers are extended by the polymerase. The extension of the primer results in the synthesis of a DNA molecule having the exact sequence of the complement of the desired nucleic acid sample target. The PCR reaction is capable of exponentially amplifying the desired nucleic acid sequences, with a near doubling of the number of molecules having the desired sequence in each cycle. Thus, by permitting cycles of hybridization, polymerization, and denaturation, an exponential increase in the concentration of the desired nucleic acid molecule can be achieved.

The methods of the present invention involve amplifying regions of a polynucleotide with high fidelity using a thermostable DNA polymerase having 3'→5' exonuclease activity. As defined herein, "3'→5' exonuclease activity" refers to the activity of a template-specific nucleic acid polymerase having a 3'→5' exonuclease activity associated with some DNA polymerases, in which one or more nucleotides are removed from the 3' end of an oligonucleotide in a sequential manner. Polymerase enzymes having high fidelity 3'→5' exonuclease activity are useful, for example, when primer extension must be performed with high specificity. Polymerase enzymes having 3'→5' exonuclease proofreading activity are known to those in the art. Examples of suitable proofreading enzymes include TaKaRa LA Taq (Takara Shuzo Co., Ltd.) and Pfu (Stratagene), Vent, Deep Vent (New England Biolabs). Exemplary methods for performing long range PCR are disclosed, for example, in U.S. Pat. No. 5,436,149; Barnes, Proc. Natl. Acad. Sci. USA 91:2216-2220 (1994); Tellier et al., Methods in Molecular Biology, Vol. 226, PCR Protocols, 2nd Edition, pp. 173-177; and, Cheng et al., Proc. Natl. Acad. Sci. 91:5695-5699 (1994); the contents of which are incorporated herein by reference. In various embodiments, long range PCR involves one DNA polymerase. In some embodiments, long range PCR may involve more than one DNA polymerase. When using a combination of polymerases in long range PCR, it is preferable to include one polymerase having 3'→5' exonuclease activity, which assures high fidelity generation of the PCR product from the DNA template. Typically, a non-proofreading polymerase, which is the main polymerase is also used in conjunction with the proofreading polymerase in long range PCR reactions. Long range PCR can also be performed using commercially available kits, such as LA PCR kit available from Takara Bio Inc.

Sequencing

DNA sequencing may be used to evaluate a polymorphism of the present invention. One DNA sequencing method is the Sanger method, which is also referred to as dideoxy sequencing or chain termination. The Sanger method is based on the use of dideoxynucleotides (ddNTP's) in addition to the normal nucleotides (NTP's) found in DNA. Dideoxynucleotides are essentially the same as nucleotides except they contain a hydrogen group on the 3' carbon instead of a hydroxyl group (OH). These modified nucleotides, when integrated into a sequence, prevent the addition of further nucleotides. This occurs because a phosphodiester bond cannot form between the dideoxynucleotide and the next incoming nucleotide, and thus the DNA chain is terminated. Using this method, optionally coupled with amplification of the nucleic acid target, one can now rapidly sequence large numbers of target molecules, usually employing automated sequencing apparati. Such techniques are well known to those of skill in the art.

Pyro sequencing is another method of DNA sequencing that may be used to evaluate a polymorphism of the present invention, for example as described in U.S. Pat. Publ. No. 2006008824; herein incorporated by reference). Pyrosequencing, which is also referred to as sequencing by synthesis, involves taking a single strand of the DNA to be sequenced, synthesizing its complementary strand enzymatically one base pair at a time, and detecting by chemiluminescence the base that is added. In one embodiment, the template DNA is immobile, and solutions of A, C, G, and T nucleotides are sequentially added and removed from the reaction. Light is produced only when the nucleotide solution complements the first unpaired base of the template. The sequence of solutions which produce chemiluminescent signals allows the determination of the sequence of the template. The templates for pyrosequencing can be made both by solid phase template preparation (streptavidin-coated magnetic beads) and enzymatic template preparation (apyrase+exonuclease).

In a specific embodiment, ssDNA template is hybridized to a sequencing primer and incubated with the enzymes DNA polymerase, ATP sulfurylase, luciferase and apyrase, and with the substrates adenosine 5' phosphosulfate (APS) and luciferin. The addition of one of the four deoxynucleotide triphosphates (dNTPs)(in place of dATP, dATPaS is added, which is not a substrate for a luciferase) initiates the second step. DNA polymerase incorporates the correct, complementary dNTPs onto the template, and the incorporation of the nucleotide releases pyrophosphate (PPi) stoichiometrically. ATP sulfurylase quantitatively converts PPi to ATP in the presence of adenosine 5' phospho sulfate. The ATP generated acts to catalyze the luciferase-mediated conversion of luciferin to oxyluciferin and generates visible light in amounts that are proportional to the amount of ATP. The light produced in the luciferase-catalyzed reaction is detected by a camera and analyzed in a program. Unincorporated nucleotides and ATP are degraded by the apyrase, and the reaction can restart with another nucleotide.

Pyrosequencing, optionally coupled with amplification of the nucleic acid target, can sequence large numbers of target molecules, usually employing automated sequencing apparati, including long sequences (e.g., 400 million bp/10 hr in a single run).

Real-Time PCR (rtPCR)

The presence or absence of polymorphisms in WEE1 may be detected using real-time PCR. Real-time PCR typically utilizes fluorescent probes for the selective detection of the polymorphisms. Various real-time PCR testing platforms that may be used with the present invention include: 5' nuclease (TaqMan® probes), molecular beacons, and FRET hybridization probes. These detection methods rely on the transfer of light energy between two adjacent dye molecules, a process referred to as fluorescence resonance energy transfer (see, e.g., Espy et al (2006) Clin Microbiol Rev. 2006 January; 19(1): 165-256 for a review of various rtPCR approaches that may be used with the present invention).

5' Nuclease Probes

In certain embodiments, a 5' nuclease probe may be used to detect a polymorphism of the present invention. 5' nuclease probes are often referred to by the proprietary name, TaqMan® probes. A TaqMan® probe is a short oligonucleotide (DNA) that contains a 5' fluorescent dye and 3' quenching dye. To generate a light signal (i.e., remove the effects of the quenching dye on the fluorescent dye), two events must occur. First, the probe must bind to a complementary strand of DNA, e.g., at about 60° C. Second, at this temperature, Taq polymerase, which is commonly used for PCR, must cleave the 5' end of the TaqMan® probe (5' nuclease activity), separating the fluorescent dye from the quenching dye.

In order to differentiate a single nucleotide polymorphism from a wild-type sequence in the DNA from a subject, a second probe with complementary nucleotide(s) to the polymorphism and a fluorescent dye with a different emission spectrum are typically utilized. Thus, these probes can be used to detect a specific, predefined polymorphism under the probe in the PCR amplification product. Two reaction vessels are typically used, one with a complementary probe to detect wild-type target DNA and another for detection of a specific nucleic acid sequence of a mutant strain. Because TaqMan® probes typically require temperatures of about 60° C. for efficient 5' nuclease activity, the PCR may be cycled between about 90-95° C. and about 60° C. for amplification. In addition, the cleaved (free) fluorescent dye can accumulate after each PCR temperature cycle; thus, the dye can be measured at any time during the PCR cycling, including the hybridization step. In contrast, molecular beacons and FRET hybridization probes typically involve the measurement of fluorescence during the hybridization step.

Molecular Beacons

Molecular beacons are another real-time PCR approach which may be used to identify the presence or absence of a polymorphism of the present invention. Molecular beacons are oligonucleotide probes that are labeled with a fluorescent dye (typically on the 5' end) and a quencher dye (typically on the 3' end). A region at each end of the molecular beacon probe is designed to be complementary to itself, so at low temperatures the ends anneal, creating a hairpin structure. This hairpin structure positions the two dyes in close proximity, quenching the fluorescence from the reporter dye. The central region of the probe is designed to be complementary to a region of a PCR amplification product. At higher temperatures, both the PCR amplification product and probe are single stranded. As the temperature of the PCR is lowered, the central region of the molecular beacon probe may bind to the PCR product and force the separation of the fluorescent reporter dye from the quenching dye. Without the quencher dye in close proximity, a light signal from the reporter dye can be detected. If no PCR amplification product is available for binding, the probe can re-anneal to itself, bringing the reporter dye and quencher dye into close proximity, thus preventing fluorescent signal.

Two or more molecular beacon probes with different reporter dyes may be used for detecting single nucleotide polymorphisms. For example, a first molecular beacon designed with a first reporter dye may be used to indicate the presence of a SNP and a second molecular beacon designed with a second reporter dye may be used to indicate the presence of the corresponding wild-type sequence; in this way, different signals from the first and/or second reporter dyes may be used to determine if a subject is heterozygous for a SNP, homozygous for a SNP, or homozygous wild-type at the corresponding DNA region. By selection of appropriate PCR temperatures and/or extension of the probe length, a molecular beacons may bind to a target PCR product when a nucleotide polymorphism is present but at a slight cost of reduced specificity. Molecular beacons advantageously do not require thermocycling, so temperature optimization of the PCR is simplified.

FRET Hybridization Probes

FRET hybridization probes, also referred to as LightCycler® probes, may also be used to detect a polymorphism of the present invention. FRET hybridization probes typically comprise two DNA probes designed to anneal next to each other in a head-to-tail configuration on the PCR product. Typically, the upstream probe has a fluorescent dye on the 3' end and the downstream probe has an acceptor dye on the 5' end. If both probes anneal to the target PCR product, fluorescence from the 3' dye can be absorbed by the adjacent acceptor dye on the 5' end of the second probe. As a result, the second dye is excited and can emit light at a third wavelength, which may be detected. If the two dyes do not come into close proximity in the absence of sufficient complimentary DNA, then FRET does not occur between the two dyes. The 3' end of the second (downstream) probe may be phosphorylated to prevent it from being used as a primer by Taq during PCR amplification. The two probes may encompass a region of 40 to 50 DNA base pairs.

FRET hybridization probe technology permits melting curve analysis of the amplification product. If the temperature is slowly raised, probes annealing to the target PCR product will be reduced and the FRET signal will be lost. The temperature at which half the FRET signal is lost is referred to as the melting temperature of the probe system. A single nucleotide polymorphism in the target DNA under a hybridization FRET probe will still generate a signal, but the melting curve will display a lower Tm. The lowered Tm can indicate the presence of a specific polymorphism. The target PCR product is detected and the altered Tm informs the user there is a difference in the sequence being detected Like molecular beacons, there is not a specific thermocycling temperature requirement for FRET hybridization probes. Like molecular beacons, FRET hybridization probes have the advantage of being recycled or conserved during PCR temperature cycling, and a fluorescent signal does not accumulate as PCR product accumulates after each PCR cycle.

Primer Extension

Primer extension is another technique which may be used according to the present invention. A primer and no more than three NTPs may be combined with a polymerase and the target sequence, which serves as a template for amplification. By using less than all four NTPs, it is possible to omit one or more of the polymorphic nucleotides needed for incorporation at the polymorphic site. It is important for the practice of the present invention that the amplification be designed such that the omitted nucleotide(s) is(are) not required between the 3' end of the primer and the target polymorphism. The primer is then extended by a nucleic acid polymerase, in a preferred embodiment by Taq polymerase. If the omitted NTP is required at the polymorphic site, the primer is extended up to the polymorphic site, at which point the polymerization ceases. However, if the omitted NTP is not required at the polymorphic site, the primer will be extended beyond the polymorphic site, creating a longer product. Detection of the extension products is based on, for example, separation by size/length which will thereby reveal which polymorphism is present. For example, U.S. Publ. No. US20040038258, which is hereby incorporated by reference, describes a form of primer extension.

RFLP

Restriction Fragment Length Polymorphism (RFLP) is a technique in which different DNA sequences may be differentiated by analysis of patterns derived from cleavage of that DNA. If two sequences differ in the distance between sites of cleavage of a particular restriction endonuclease, the length of the fragments produced will differ when the DNA is digested with a restriction enzyme. The similarity of the patterns generated can be used to differentiate species (and even strains) from one another.

Restriction endonucleases in turn are the enzymes that cleave DNA molecules at specific nucleotide sequences depending on the particular enzyme used. Enzyme recognition sites are usually 4 to 6 base pairs in length. Generally, the shorter the recognition sequence, the greater the number of fragments generated. If molecules differ in nucleotide sequence, fragments of different sizes may be generated. The fragments can be separated by gel electrophoresis. Restriction enzymes are isolated from a wide variety of bacterial genera and are thought to be part of the cell's defenses against invading bacterial viruses. Use of RFLP and restriction endonucleases in SNP analysis requires that the SNP affect cleavage of at least one restriction enzyme site.

Mass Spectrometry

Mass spectrometry may also be used to detect a polymorphism of the present invention. By exploiting the intrinsic properties of mass and charge, mass spectrometry (MS) can resolved and confidently identified a wide variety of complex compounds. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000). Methods of mass spectroscopy that may be used with the present invention include: ESI, ESI tandem mass spectroscopy (ESI/MS/MS), Secondary ion mass spectroscopy (SIMS), Laser desorption mass spectroscopy (LD-MS), Laser Desorption Laser Photoionization Mass Spectroscopy (LDLPMS), and MALDI-TOF-MS.

Hybridization

There are a variety of ways by which one can assess genetic profiles, and may of these rely on nucleic acid hybridization. Hybridization is defined as the ability of a nucleic acid to selectively form duplex molecules with complementary stretches of DNAs and/or RNAs. Depending on the application envisioned, one would employ varying conditions of hybridization to achieve varying degrees of selectivity of the probe or primers for the target sequence.

Typically, a probe or primer of between 13 and 100 nucleotides, preferably between 17 and 100 nucleotides in length up to 1-2 kilobases or more in length will allow the formation of a duplex molecule that is both stable and selective. Such fragments may be readily prepared, for example, by directly synthesizing the fragment by chemical means or by introducing selected sequences into recombinant vectors for recombinant production.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, lower stringency conditions may be used. Under these conditions, hybridization may occur even though the sequences of the hybridizing strands are not perfectly complementary, but are mismatched at one or more positions.

Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

Kits

The present compositions may be assembled into kits or pharmaceutical systems for use in detecting or diagnosing a gastrointestinal disorder and/or austim spectrum disorder. Materials and reagents required for detecting nucleic acid mutations in a sample may be assembled together in a kit. This generally will comprise a capture reagent, primer, or probe designed to hybridize specifically to, upstream and/or downstream of target nucleotides of the polymorphism of interest. The primer or probe may be labeled with a radioisotope, a fluorophore, a chromophore, a dye, an enzyme, or TOF carrier. Also included may be enzymes suitable for amplifying nucleic acids, including various polymerases (reverse transcriptase, Taq, etc.), dNTPs/rNTPs and buffers (e.g., 10×buffer=100 mM Tris-HCl (pH 8.3), and 500 mM KCl) to provide the necessary reaction mixture for amplification. One or more of the deoxynucleotides may be labeled with a radioisotope, a fluorophore, a chromophore, a dye, or an enzyme. Such kits may also include enzymes and other reagents suitable for detection of specific nucleic acids or amplification products. The kits of the invention may also comprise associated instructions for using the agents of the invention. Additionally, one or more agents for treating a gastrointestinal disorder or autism spectrum disorder may be included.

Kits according to this aspect of the invention comprise a carrier means, such as a box, carton, tube or the like, having in close confinement therein one or more container means, such as vials, tubes, ampoules, bottles and the like. The container means of the kits will generally include at least one vial, test tube, flask, bottle, or other container means, into which a component may be placed, and preferably, suitably aliquoted. Where there is more than one component in the kit, the kit also will generally contain additional containers into which the additional components may be separately placed. However, various combinations of components may be comprised in a container. The kits of the present invention also will typically include a means for packaging the component containers in close confinement for commercial sale. Such packaging may include injection or blow-molded plastic containers into which the desired component containers are retained.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Identification of Unique Gene Expression Profile in Children with Regressive Autism Spectrum Disorder (ASD) and Ileocolitis The studies presented herein utilize transcriptome profiling of gastrointestinal mucosal biopsy tissue from $ASD^{IC}$ children and three non-ASD control groups (Crohn's disease, ulcerative colitis, and histologically normal) to examine the presence of a gene expression profile unique to the $ASD^{IC}$ group. Comparison of differentially expressed transcripts between the groups demonstrated that non-pathologic (normal) tissue segregated almost completely from inflamed tissue in all cases. Gene expression profiles in intestinal biopsy tissue from patients with Crohn's disease, ulcerative colitis, and $ASD^{IC}$, while having significant overlap with each other, also showed distinctive features for each group. Taken together, these results presented herein demonstrate that $ASD^{IC}$ children have a gastrointestinal mucosal molecular profile that overlaps significantly with known inflammatory bowel disease (IBD), yet has distinctive features that further supports the presence of an ASD-associated IBD variant, or, alternatively, a prodromal phase of typical inflammatory bowel disease. Whole transcriptome analysis of biopsy tissue from $ASD^{IC}$ (ASD with ileocolitis) and non-ASD IBD (Crohn's disease and ulcerative colitis) patients has provided molecular evidence for an overlapping, yet unique, IBD-like condition in ASD children. To evaluate the molecular mechanisms that underlie inflammation in the large and small intestines of $ASD^{IC}$ children, the genes and biological pathways that are differentially regulated between inflamed and non-inflamed ileocolonic tissue were examined.

The materials and methods used in these experiments are now described.

Subjects

The study presented herein examined gene expression in histologically inflamed colonic and ileal intestinal mucosal tissue from consecutive GI symptomatic children undergoing diagnostic ileocolonoscopy and biopsy for active GI symptoms. Subjects included children with a diagnosis of ASD ($ASD^{IC}$; n=25, mean age 5.08±2.06 years; 23 male and 2 female) and three typically-developing groups including: (1) children who underwent diagnostic ileocolonoscopy for chronic GI symptoms in which no histopathology was found (n=15, mean age 12.2±3.07 years; 6 male and 9 female), (2) children with a diagnosis of Crohn's disease (n=8, mean age 12.97±3.07 years; 3 male and 5 female), (3) and children with a diagnosis of ulcerative colitis (n=5, mean age 12.0±4.0 years; all female).

Case Selection and Biopsy Procurement

Most patients of the ASD-GI group (Table 1 and Table 7) were referred for gastrointestinal evaluation by their primary care provider though some patients were self-referred. All were patients of a single pediatric gastroenterologist (AK) and were selected based upon a history of normal development for at least 12 months followed by developmental regression and onset of GI symptoms (Table 2). For all individuals in this group, this was their first diagnostic ileocolonoscopy and no patients were taking medication thought to alter the histologic appearance of the GI mucosa. All cases had ileal lymphoid nodular hyperplasia (LNH) and all had histologically-confirmed colitis and/or ileitis in at least one of 8-10 collected and archived ileocolonic biopsies. 25 consecutive patients meeting these criteria were selected.

All patients were assigned a diagnosis of ASD (Autism, Asperger's or PDD-NOS; 16 had a diagnosis of autism; 9 had a diagnosis of autism spectrum disorder) by one or more practitioners from the following specialties: pediatric neurology, developmental pediatrics, pediatric psychiatry or psychology. Of the twenty five ASD individuals included in this study, there were 22 Caucasians, one black, one Caucasian/Hispanic, and one whose ethnicity was not recorded.

A detailed history of GI symptoms was documented (Table 2). Patients who met clinical criteria for diagnostic ileocolonoscopy and biopsy and whose parents agreed to participate in this IRB-approved study (Copernicus Group Independent Review Board) were provided with a study description and informed written consent from the next of kin, carers or guardians on the behalf of all the minors/children participants involved in all studies was obtained.

Specimens were obtained using a standard disposable forceps biopsy device, in accordance with routine diagnostic biopsy protocol. Immediately upon procurement of biopsy tissue, a specimen from each of seven anatomic locations (from the terminal ileum to rectum) was processed for paraffin embedding and subsequent routine histopathology. Biopsies for microarray analysis were obtained from the divided mucosal specimen at each anatomic location. These tissues were placed directly into RNA stabilizer solution, RNAlater (Qiagen Inc; Valecia, Calif.) and stored at −80° C. prior to processing.

Control Biopsy Procurement

Prospective controls (Table 1 and Table 8), included children who presented with symptoms and laboratory testing suggesting possible intestinal disease (Crohn's disease, ulcerative colitis, celiac disease) or food allergy. Non-IBD Control subjects were further defined as those who, following colonoscopy, were without endoscopic or pathologic findings explaining their symptoms. However, the initial indication for colonoscopy was presence of unexplained GI symptoms ranging from abdominal pain, diarrhea, malnutrition, blood observed in the stools, etc. Failure to diagnose the etiology of observed symptoms by endoscopy was subsequently followed by clinical reassessment or additional diagnostic testing.

No concerns regarding developmental delays for any participant in any of the control groups were reported by parents, relatives, caretakers, or teachers and none were noted by physicians.

For the twenty eight children in the control groups there were 22 Caucasian, 1 black, and 1 Hispanic. The ethnicities for the other four were not recorded. Tissues for microarray analysis were collected, processed and stored in identical fashion to those from children with ASD. Informed written consent from the next of kin, carers or guardians on the behalf of all the minors/children participants involved in all studies was obtained.

All specimens (cases and controls) were collected and stored in identical fashion (e.g. pinch cold biopsy forceps, immediate placement in RNA later, and freezing at −80° degrees within 24-48 hours), cases were collected at a single location with controls collected at a second location, and both cases and controls were collected using identical specimen collection protocols as outlined in the SOP submissions to the respective IRB's.

TABLE 1

Characteristics of Study Population

| Case Status | measure | Age (years) | Gender M (%) | F (%) |
|---|---|---|---|---|
| ASD with GI symptoms (n = 25) | Mean (SD) Range | 5.08 (2.06) 1.81-0.9 | 23 (92) | 2 (8) |
| non-ASD with Crohn's disease (n = 8) | Mean (SD) Range | 12.97 (3.07) 4-17 | 3 (37) | 5 (67) |

TABLE 1-continued

Characteristics of Study Population

| Case Status | measure | Age (years) | Gender M (%) | Gender F (%) |
|---|---|---|---|---|
| non-ASD with ulcerative colitis (n = 5) | Mean (SD) Range | 12.0 (3.98) 5-15 | 0 (0) | 5 (100) |
| non-ASD—no IBD diagnosis (n = 15) | Mean (SD) Range | 12.2 (3.07) 6-16 | 6 (40) | 9 (60) |

TABLE 2

Gastrointestinal Symptoms in ASD Study Population

| GI Symptom | $ASD^{IC}$ N = 25 n (%) |
|---|---|
| Chronic diarrhea | 18 (72) |
| Abdominal pain | 14 (56) |
| Abdominal distention/gas | 3 (12) |
| Constipation | 3 (12) |
| Diarrhea alternating with constipation | 2 (8) |
| Vomiting | 2 (8) |

Microarray and Data Analysis

Sample Preparation

Total RNA was isolated from mucosal biopsies that had been stored in RNAlater by sonicating the tissue in the presence of TriReagent (Molecular Research Center, Inc., Cincinnati, Ohio) according to the method of Chomcynski and Sacchi (Chomcynski and Sacchi (1987) Anal Biochem 162(1): 156-159). Total RNA was purified using RNeasy Minelute Plus columns (includes an on-column DNAse step) and reagents (Qiagen, Valencia, Calif.) and eluted in nuclease-free water. RNA concentration and quality were determined using a Nanodrop ND-1000 (Nanodrop Technologies, Wilmington, Del.) and Agilent Bioanalyzer, respectively. A single biopsy specimen was typically 3-5 mg of tissue and yielded from 3-10 µg of high quality (e.g. RIN≥7) total RNA.

Microarray

For microarray hybridizations, 500 ng of total RNA from each biopsy was labeled with fluorescent dye (Cy3; Amersham Biosciences Corp, Piscataway, N.J.) using the Low RNA Input Linear Amplification Labeling kit (Agilent Technologies, Palo Alto, Calif.) following the manufacturer's protocol. The amount and quality of the fluorescently labeled cRNA was assessed using a NanoDrop ND-1000 spectrophotometer and an Agilent Bioanalyzer. According to manufacturer's specifications, 1.6 µg of Cy3-labeled cRNA was hybridized to the Agilent Human Whole Genome Oligo Microarray (Agilent Technologies, Inc., Palo Alto, Calif.) for 17 hrs, prior to washing and scanning. Data were extracted from scanned images using Agilent's Feature Extraction Software (Agilent Technologies, Inc., Palo Alto, Calif.)

Quantitative Real-time PCR (qPCR)

Quantitative real-time PCR was used to validate representative transcripts that showed differential expression, by microarray, from terminal ileum and colonic tissue in $ASD^{IC}$ tissues compared to control tissues. For these assays, six paired RNAs (one TI and one colonic RNA sample) from $ASD^{IC}$ cases and six paired RNAs from the control individuals were used as representative samples for PCR. Twelve differentially-expressed transcripts were chosen from the 178 DETs listed in Table 9 for validation. Of these twelve transcripts, six (IL2RA, TXLNG2P, RPS4Y1, RPS4Y2, ZFY, and IGF2BP1) were up-regulated in both the TI and colon, five (AMPD1, SCGB2A1, INSL5, NTS, and KCTD4) were down-regulated in both tissues and one transcript (TNFRSF12A) was up-regulated in colonic tissue and down-regulated in the terminal ileum.

The qPCR analyses were performed using the $RT^2$ SYBR Green ROX qPCR Mastermix (Qiagen) with cDNA samples generated from 0.5 ug total RNA using $RT^2$ First Strand Kit (Qiagen) following the manufacturer's instructions. Custom-made 96 well plates (SABiosciences) contained primers for each of the 12 transcripts of interest, two reference genes (ACTB and GAPDH) and two positive controls, aligned in two adjacent columns on the plate. Each 96 well plate was used to assay six individual cDNAs. Following the qPCR run on a StepOnePlus Real-time PCR system (Applied Biosystems), using the custom plate manufacuturer's recommendations, the raw data from each 96 well plate (4 total) were uploaded to the SABiosciences web-based analysis software to determine differential expression parameters (fold change and p value). The software automatically performs all $\Delta\Delta C_t$ based fold-change calculations from the uploaded raw quantification cycle data. The results from these assays, compared to the corresponding microarray results, can be found in Table 6.

Data Analysis

Pair-wise Analysis to Determine Differentially-expressed Transcripts.

Gene expression data were uploaded into the GeneSifter® Analysis Edition (Geospiza, Inc, Seattle, Wash.) software suite. For all pair-wise comparisons the data were first normalized by global normalization using the median intensity and transformed (log base 2) prior to running the non-parametric Wilcoxon Rank-Sum Test, with Benjamini-Hochberg FDR correction, to generate lists of differentially-expressed transcripts (DETs). The fold-change threshold was set at 2.0 and the data were considered significant if the comparison had an associated log ratio adjusted p-value less than 0.05. The list of differentially-expressed transcripts from a given pair-wise comparison was then imported into Ingenuity Pathway Analysis software for determination of biologically relevant functional categories and canonical pathway involvement. This analysis was performed for each of the eight individual pair-wise comparisons.

Principal Component Analysis.

In order to determine the overall similarity between samples, ratio data were subjected to Principal Components Analysis (PCA) and two-way agglomerative cluster analysis using Ward's minimum variance as heuristic criteria and Pearson correlation as the distance metric for experiments, and average linkage as heuristic and Pearson correlation distance as the distance metric for genes to determine the overall similarity between samples and within groups (Rosetta Resolver version 7.2.2.0). No filtering was applied to the profile level data prior to PCA.

Hierarchial Clustering Analysis.

The non-parametric Kruskal-Wallis test, with Benjamini and Hochberg FDR correction, was performed on all 102 microarray datasets (@ fold change ≥2; adjusted p ≤0.001) representing the eight experimental groups (four conditions; two tissues).

Expression Quantitative Trait Loci Analysis.

Gene expression data (using Agilent whole genome microarrays) and SNP data (generated at 23&me on custom Illumina SNP chips) from 64 individuals were used for the eQTL analyses. Standard quality control was completed for association studies (e.g., SNP call rate, Hardy-Weinberg Equilibrium). Analyses were computed separately for colon and terminal illium samples and by ASD$^{IC}$ (ASD with ileocolitis), CD and UC disease groups. For each transcript and tissue type, a genome-wide association analysis was computed using linear regression on single nucleotide polymorphism (SNP) cis (within 50 kb) to the probe's gene. In this eQTL analysis, the SNP's genotype and the first principal components were regressed onto log$_2$ expression for the transcript. Given the modest sample size, only the dominant genetic model was computed. A fixed effect meta-analysis and the corresponding test for heterogeneity of effects were computed across disease groups. Significance of an eQTL effect was measured as the magnitude of the p-value conditional on an expression fold change of at least 1.5.

The results of experiments are now described.
Demographics of Cases and Controls
ASD$^{IC}$ Samples.

A total of twenty five consecutive ASD$^{IC}$ cases (6 autism; 19 autism spectrum disorder) with histopathologic findings of ileitis, colitis, or both were selected for inclusion in this study (Table 1 and Table 7). All cases underwent routine diagnostic ileocolonoscopy for chronic gastrointestinal symptoms (Table 2) and demonstrated the histologic presence of ileal infiltrates (ileitis), colonic infiltrates (colitis) or both (ileocolitis). For twenty one of the individuals, both a terminal ileum and a colonic biopsy specimen provided usable RNA. For the remaining four individuals, only a terminal ileum specimen was processed and assayed because the RNA from the corresponding colonic specimens was of insufficient quantity and/or quality.

Non-ASD Samples (1) Crohn's Disease. Eight children with a diagnosis of Crohn's disease were included in this study; seven with active disease (Table 1 and Table 8). For each individual, a terminal ileum and a colonic biopsy was processed. Pathologic cellular infiltrates were present in either the ileum, colon, or at both locations.

(2) Ulcerative Colitis. Five children with a diagnosis of ulcerative colitis were included in this study; four with active disease (Table 1 and Table 8). For each individual, a terminal ileum and a colonic biopsy was processed. Pathologic cellular infiltrates were present in the colon or, in some cases, both ileum and colon.

(3) Controls. Fifteen children without identifiable gastrointestinal pathology were included in this study (Table 1 and Table 8). For each control individual, a terminal ileum and a colonic biopsy specimen was processed. No pathologic infiltrates were seen in either the ileum or colon.

Principal Component Analysis (PCA)

Figure 2:
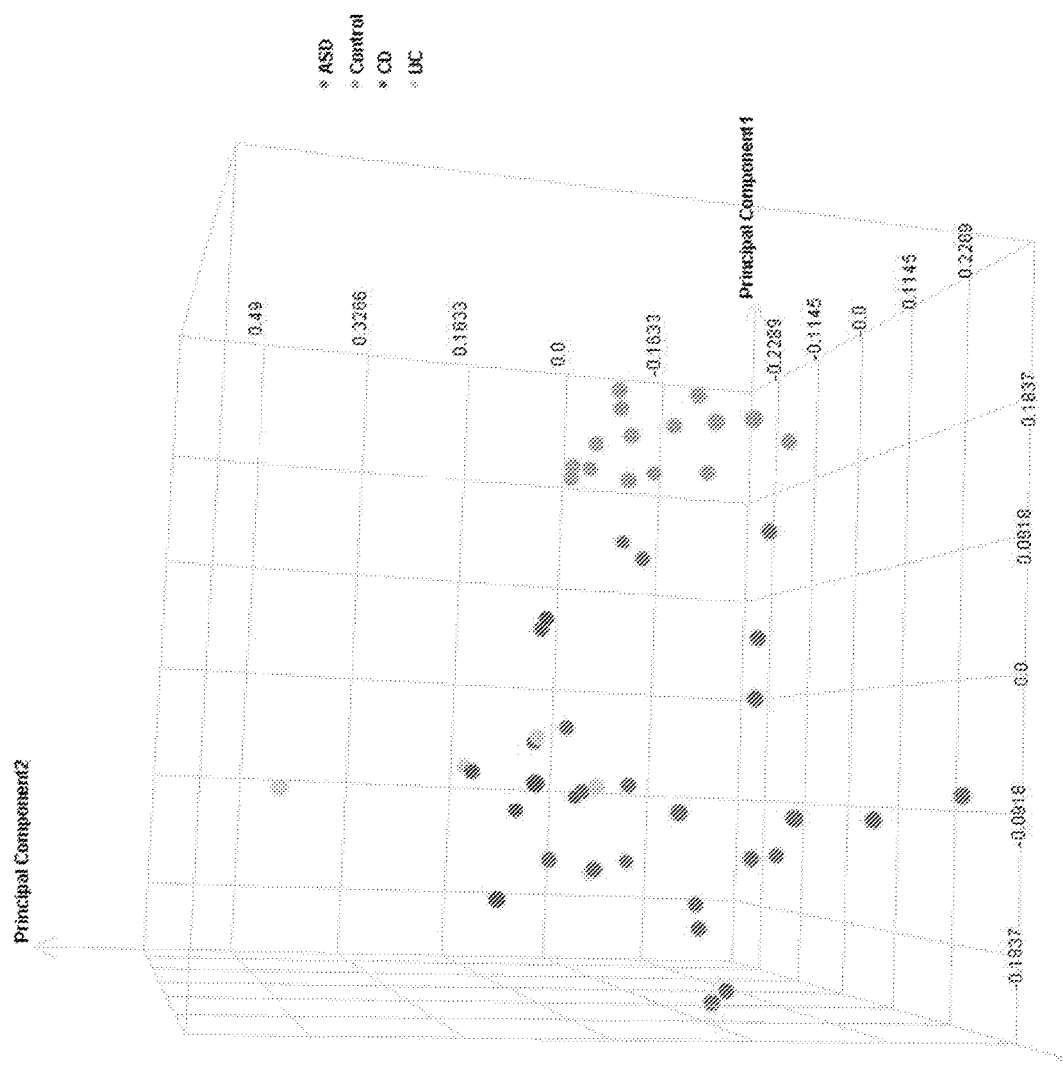
FIG. 2 is an image depicting a Principal Component Analysis (PCA) scatterplot representing 49 individual microarray datasets from colonic tissues. Each circle represents the cumulative gene expression profile for an individual sample. Samples with similar profiles cluster together in the three-dimensional space.
Figure 3:
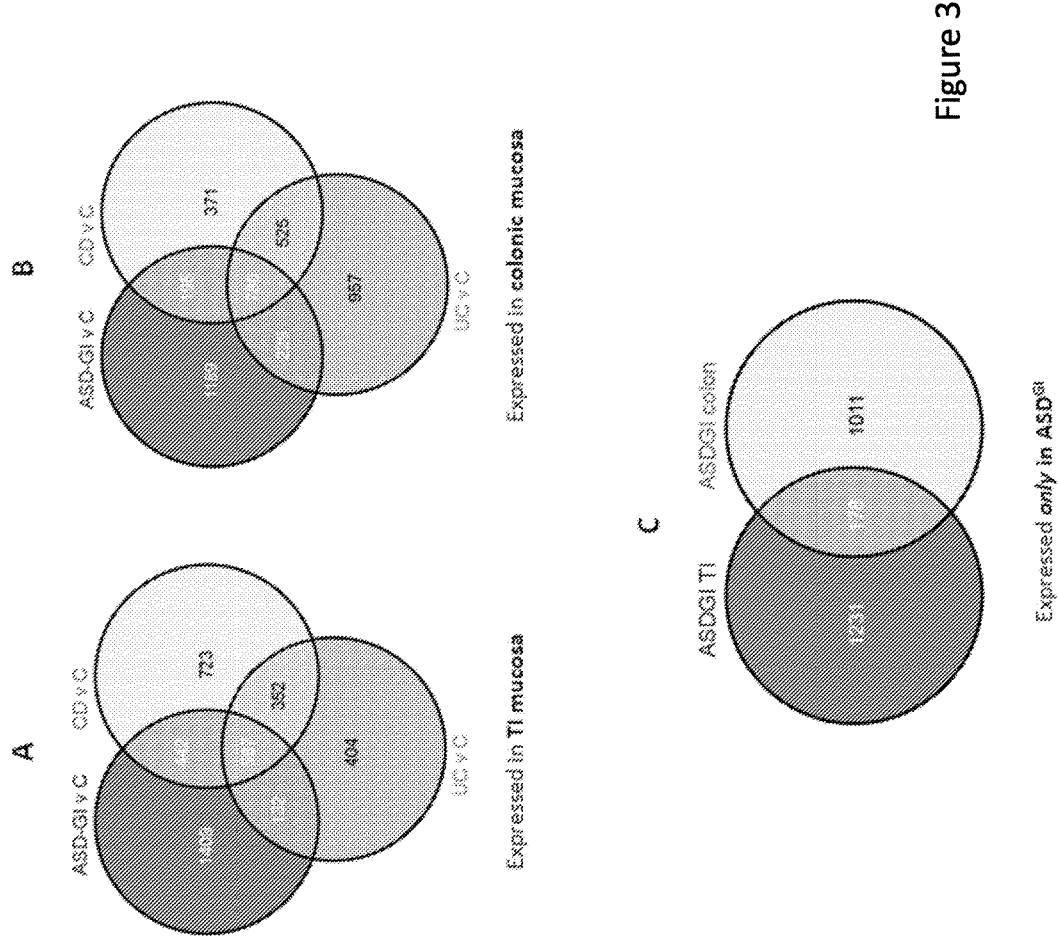
FIGS. 3A-3C are images depicting the overlapping unique ASD$^{IC}$ gene expression from TI and colon. Pair-wise comparisons were performed between each of the disease groups (ASD$^{IC}$, CD and UC) and the control (non-histopathologic tissue) samples.

PCA and unsupervised hierarchical clustering of the sample level data were performed to determine similarity among biological replicates. No filtering was applied to the profile level data prior to PCA. This analysis supports disease state as the largest source of variation in these samples (FIGS. 1 and 2). In an additional analysis of the entire dataset, applying Kruskal-Wallis (@ fold change ≥2; adjusted p≤0.001) with Benjamini and Hochberg FDR, hierarchial clustering demonstrated that: (1) groups of samples cluster by tissue type and, (2) known IBD samples (CD and UC) are more similar to each other than to ASD$^{IC}$ samples (FIG. 3).

Ileal Mucosa Gene Expression Profiles

In the PCA that illustrates findings in ideal mucosa, the 15 control children without identifiable GI disease cluster tightly together while gene expression profiles from inflamed mucosa representing the other groups show broader distribution (variability). Gene expression profiles for the ASD$^{IC}$ samples show the broadest variability in the PCA, suggestive of some potential subgroup(s) (FIG. 1). Significant overlap between ASD$^{IC}$ and both Crohn's disease and ulcerative colitis is evident. Gene expression profiles for the Crohn's disease mucosa showed relatively tight clustering that was completely non-overlapping with the histologically normal control group (FIG. 1). Interestingly, the majority (80%) of ileal mucosa profiles from children with ulcerative colitis segregated with the profiles for Crohn's disease ileal mucosa.

Colonic Mucosa Gene Expression Profiles

In the PCA displaying gene expression profiles in colonic mucosa (FIG. 2), the 15 control children without identifiable GI disease once again cluster relatively tightly together, and apart from all other samples, while inflamed mucosa representing the other groups show broader distribution (variation). Gene expression profiles for the ASD$^{IC}$ samples show the broadest distribution in the PCA (FIG. 2). There is some degree of overlap with Crohn's disease and ulcerative colitis but no such overlap with non-inflamed controls. Once again, gene expression profiles for the Crohn's disease mucosa were quite distinct from those in the histologically normal control group. Likewise, for ulcerative colitis mucosa there was considerable overlap with the Crohn's disease profiles but no overlap with histologically normal controls.

Pairwise Comparisons

Following a determination of the overlap between DETs for three comparisons in each of the two tissues (six comparisons total), each list of DETs unique to a particular comparison (e.g. ASD$^{IC}$ versus control in the terminal ileum) was imported into Ingenuity Pathway Analysis software (IPA: Ingenuity Systems, Inc.; Redwood City, Calif.) for gene ontology and pathway analysis. The IPA analysis returns significant (p≤0.05) 'hits' for each of several categories related to gene networks, biological functions, canonical pathways, and transcription factors. The results that follow focus on findings in the Diseases and Disorders (Table 3) and Physiological System Development and Function (Table 4) categories, and the Top Canonical Pathway (Table 5) involvement category.

TABLE 3

Summary for IPA Diseases and Disorders Catagory

| | ileum | | | colon | | |
|---|---|---|---|---|---|---|
| Diseases and Disorders | ASD$^{IC}$ | CD | UC | ASD$^{IC}$ | CD | UC |
| gastrointestinal disease | * | | | * | * | |
| inflammatory bowel disease | * | | | | * | |
| colitis | * | | | | | |
| inflammatory response | * | * | | | | |
| inflammation of organ | * | | | | | |
| antibody response | * | | | | | |
| activation of leukocytes | * | | | | | |
| dermatologic diseases and conditions | | * | | | | |
| exanthem | | * | | | | |
| psoriasis | | * | | | | |
| inflammatory disease | | * | | | * | |
| rheumatic disease | | * | * | | * | |
| dermatitis | | * | | | | |
| cell movement of phagocytes | | * | | | | |
| migration of neutrophils | | * | | | | |
| cardiovascular disease | | | * | | | |
| vascular disease | | | * | | | |
| connective tissue disorder | | | * | | | |
| digestive organ tumor | | | | | * | |

TABLE 3-continued

Summary for IPA Diseases and Disorders Catagory

| Diseases and Disorders | ileum | | | colon | | |
|---|---|---|---|---|---|---|
| | ASD$^{IC}$ | CD | UC | ASD$^{IC}$ | CD | UC |
| gastrointestinal tract cancer | | | | * | | |
| colon tumor | | | | * | | |
| neurological disease | | | | * | | |
| schizophrenia | | | | * | | |
| hyperactive disorder | | | | * | | |
| necrotizing enterocolitis | | | | | * | |
| immunological disease | | | | | * | |
| autoimmune disease | | | | | * | |
| hypersensitive reaction | | | | | * | |
| Sjogren's syndrome | | | | | * | |
| organismal injury and abnormalities | | | | | | * |
| pain | | | | | | * |
| bleeding | | | | | | * |
| nutritional disease | | | | | | * |
| eating disorder | | | | | | * |
| iron deficiency | | | | | | * |
| failure to thrive | | | | | | * |

TABLE 4

Summary for IPA Physiologic System Development and Function Category

| Physiologic System Development and Function | ileum | | | colon | | |
|---|---|---|---|---|---|---|
| | ASD$^{IC}$ | CD | UC | ASD$^{IC}$ | CD | UC |
| humoral immune response | * | | | | | |
| production of antibody | * | | | | | |
| function of B lymphocytes | * | | | | | |
| tissue morphology | * | | | | | |
| quantity of leukocytes | * | | | | | |
| quantity of blood cells | * | | | | | |
| quantity of lymph node cells | * | | | | | |
| morphology of epithelial cells | * | | | | | |
| digestive system development and function | * | | | | | |
| morphology of digestive system | * | | | | | |
| development of gastrointestinal tract | * | | | | | |
| immune cell trafficking | | * | | | | |
| cell movement of myeloid cells | | * | | | | |
| homing of leukocytes | | * | | | | |
| cell-mediated immune response | | * | | | * | |
| T cell migration | | * | | | | |
| development of Th17 cells | | * | | | | |
| nervous system development and function | | | * | | | |
| long-term potentiation | | | * | | | |
| morphology of nervous tissue | | | * | | | |
| cardiovascular system development and function | | | * | | | |
| migration of endothelial cell line | | | * | | | |
| angiogenesis | | | * | | | |
| behavior | | | | * | | |
| social behavior | | | | * | | |
| learning | | | | * | | |
| cognition | | | | * | | |
| organ development | | | | * | | |
| growth of intestinal villus | | | | * | | |
| development of brain | | | | * | | |
| lymphoid tissue structure and development | | | | | * | |
| tissue development | | | | | | * |
| development of epidermis | | | | | | * |

TABLE 5

Summary for IPA Canonical Pathways Catagory

| Canonical Pathways | ileum | | | colon | | |
|---|---|---|---|---|---|---|
| | ASD$^{IC}$ | CD | UC | ASD$^{IC}$ | CD | UC |
| O-Glycan Biosynthesis | * | | | | | |
| Propanoate Metabolism | * | | | | | |
| Arginine and Proline Metabolism | * | | | | | |
| Alanine and Aspartate Metabolism | * | | | | | |
| Differential Regulation of Cytokine Production in Intestinal Epithelial Cells by IL-17A and IL17F | | * | | | | |
| Differential Regulation of Cytokine Production in Macrophages and T Helper Cells by IL-17A and IL-17F | | * | | | | |
| LXR/RXR Activation | | * | | | | |
| Antigen Presentation Pathway | | | * | | * | |
| Cysteine Metabolism | | | * | | | |
| B Cell Development | | | * | | | |
| Atherosclerosis Signaling | | | | * | * | * |
| Factors Promoting Cardiogenesis in Vertebrates | | | | * | | |
| Mitotic Roles of Polo-Like Kinase | | | | * | | |
| T Helper Cell Differentiation | | | | | * | |
| Interferon Signaling | | | | | * | |
| Il-12 Signaling and Production in Macrophages | | | | | * | |
| cAMP-mediated signaling | | | | | | * |
| G-Protein Coupled Receptor Signaling | | | | | | * |

Differentially-Expressed Transcripts in Ileal Mucosa

I. Gene Expression Profiles in Ileal Mucosa from ASD$^{IC}$ Children Compared with Histologically Normal Ileal Mucosa from Typically Developing Controls.

Figure 4:
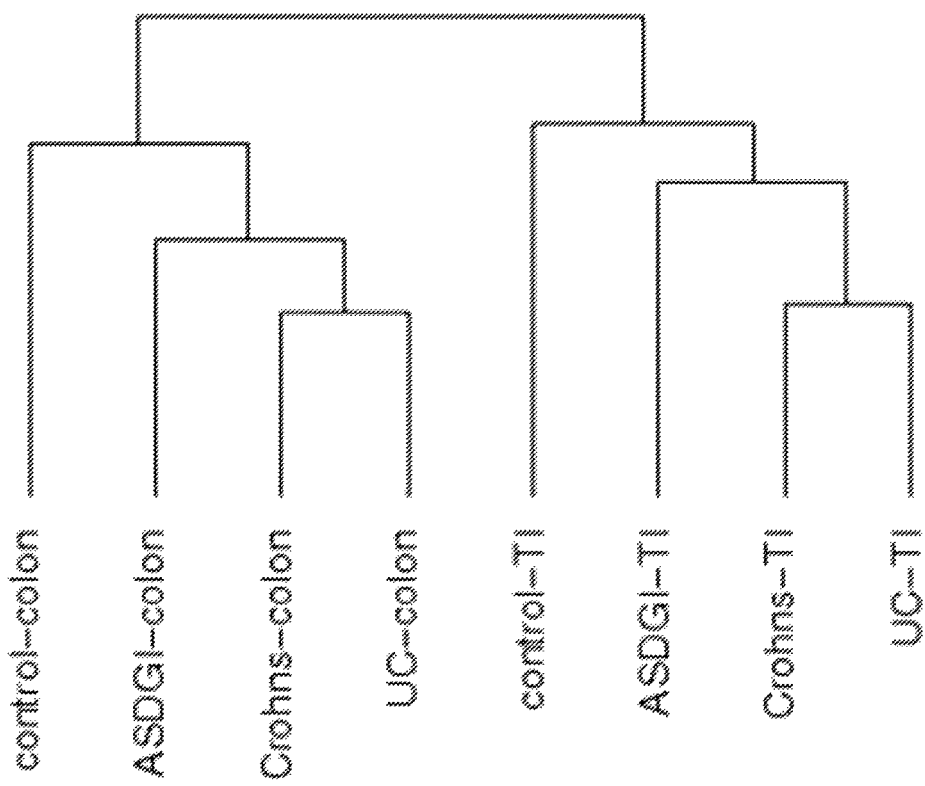
FIG. 4 is an image depicting the Hierarchial clustering analysis of all samples in all groups. A Kruskal-Wallis test with Benjamini and Hochberg FDR resulted in 5008 DETs (a fold change ≥2; adjusted p≤0.001) between the 8 groups.

Pair-wise analyses between ileal mucosa from ASD$^{IC}$ and non-inflamed control samples resulted in 2570 DETs. Seventy-three percent (1862) of DET's were down-regulated in the ASD group compared with the control group while the remainder were up-regulated (@ fold change ≥2; adjusted p≤0.05). Of these, there were 1409 DETs unique to ASD-GI samples (FIG. 4A). Using a less stringent analysis, 4017 DETs were obtained having differential expression in ileal mucosa from ASD$^{IC}$ and non-inflamed control samples, of which 66% were down-regulated in the ASD group For this list of 1409 DETs unique to the ASD$^{IC}$ ileal biopsies, the Diseases and Disorders category returned highly significant associations with: (1) gastrointestinal disease[217 genes; $p=1.4 \times 10^{-08}$] including inflammatory bowel disease[42 genes; $p=3.2 \times 10^{-05}$] and colitis [25 genes; $p=8.8 \times 10^{-04}$] and (2) inflammatory response [198 genes; $p=3.8 \times 10^{-07}$] including inflammation of organ[88 genes; $p=3.8 \times 10^{-7}$], antibody response [27 genes; $p=2.1 \times 10^{-6}$] and activation of leukocytes [74 genes; $p=4.9 \times 10^{-6}$].

The Physiological System Development and Function category returned highly significant associations with: (1) humoral immune response [91 genes; $p=2.2 \times 10^{-10}$] including production of antibody [52 genes; $p=9.9 \times 10^{-10}$] and function of B lymphocytes [23 genes; $p=4.4 \times 10^{-09}$]; (2) tissue morphology [208 genes; $p=1.8 \times 10^{-09}$] including quantity of leukocytes [109 genes; $p=1.7 \times 10^{-8}$], quantity of blood cells [113 genes; $p=1.4 \times 10^{-6}$], quantity of lymph node cells [8 genes; $p=3.6 \times 10^{-4}$] and morphology of epithelial cells [22 genes; $p=4.5 \times 10^{-4}$]; and (3) digestive system development and function[87 genes; $p=3.1 \times 10^{-09}$] including morphology of digestive system [78 genes; $p=3.1 \times 10^{-9}$] and development of gastrointestinal tract [15 genes; $p=1.8 \times 10^{-3}$].

Significant numbers of DETs were found in a number of canonical pathways including: O-Glycan Biosynthesis [9 genes; p=1.3×10$^{-4}$], Propanoate Metabolism [11 genes; p=4.6×10$^{-4}$], Arginine and Proline Metabolism [13 genes; p=4.8×10$^{-4}$], and Alanine and Aspartate Metabolism [9 genes; p=5.0×10$^{-4}$].

II. Gene Expression Profiles in Ileal Mucosa from Typically Developing Children with Crohn's Disease Compared with Histologically Normal Ileal Mucosa from Typically Developing Controls.

Pair-wise analyses between inflamed ileal mucosa from Crohn's Disease samples and non-inflamed control mucosa resulted in 2104 DETs, 71% (1494) which were down-regulated in Crohn's disease mucosa compared to 29% of the DETs that were up-regulated (a fold change ≥2; adjusted p≤0.05). Of these, there were 723 DETs unique to CD samples (FIG. 3A).

The Ingenuity profile for Crohn's disease mucosa versus control mucosa for these unique DETs returned functional category results almost entirely related to inflammation and immune response. The Diseases and Disorders category returned a highly a significant association with: (1) dematologic diseases and conditions [58 genes; p=1.8×10$^{-7}$] including exanthem [15 genes; p=1.8×10$^{-07}$] and psoriasis [38 genes; p=3.0×10$^{-06}$]; (2) inflammatory disease[82 genes; p=2.6×10$^{-7}$] including rheumatic disease[62 genes; p=2.6×10$^{-07}$] and dermatitis [24 genes; p=9.7×10$^{-05}$]; and (3) inflammatory response [69 genes; p=4.8×10$^{-7}$] including cell movement of phagocytes [34 genes; p=1.5×10$^{-06}$] and migration of neutrophils [12 genes; p=8.5×10$^{-06}$].

The Physiological System Development and Function category returned highly significant associations with: (1) immune cell trafficking [57 genes; p=4.8×10$^{-7}$] including cell movement of myeloid cells [33 genes; p=2.7×10$^{-06}$] and homing of leukocytes [24 genes; p=3.8×10$^{-5}$] and (2) cell-mediated immune response [18 genes; p =7.7×10$^{-05}$] including T cell migration[15 genes; p=4.3×10$^{-4}$] and development of Th17 cells [4 genes; p=6.9×10$^{-4}$].

Significant numbers of DETs were found in several canonical pathways: Differential Regulation of Cytokine Production in Intestinal Epithelial Cells by IL-17A and IL17F [7 genes; p=9.7×10$^{-7}$], Differential Regulation of Cytokine Production in Macrophages and T Helper Cells by IL-17A and IL-17F [5 genes; p=6.1×10$^{-5}$], and LXR/RXR Activation[11 genes; p=2.2×10$^{-4}$].

III. Gene Expression Profiles in Ileal Mucosa from Typically Developing Children with Ulcerative Colitis Compared with Histologically Normal Ileal Mucosa from Typically Developing Controls.

Pair-wise analyses between inflamed ideal mucosa from ulcerative colitis samples and non-inflamed control mucosa resulted in 1475 DETs, 59% (870) which were down-regulated in ulcerative colitis mucosa compared controls while the remainder were up-regulated (a fold change ≥2; adjusted p≤0.05). Of these, there were 404 DETs unique to UC samples (FIG. 3A).

For this analysis, in spite of the comparatively small number of DETs, the Diseases and Disorders category returned a highly significant associations with: (1) cardiovascular disease[25 genes; p=7.2×10$^{-5}$] including vascular disease[21 genes; p=5.4×10$^{-4}$] and (2) connective tissue disorders [32 genes; p=6.5×10$^{-4}$] including rheumatic disease[29 genes; p=1.9×10$^{-03}$].

The Physiological System Development and Function category returned highly significant associations with: (1) nervous system development and function[32 genes; p=6.4×10$^{-4}$] including long-term potentiation[10 genes; p=6.4×10$^{-04}$] and morphology of nervous tissue [16 genes; p=7.5×10$^{-3}$] and (2) cardiovascular system development and function[21 genes; p=7.4×10$^{-04}$] including migration of endothelial cell line[5 genes; p=7.4×10$^{-4}$] and angiogenesis [16 genes; p=1.8×10$^{-2}$].

Significant numbers of DETs were found in a number of canonical pathways including: Antigen Presentation Pathway [5 genes; p=1×10$^{-4}$], Cysteine Metabolism [4 genes; p=4.7×10$^{-3}$] and B Cell Development [3 genes; p=7.8×10$^{-3}$].

Differentially-Expressed Transcripts in Colonic Mucosa

I. Gene Expression Profiles in Inflamed Colonic Mucosa from ASD$^{IC}$ Children Compared with Non-Inflamed Colonic Mucosa from Typically Developing Controls.

Pair-wise analyses between inflamed colonic mucosa from ASD$^{IC}$ children and non-inflamed control mucosa resulted in 2393 DETs, 69% (1657) that were down-regulated in ASD$^{IC}$ mucosa compared with those in the control group, while the remainder were up-regulated (a fold change ≥2; adjusted p≤0.05). Of these, there were 1189 DETs unique to ASD-GI samples (FIG. 3B). Using a less stringent analysis, 2796 DETs were obtained having differential expression in colonic mucosa from ASD$^{IC}$ and non-inflamed control samples, of which 61% were up-regulated in the ASD group.

For this comparison, the Diseases and Disorders category returned highly significant associations with: (1) gastrointestinal disease[152 genes; p=2.4×10$^{-10}$] including digestive organ tumor [147 genes; p=2.4×10$^{-10}$], gastrointestinal tract cancer [106 genes; p=6.5×10$^{-10}$] and colon tumor [56 genes; p=5.6×10$^{-9}$] and (2) neurological disease[152 genes; p=9.3×10$^{-5}$] including schizophrenia [50 genes; p=9.3×10$^{-5}$] and hyperactive disorder [16 genes; p=8.8×10$^{-4}$].

The Physiological System Development and Function category returned highly significant associations with: (1) behavior [98 genes; p=4.3×10$^{-7}$] including social behavior [8 genes; p=5.3×10$^{-3}$], learning [23 genes; p=1.4×10$^{-2}$] and cognition[25 genes; p=1.5×10$^{-02}$] and (2) organ development [98 genes; p=6.1×10$^{-06}$] including growth of intestinal villus [2 genes; p=2.5×10$^{-3}$] and development of brain [37 genes; p=1.4×10$^{-2}$].

Significant numbers of DETs were found in a number of canonical pathways including: Atherosclerosis Signaling [14 genes; p=2.4×10$^{-3}$], Factors Promoting Cardiogenesis in Vertebrates [11 genes; p=4.1×10$^{-3}$] and Mitotic Roles of Polo-Like Kinase[9 genes; p=5.5×10$^{-3}$].

II. Gene Expression Profiles in Inflamed Colonic Mucosa from Typically Developing Children with Crohn's Disease Compared with Non-inflamed Colonic Mucosa from Typically Developing Controls.

Pair-wise analyses between inflamed colonic mucosa from Crohn's disease samples and non-inflamed colonic mucosa from typically developing children resulted in 1871 DETs, 35% (657) which were down-regulated in Crohn's disease mucosa compared with those in the control group while the rest were up-regulated (a fold change ≥2; adjusted p≤0.05). Of these, there were 371 DETs unique to CD samples (FIG. 3B).

The Ingenuity profile for Crohn's disease mucosa versus control colonic mucosa resulted in three highly relevant Diseases and Disorders categories that returned several significant associations: (1) inflammatory disease[58 genes; p=1.6×10$^{-10}$] including rheumatic disease[47 genes; p=1.6×10$^{-10}$] and necrotizing enterocolitis [2 genes; p=2.6×10$^{-3}$]; (2) immunological disease[53 genes; p=3.5×10$^{-9}$] including autoimmune disease[47 genes; p=3.5×10$^{-9}$] and hypersensitive reaction[15 genes; p=2.8×10$^{-3}$] and (3) gastrointestinal disease[40 genes; p=1.7×10$^{-7}$] including Sjogren's syndrome [11 genes; p=1.7×10$^{-7}$] and inflammatory bowel disease[11 genes; p=8.4×10$^{-3}$].

The Physiological System Development and Function category returned highly significant associations with: (1) cell-mediated immune response [21 genes; p=9.3×10$^{-6}$] and (2) lymphoid tissue structure and development [28 genes; p=9.3×10$^{-06}$].

Significant numbers of DETs are highlighted from five canonical pathways: Antigen Presentation Pathway [5 genes; p=1.3×10$^{-4}$], T Helper Cell Differentiation[6 genes; p=3.3×10$^{-4}$], Interferon Signaling [4 genes; p=1.1×10$^{-3}$], Atherosclerosis Signaling [7 genes; p=1.1×10$^{-3}$] and 11-12 Signaling and Production in Macrophages [7 genes; p=2.2×10$^{-3}$].

III. Gene Expression Profiles in Inflamed Colonic Mucosa from Typically Developing Children with Ulcerative Colitis Compared with Non-inflamed Colonic Mucosa from Typically Developing Controls.

Pair-wise analyses between inflamed colonic mucosa from the ulcerative colitis group and non-inflamed mucosa from the control group resulted in 2491 DETs of which 32% (795) were down-regulated transcripts in the ulcerative colitis group compared with controls (a fold change ≥2; adjusted p≤0.05) and the majority 68% (1696) were up-regulated. Of these DETs, there were 957 unique to ulcerative colitis samples (FIG. 3B).

For this comparison, the Diseases and Disorders category returned a highly a significant association with: (1) organismal injury and abnormalities [52 genes; p=5×10$^{-7}$] including pain [23 genes; p=5×10$^{-7}$] and bleeding [25 genes; p=8.8×10$^{-4}$] and (2) nutritional disease[53 genes; p=5×10$^{-6}$] including eating disorder [10 genes; p=3.1×10$^{-4}$], iron deficiency [2 genes; p=4.9×10$^{-3}$] and failure to thrive [2 genes; p=1.2×10$^{-2}$].

The Physiological System Development and Function category returned a highly significant association with tissue development [94 genes; p=4.1×10$^{-7}$] including development of epidermis [14 genes; p=6.2×10$^{-04}$].

Significant numbers of DETs were found in a number of canonical pathways including: cAMP-mediated signaling [17 genes; p=1.7×10$^{-4}$], G-Protein Coupled Receptor Signaling [27 genes; p=2.1×10$^{-3}$], and Atherosclerosis Signaling [10 genes; p=2.4×10$^{-3}$].

Comparison of DETs in ASD$^{IC}$ Sub-groups

I. Differential Gene Expression Unique to Tissues from ASD$^{IC}$ Children

In order to identify DETs that uniquely occur in the ASD$^{IC}$ tissues, pair-wise comparisons were made between control samples and ASD$^{IC}$ samples in each of the two tissues (terminal ileum and colon; FIGS. 3A&B). In these two groups of pair-wise comparisons there were 1409 DETs unique to the ASD$^{IC}$ cases in terminal ileum and 1189 DETs unique to the colon in ASD$^{IC}$ cases. The overlap between these two sets of DETs yielded 178 transcripts that are exclusively differentially-expressed in both TI and colonic tissues derived from the ASD$^{IC}$ population, but not the others (FIG. 3C). When these 178 DETs (Table 9) were analyzed using the Ingenuity Pathway Software, three of the top associated biological functions were inflammatory disease (7 genes; p=3.1×10$^3$), endocrine system development and function (17 genes; p=6.6×10$^{-5}$), and digestive system development and function (13 genes; p=2×10$^{-4}$). Significant numbers of DETs were found in a number of metabolic and signaling pathways including: Granzyme A Signaling [2 genes; p=1×10$^{-2}$], Atherscrelosis Signaling [4 genes; p=1.6×10$^{-2}$], Valine, Leucine and Isoleucine Degradation[3 genes; p=1.6×10$^{-2}$] and Clathrin-mediated Endocytosis Signaling [5 genes; p=1.7×10$^{-2}$].

Using the less stringent analyses, of the 4017 DETs identified in the terminal ileum and 2796 identified in the colon samples, 972 DETs were common between the two tissues. These shared DETs were significantly associated with cancer, inflammatory response and, interestingly, neurological disease A subset of transcripts determined by microarray analysis to be differentially expressed in both TI and colonic tissues in ASG$^{IC}$ cases was verified by quantitative real-time PCR. Twelve transcripts were chosen from the 178 DETs listed in Table 9 for analysis by PCR. Of these twelve, six transcripts were up-regulated in both the TI and colon, five transcripts were down-regulated in both tissues, and one transcript was up-regulated in colonic tissue but down-regulated in the terminal ileum. Analysis by quantitative PCR confirmed the microarray findings for 11 of 12 transcripts in each of the two tissues (Table 6).

TABLE 6

Comparison of microarray results with qPCR results from 12 representative transcripts differentially-regulated in both terminal ileum and colon, exclusively in ASD$^{IC}$ samples.

| Gene Symbol | Gene Identifier | microarray data | | | PCR data | | |
|---|---|---|---|---|---|---|---|
| | | Ratio | Direction | adj. p-value | Ratio | Direction | p-value |
| TERMINAL ILEUM | | | | | | | |
| AMPD1 | NM_000036 | 3.7 | ↓ | 4.47E−07 | 4.29 | ↓ | 4.92E−01 |
| IL2RA | NM_000417 | 2.63 | ↑ | 2.94E−06 | 4.93 | ↑ | 4.10E−05 |
| TXLNG2P | NM_001005852 | 8.5 | ↑ | 2.62E−02 | 97.67 | ↑↑ | 3.41E−04 |
| RPS4Y1 | NM_001008 | 43.3 | ↑↑ | 5.89E−03 | 132.11 | ↑↑ | 1.46E−03 |
| RPS4Y2 | NM_001039567 | 29.65 | ↑↑ | 8.41E−03 | 25.71 | ↑↑ | 1.02E−03 |
| SCGB2A1 | NM_002407 | 5.25 | ↓ | 3.64E−07 | 5.9 | ↓ | 2.50E−01 |
| ZFY | NM_003411 | 5.08 | ↑ | 3.27E−02 | 1.42 | ↑ | 1.77E−02 |
| INSL5 | NM_005478 | 2.2 | ↓ | 2.25E−02 | 1.27 | ↓ | 5.27E−01 |
| NTS | NM_006183 | 5.71 | ↓ | 7.84E−07 | 10.33 | ↓↓ | 3.27E−02 |
| IGF2BP1 | NM_006546 | 4.28 | ↑ | 1.65E−06 | 7.13 | ↑ | 1.22E−01 |
| TNFRSF12A | NM_016639 | 2.07 | ↓ | 4.58E−05 | 1.83 | ↓ | 9.00E−03 |
| KCTD4 | NM_198404 | 3.58 | ↓ | 5.23E−06 | 1.96 | ↑ | 2.13E−01 |

TABLE 6-continued

Comparison of microarray results with qPCR results from 12 representative transcripts differentially-regulated in both terminal ileum and colon, exclusively in $ASD^{IC}$ samples.

| Gene Symbol | Gene Identifier | microarray data | | | PCR data | | |
|---|---|---|---|---|---|---|---|
| | | Ratio | Direction | adj. p-value | Ratio | Direction | p-value |
| COLONIC BIOPSY | | | | | | | |
| AMPD1 | NM_000036 | 3.85 | ↓ | 1.62E-04 | 14.07 | ↓↓ | 4.37E-04 |
| IL2RA | NM_000417 | 4.58 | ↑ | 9.01E-07 | 3.45 | ↑ | 1.11E-02 |
| TXLNG2P | NM_001005852 | 9.71 | ↑ | 2.60E-02 | 97.35 | ↑↑ | 4.18E-02 |
| RPS4Y1 | NM_001008 | 56.76 | ↑↑ | 1.68E-02 | 121.79 | ↑↑ | 1.38E-01 |
| RPS4Y2 | NM_001039567 | 42.65 | ↑↑ | 1.84E-02 | 16.05 | ↑↑ | 3.13E-02 |
| SCGB2A1 | NM_002407 | 4.34 | ↓ | 6.32E-07 | 6.4 | ↓ | 3.18E-03 |
| ZFY | NM_003411 | 5.45 | ↑ | 1.84E-02 | 1.02 | ↓ | 6.56E-01 |
| INSL5 | NM_005478 | 28.45 | ↓↓ | 2.15E-04 | 14.17 | ↓↓ | 2.20E-01 |
| NTS | NM_006183 | 2.05 | ↓ | 2.66E-03 | 16.92 | ↓↓ | 5.63E-04 |
| IGF2BP1 | NM_006546 | 14.18 | ↑↑ | 1.29E-07 | 7.55 | ↑ | 1.03E-01 |
| TNFRSF12A | NM_016639 | 2.94 | ↑ | 2.11E-03 | 2.88 | ↑ | 9.65E-02 |
| KCTD4 | NM_198404 | 4.1 | ↓ | 2.46E-05 | 1.4 | ↓ | 2.20E-01 |

II. Gene Expression Profiles in Ileal Mucosa from ASD Children with LNH Only (17) Compared with Ileal Mucosa from ASD Children with LNH & Ileitis (8)

Of the children in the $ASD^{IC}$ group, all 25 had LNH while 8 of the 25 also had histologically confirmed ileitis. A comparison was performed in order to examine the additional effect of ileal inflammation on gene expression within the $ASD^{IC}$ group. Comparison of results from pair-wise analyses between $ASD^{IC}$ cases with LNH only versus $ASD^{IC}$ cases with LNH and ileitis resulted in 41 DETs that were unique to the LNH+ileitis group (Table 10). When this list of DETs was analyzed in IPA, the Diseases and Disorders category returned a highly a significant association with inflammatory response [16 genes; $p=5.8 \times 10^{-13}$], immunologic disease [17 genes; $p=1.9 \times 10^{-11}$] and dermatological diseases and conditions [16 genes; $p=2.9 \times 10^{-11}$]. The Physiological System Development and Function category returned a highly significant association with immune cell trafficking [13 genes; $p=3.4 \times 10^{-14}$]. Significant numbers of DETs were highlighted in three key pathways: IL-17 Signaling [3 genes; $p=3.1 \times 10^{-4}$], Il-17A Signaling in Gastric Cells [2 genes; $p=9.6 \times 10^{-4}$] and Role of IL-17A in Arthritis [2 genes; $p=4.4 \times 10^{-3}$].

Molecular Characterization of Inflamed GI Biopsy Tissue

In the analyses of the gene expression profiles of $ASD^{IC}$ tissue and their comparison to three non-ASD control groups presented herein, the molecular characterization of inflamed GI biopsy tissue, previously described only in terms of its histologic and immunohistochemical staining properties, has been, for the first time, provided. Employing differential expression and principle component analysis methodologies it has been herein found that: (a) DETs in $ASD^{IC}$ distinguish this group from non-inflamed controls (i.e. non-specific ileocolonic cellular infiltrate in GI symptomatic ASD children is not "normal"), (b) previously published data that demonstrate characteristic DETs in Crohn's disease and ulcerative colitis, as compared to non-inflamed controls, was reaffirmed and, (c) DETs in $ASD^{IC}$ cases are distinct from both IBD and non-inflamed typically developing controls, though overlap exists between $ASD^{IC}$ and IBD gene expression profiles.

An analysis of the three groups consisting of inflamed GI tissue demonstrated extensive intergroup DET overlap in both ileum and colon when compared to non-inflamed controls. The finding of overlap between the Crohn's disease and ulcerative colitis samples was expected based on previous comparisons of gene expression in mucosal tissue in IBD patients, however the new findings presented here of DET overlap between $ASD^{IC}$ and IBD (Crohn's and ulcerative colitis) provides further evidence in support of a novel ASD-associated enterocolitis. Perhaps more importantly, although there were significant numbers of overlapping DETs in each of the two tissues for $ASD^{IC}$, Crohn's disease, and ulcerative colitis, the pair-wise comparisons between $ASD^{IC}$ and controls resulted in the largest number of DETs unique to those comparisons (1409 in terminal ileum; 1189 in colonic tissue). This provides important molecular evidence that, while similar to Crohn's disease and ulcerative colitis, gene expression profiles in $ASD^{IC}$ tissue remain significantly distinct not only from those of known IBD conditions but also from those of non-inflamed tissue as well. It remains to be seen specifically how these molecular (gene expression) differences in Crohn's disease, ulcerative colitis and $ASD^{IC}$ are expressed phenotypically.

In the terminal ileum mucosal tissue, gene expression analysis revealed that for $ASD^{IC}$, Crohn's disease, and ulcerative colitis, a large majority of DETs (59-73%) were down-regulated compared to non-inflamed control tissue. In the pair-wise comparisons for Crohn's disease and for $ASD^{IC}$, the disease categories that were most significantly represented were: (a) gastrointestinal disease and, (b) inflammatory response/disease. In contrast, for ulcerative colitis, disease categories including cardiovascular disease and connective tissue disorders were significantly represented. All of the categories identified within these comparisons were accompanied by highly significant p values, indicating that in all of these tissues there was a strong association with a pathologic gastrointestinal phenotype. The pathway involvement, while demonstrating some common themes across comparisons (e.g. cell signaling and metabolic processes), was somewhat different for each of the three conditions, highlighting variation in the associated underlying biology that distinguishes them.

In the colonic mucosal tissue, gene expression analysis revealed that in CD and UC a majority of the DETs were up-regulated (65-68%) whereas in $ASD^{IC}$ the majority of transcripts (69%) were down-regulated. The disease categories significantly represented in $ASD^{IC}$ were gastrointestinal disease and neurologic disease. In the CD samples there was a highly significant association with gene ontologies representing inflammatory disease and immunological disease, as well as gastrointestinal disease. The ulcerative colitis profiles were correlated strongly with organismal injury and nutritional disease. The pathways that showed significant involvement in each of the three comparisons again varied somewhat but, as in the terminal ileal mucosa, generally involved cell signaling and metabolic processes.

All of the terminal ileal $ASD^{IC}$ samples displayed lymphoid nodular hyperplasia (LNH) but only a portion of them also had inflammation (ileitis). To determine the additional impact of ileitis on gene expression in $ASD^{IC}$ cases, an analysis was performed between $ASD^{IC}$ TI samples with (8) and without (17) ileitis. Interestingly, the disease categories most significantly represented by these DETs unique to the LNH+ileitis samples were inflammatory response, immunologic disease and dermatological diseases and conditions. The biological pathways that were found to be significantly regulated in this comparison are largely involved in immune-mediated signaling. This data set adds the additional significant observations that: (1) although the absence of cellular infiltrate does not preclude the presence of a unique molecular signature, the presence of cellular infiltrate (i.e. ileitis) results in further refining the discerning nature of the signature to specific DETs and, (2) the presence of LNH without ileitis in the $ASD^{IC}$ group is associated with unique DETs, suggesting that LNH in the setting of ASD, chronic gastrointestinal symptoms, and cellular infiltrate (anywhere in the bowel) is part of the disease process.

In summary, the overall gene expression patterns from comparisons of inflamed and non-inflamed tissue in CD, UC and $ASD^{IC}$ exhibited unique DETs as well as some degree of overlap. The dendogram in FIG. 4 displays these relationships for each of the two tissues. The Kruskal-Wallis test results lend further support to the findings in the individual pair-wise comparisons; i.e. DETs in IBD conditions (CD and UC) are more similar to each other than to $ASD^{IC}$, and all three groups are more similar to each other than to the non-inflamed controls.

Several aspects of the data are reassuring from a methodological perspective: first, the relatively tight clustering of gene expression profiles from the typically developing non-inflamed group depicted in the PCA for both ileal and colonic mucosa—a clustering that excluded the great majority of those with mucosal inflammation and, second, aberrant gene expression profiles in IBD cases that are in accord with independent reports from other groups (Wu et al. (2007) Inflamm Bowel Dis 13(7): 807-821; Galamb et al. (2006) World J Gastroenterol 12(43): 6998-7006; Costello et al. (2005) PLoS Med 2(8): e199; Lawrance et al. (2001) Hum Mol Genet 10(5): 445-456). Abnormal gene expression in $ASD^{IC}$ tissues is consistent with previous reports of cellular and structural changes within the mucosa (Gonzalez et al. (2005) Arch Venez Pueric Pediat 69: 19-25; Krigsman et al. (2010) Autism Insights 1: 1-11; Torrente et al. (2004) Am J Gastroenterol 4: 598-605; Balzola et al. (2005) Am J Gastroenterol 100: 979-981; Furlano et al. (2001) J Pediatr 38: 366-372) accompanied by pro-inflammatory bias in mucosal CD3+ lymphocyte cytokine profiles (Ashwood et al. (2004) J Clin Immunol 24: 664-673; Ashwood and Wakefield AJ. (2006) J Neuroimmunol 173: 126-134), and a more recent report of abnormal mucosal mRNA profiles in other ASD children who, while suffering GI symptoms, did not appear to have associated mucosal inflammation (Williams et al. (2011) PLoS One 6(9): e24585. Epub 2011 Sep. 16). In the only published study that reports gene expression results in ileal mucosal tissue derived from $ASD^{IC}$ cases compared to controls, Williams et al measured the mRNA levels of three disaccharidases (SI, MGAM and LCT), two glucose transporters (SGLT1 and GLUT2), an enterocyte marker (villin), and a master transcriptional regulator in the intestine (CDX2) (Williams et al. (2011) PLoS One 6(9): e24585). With the exception of villin mRNA (no change), all other transcripts were significantly down-regulated in $ASD^{IC}$ samples compared to controls. Moreover, the ileal expression of the master regulator, CDX2, was a significant predictor of mRNA expression of the three disaccharidases and two transport molecules in $ASD^{IC}$ and $Control^{IC}$ children, based on linear regression models. Data presented herein correlate well with these findings. In the present study, expression of CDX2 was significantly down-regulated in the $ASD^{IC}$ ileum (2.1 fold) as were 2 of the three enzymes (SI and MGAM), both transporters, and villin. These interesting findings may broaden the GI disease repertoire in ASD to include not only mucosal inflammation, as defined by abnormal cellular infiltrate seen during routine light microscopy, but also molecular abnormalities occurring in the absence of obvious light microscopic changes.

Additional factors known to influence human intestinal mucosal gene expression include, but are not limited to, age, gender, ethnicity, prescription medications, diet, and dietary supplements. The variety of diets, medications, and nutritional supplements in the ASD-GI group is depicted in Table 7. For the most part ASD-GI children were on a diet that restricted ingestion of both gluten and casein, and in some instances also soy, whereas individuals in the control groups were not on restrictive diets. In addition, food auto-restriction, a common feature in autism, serves to further limit the variety of foods to which the bowel mucosa is exposed and could potentially impact mucosal gene expression. None of the $ASD^{IC}$ cases in this study were receiving medications known to impact inflammatory processes of the intestinal mucosa for at least four weeks prior to obtaining the biopsies. This includes NSAIDS, H2 blockers, proton pump inhibitors, corticosteroids, antibiotics, probiotics, and immune-suppressants.

The relatively broad distribution of gene expression profiles in the $ASD^{IC}$ samples represented in the PCA analysis may be attributable to a number of different factors. First, while not wishing to be bound by any particular theory, the larger number of cases in this group, relative to the IBD groups, may account for some of this effect. Heterogeneity in the underlying inflammatory process, its severity and location, as well as the average age of individuals within this group, is among the variables that may influence this distribution. While not wishing to be bound by any particular theory, it is also possible that the heterogeneity in gene expression profiles in the $ASD^{IC}$ group is reflective of a disease in various stages of evolution. Therefore it may be speculated that the broad distribution of DETs in $ASD^{IC}$ is reflective of a dynamic process in which the repertoire of DETs is evolving over time, perhaps towards those of other established IBDs.

Taken as a whole, the picture that emerges is one in which GI symptomatic children with ASD in whom cellular infiltrate is present in the ileum and colon have a distinct molecular signature that is consistent with the larger disease categories of gastrointestinal disease, and more specifically, overlaps with Crohn's disease, ulcerative colitis, and autoimmunity, and is associated with digestive system development, function, and pathophysiology, and also with neurological disease. The shared uniquely expressed DETs seen in both the ileum and colon suggest that intestinal mucosal inflammatory infiltrates in the setting of GI symptomatic patients with ASD reflect a single unifying autoimmune process at play in both the small and large bowel.

TABLE 7

Demographic and medical history data for ASD^IC cases.

| | Age | Gender | Diagnosis | Special Diet? | Currently on medications? | Nutritional Supplements at Time of Biopsy |
|---|---|---|---|---|---|---|
| 1 | 3 y 3 m | M | ASD | GFCF | subcutaneous MB-12 | None |
| 2 | 4 y 10 m | M | Autism | GFCF, Soy Free | Miralax | multi minerals and vitamins |
| 3 | 5 y 8 m | M | Autism | GFCF, Corn Free | Bethanechol | Aloe Vera Juice, Cod Liver Oil, Multi-Vitamin, P5P, Vitamin C, Yeast Aid, Candex, Phenol Assist, juice concentrate, Vitamin B-12 |
| 4 | 7 y 8 m | M | Autism | GFCF, SCD | IVIG, IV Secretin | Milk of Magnesia, Mineral Oil, Glutathione |
| 5 | 3 y 7 m | M | Autism | SCD | None | Methylcobalamine, N-acetylcysteine, multivitamins, trimethylglycine, methyl B12, Phenol Assist, Phenol Assist Companion, Fish Oil, Cod Liver Oil, CoQ10, Vitamin E, Vitamin C, Calcium-Magnesium, Glutathione |
| 6 | 2 y 10 m | M | ASD | GFCF | subcutaneous MB12 | DHA Junior, Flax Oil, Vitamin C |
| 7 | 6 y 5 m | M | ASD | GFCF, Soy Free, Dye Free, Sugar Free, SCD | Amitriptyline, Hyacosamine, Allegra | subcutaneous MB12, N-acetylcyteine, cod liver oil, Omega-3, Magnesium |
| 8 | 10 y 11 m | M | ASD | GFCF | Lexapro | None |
| 9 | 4 y 3 m | F | ASD | GFCF/SCD, Nut Free, Honey Free | Humatrope, subcutaneous MB12, DMPS (IV), IV N-acetylcysteine and Folinic acid, IV Secretin (porcine), IVIG | None |
| 10 | 5 y 11 m | M | ASD | Casein Free | Zyrtec | None |
| 11 | 5 y 3 m | M | ASD | SCD | subcutaneous MB12, transdermal DMPS | Cod Liver Oil |
| 12 | 3 y 7 m | M | ASD | Casein Free, Wheat Free, Barley Free, Rye Free | None | multivitamins and minerals, Calcium, Magnesium |
| 13 | 4 y 4 m | F | ASD | GFCF, Soy Free, Dye Free | IVIG, subcutaneous MB12 | wheat dextrin soluble fiber |
| 14 | 3 y 1 m | M | ASD | GFCF | subcutaneous MB12, transdermal DMPS | Multi minerals and vitamins, Cod Liver Oil, Glutathione, Zinc |
| 15 | 8 y 5 m | M | ASD | Casein Free, Soy Free | Clonidine (p.r.n.), Glycolax | None |
| 16 | 7 y 8 m | M | Autism | GFCF | None | None |
| 17 | 5 y 7 m | M | ASD | GFCF | None | None |
| 18 | 3 y 10 m | M | ASD | GFCF | None | None |
| 19 | 3 y 9 m | M | ASD | GFCF, Soy Free | None | subcutaneous MB12, multi vitamins and minerals, Folinic Acid, Amino acids |
| 20 | 4 y 4 m | M | ASD | GFCF | None | None |
| 21 | 3 y 9 m | M | ASD | GFCF, Soy Free, Feingold Diet | subcutaneous MB12 | None |
| 22 | 4 y 1 m | M | ASD | GFCF, SCD | Clonidine (p.r.n.), subcutaneous MB12 | None |
| 23 | 7 y 3 m | M | Autism | High Fiber Diet, GFCF, | None | None |
| 24 | 1 y 10 m | M | ASD/Apraxia | GFCF | None | cod liver oil, multivitamins and minerals, omega-3, amino acids |

TABLE 7-continued

Demographic and medical history data for ASD$^{IC}$ cases.

| | Age | Gender | Diagnosis | Special Diet? | Currently on medications? | Nutritional Supplements at Time of Biopsy |
|---|---|---|---|---|---|---|
| 25 | 5 y 0 m | M | ASD | GFCF, Sugar Free | None | GFCF, Sugar Free |

TABLE 8

Demographic and medical history data for non-ASD controls.

| | Age | Gender | IBD Status | Currently on medications? |
|---|---|---|---|---|
| Control | | | | |
| 1 | 6 | M | | none |
| 2 | 11 | F | | fiber, multivitamins Polyethylene glycol 3350, amitriptyline |
| 3 | 6 | M | | lisdexamfetamine dimesylate, clonidine |
| 4 | 13 | M | | lansoprazole |
| 5 | 15 | M | | montelukast sodium, albuterol, acetaminophen, amitriptyline |
| 6 | 13 | F | | none |
| 7 | 14 | F | | tacrolimus topical, amitriptyline, ondensetron, Hyoscyamine |
| 8 | 11 | F | | none |
| 9 | 11 | F | | Polyethylene glycol 3350, ranitidine, levsin, prevacid, amitriptyline, dicyclomine, impramine |
| 10 | 15 | M | | docusate, Polyethylene glycol 3350, ibuprofen, fluticasone, pantoprazole, metoprolol |
| 11 | 12 | F | | none |
| 12 | 13 | M | | Polyethylene glycol 3350 |
| 13 | 11 | F | | Polyethylene glycol 3350 |
| 14 | 16 | F | | Polyethylene glycol 3350 |
| 15 | 16 | F | | gabapentin, trazamine, hydrocodone, ibuprofen |
| Crohn's disease | | | | |
| 1 | 13 y 10 m | M | active | none |
| 2 | 16 | F | active | none |
| 3 | 15 | F | active | none |
| 4 | 10 | M | inactive | 6-mercaptopurine |
| 5 | 15 | F | active | 6-mercaptopurine, polyethylene glycol 3350, ferrous sulfate, tacrolimus topical |
| 6 | 4 y 9 m | F | active | multivitamin |
| 7 | 17 | M | active | lansoprazole, TPN, prednisone |
| 8 | 12 y 3 m | F | active | none |
| Ulcerative colitis | | | | |
| 1 | 13 | F | active | mesalamine, ferrous sulfate |
| 2 | 5 | F | active | Polyethylene glycol 3350 |
| 3 | 13 | F | active | none |
| 4 | 15 | F | active | chlorpheniramine, dextromethorphan, phenylephrine, ibuprofen, metronidazole |
| 5 | 14 | F | inactive | Polyethylene glycol 3350, mesalamine, lidocaine topical, azathioprine, mesalamine (suppository), VSL#3 (probiotic), prednisone, omeprazole |

TABLE 9

Gene list for 178 transcripts that were differentially-regulated in both terminal ileum and colon, exclusively in ASD$^{IC}$ samples.

| Gene Name | Gene Identifier | Terminal Ilium | | | Colon | | |
|---|---|---|---|---|---|---|---|
| | | Ratio | Direction | adj. p-value | Ratio | Direction | adj. p-value |
| hypothetical protein LOC285505 | AK096792 | 2.35 | Down | 1.70E−04 | 2.33 | Down | 9.07E−04 |
| hypothetical LOC100133306 | AK125136 | 2.23 | Down | 2.60E−05 | 2.52 | Down | 7.63E−05 |
| GTP binding protein 6 (putative) | AK296003 | 2.48 | Down | 1.46E−06 | 2.39 | Down | 9.69E−08 |
| actin, gamma 2, smooth muscle, enteric | AK310215 | 2.2 | Down | 9.80E−04 | 2.87 | Down | 1.48E−03 |
| hypothetical protein LOC643201 | BC034407 | 2.09 | Down | 1.16E−04 | 2.14 | Down | 4.18E−04 |
| protein tyrosine phosphatase, receptor type, F | BC048416 | 2.04 | Down | 1.65E−06 | 2.04 | Down | 3.50E−06 |
| phospholipase B1 | BC065041 | 2.09 | Down | 8.79E−04 | 2.24 | Down | 9.07E−04 |
| aminolevulinate, delta-, dehydratase | NM_000031 | 2.09 | Down | 1.02E−06 | 2.24 | Down | 5.60E−05 |
| adenosine monophosphate deaminase 1 (isoform M) | NM_000036 | 3.7 | Down | 4.47E−07 | 3.85 | Down | 1.62E−04 |
| arylsulfatase E (chondrodysplasia punctata 1) | NM_000047 | 3.08 | Down | 4.58E−05 | 2.15 | Down | 4.12E−03 |

TABLE 9-continued

Gene list for 178 transcripts that were differentially-regulated in both terminal ileum and colon, exclusively in $ASD^{IC}$ samples.

| Gene Name | Gene Identifier | Terminal Ilium | | | Colon | | |
|---|---|---|---|---|---|---|---|
| | | Ratio | Direction | adj. p-value | Ratio | Direction | adj. p-value |
| membrane-spanning 4-domains, subfamily A, member 2 (Fc fragment of IgE, high affinity I, receptor for; beta polypeptide) | NM_000139 | 2.15 | Down | 5.24E−05 | 2.57 | Down | 3.68E−04 |
| transcobalamin II; macrocytic anemia | NM_000355 | 2.34 | Down | 6.00E−05 | 2.58 | Down | 1.04E−05 |
| interleukin 2 receptor, alpha | NM_000417 | 2.63 | Up | 2.94E−06 | 4.58 | Up | 9.01E−07 |
| complement component 8, gamma polypeptide | NM_000606 | 2.13 | Down | 1.70E−04 | 2.01 | Down | 4.18E−04 |
| 4-aminobutyrate aminotransferase | NM_000663 | 2.21 | Down | 1.65E−06 | 2.13 | Down | 5.60E−05 |
| aldehyde dehydrogenase 3 family, memberA1 | NM_000691 | 2.55 | Down | 3.97E−06 | 2.53 | Down | 9.07E−04 |
| cholinergic receptor, muscarinic 1 | NM_000738 | 3.34 | Down | 2.24E−05 | 2.87 | Down | 3.50E−06 |
| similar to growth arrest-specific 6; growth arrest-specific 6 | NM_000820 | 2.17 | Down | 1.16E−06 | 2.12 | Down | 4.08E−05 |
| glycoprotein M6B | NM_001001995 | 2.08 | Down | 1.95E−05 | 2.22 | Down | 6.03E−06 |
| chromosome Y open reading frame 15A | NM_001005852 | 8.5 | Up | 2.62E−02 | 9.71 | Up | 2.60E−02 |
| ribosomal protein S4, Y-linked 1 | NM_001008 | 43.3 | Up | 5.89E−03 | 56.76 | Up | 1.68E−02 |
| legumain | NM_001008530 | 2.54 | Down | 6.05E−06 | 2.38 | Down | 5.45E−04 |
| carboxylesterase 1 (monocyte/macrophage serine esterase 1) | NM_001025195 | 2.36 | Down | 1.89E−06 | 2.01 | Down | 7.63E−05 |
| chymotrypsinogen B2 | NM_001025200 | 2.16 | Down | 1.29E−06 | 2.02 | Down | 9.01E−07 |
| RAB15 effector protein | NM_001029874 | 2.67 | Down | 9.49E−06 | 2.33 | Down | 9.01E−07 |
| ectonucleoside triphosphate diphosphohydrolase 8 | NM_001033113 | 2.6 | Down | 2.19E−06 | 2.78 | Down | 6.32E−07 |
| proopiomelanocortin | NM_001035256 | 2.74 | Up | 1.16E−06 | 2.32 | Up | 2.09E−05 |
| collagen, type XXVIII, alpha 1 | NM_001037763 | 2.26 | Down | 1.71E−05 | 2.04 | Down | 6.21E−04 |
| HEPACAM family member 2 | NM_001039372 | 2.29 | Down | 1.50E−04 | 2.03 | Down | 6.54E−05 |
| ribosomal protein S4, Y-linked 2 | NM_001039567 | 29.65 | Up | 8.41E−03 | 42.65 | Up | 1.84E−02 |
| myosin, heavy chain 11, smooth muscle | NM_001040113 | 2.36 | Down | 1.46E−06 | 2.93 | Down | 4.08E−05 |
| activating transcription factor 3 | NM_001040619 | 2.56 | Down | 1.28E−05 | 2.69 | Down | 2.01E−02 |
| KIAA0895-like | NM_001040715 | 2.67 | Down | 2.60E−05 | 2.16 | Down | 1.41E−04 |
| somatostatin | NM_001048 | 2.07 | Down | 9.00E−05 | 3.62 | Down | 4.78E−04 |
| KIAA1881 | NM_001080400 | 2.1 | Down | 7.89E−04 | 3.72 | Down | 1.87E−04 |
| aldo-keto reductase family 1, member B10 (aldose reductase); aldo-keto reductase family 1, member B10-like | NM_001080538 | 2.21 | Down | 3.99E−04 | 2.11 | Up | 4.08E−05 |
| surfactant protein A2; surfactant protein A2B | NM_001098668 | 3.13 | Down | 4.47E−07 | 2.47 | Down | 1.64E−06 |
| family with sequence similarity 72, member D; family with sequence similarity 72, member A | NM_001123168 | 2.67 | Up | 5.65E−04 | 2.37 | Up | 2.37E−03 |
| actin binding LIM protein family, member 2 | NM_001130083 | 2.08 | Down | 1.22E−03 | 2.22 | Down | 6.03E−06 |
| neural precursor cell expressed, developmentally down-regulated 4-like | NM_001144967 | 2 | Down | 1.95E−05 | 2.01 | Down | 1.64E−06 |
| PP12104 | NM_001162995 | 4.28 | Down | 2.56E−06 | 2.24 | Down | 2.66E−03 |
| mucin 12, cell surface associated; similar to mucin 11 | NM_001164462 | 3.03 | Down | 3.41E−06 | 2.68 | Down | 1.67E−03 |
| Similar to LOC166075 | NM_001168214 | 2.38 | Down | 3.47E−05 | 2.18 | Down | 1.87E−04 |
| chromogranin A (parathyroid secretory protein 1) | NM_001275 | 2.23 | Down | 8.21E−06 | 2.52 | Down | 4.08E−05 |
| actin, alpha 2, smooth muscle, aorta | NM_001613 | 2.35 | Down | 6.05E−06 | 2.72 | Down | 4.08E−05 |
| actin, gamma 2, smooth muscle, enteric | NM_001615 | 2.73 | Down | 1.11E−05 | 2.09 | Down | 2.60E−02 |

TABLE 9-continued

Gene list for 178 transcripts that were differentially-regulated in both terminal ileum and colon, exclusively in ASD$^{IC}$ samples.

| Gene Name | Gene Identifier | Terminal Ilium | | | Colon | | |
|---|---|---|---|---|---|---|---|
| | | Ratio | Direction | adj. p-value | Ratio | Direction | adj. p-value |
| arylsulfatase D | NM_001669 | 2.35 | Down | 3.41E−06 | 2.61 | Down | 2.58E−07 |
| cadherin 3, type 1, P-cadherin (placental) | NM_001793 | 2.76 | Up | 7.02E−06 | 2.02 | Up | 4.12E−03 |
| hyaluronan and proteoglycan link protein 1 | NM_001884 | 4.14 | Down | 1.65E−06 | 2.09 | Down | 1.31E−03 |
| keratin 81 | NM_002281 | 2.74 | Down | 1.46E−06 | 2.39 | Down | 1.04E−05 |
| lysosomal-associated membrane protein 2 | NM_002294 | 2.24 | Down | 4.54E−06 | 2.3 | Down | 3.99E−07 |
| low density lipoprotein receptor-related protein 4 | NM_002334 | 2.7 | Down | 7.02E−06 | 2.27 | Down | 1.41E−04 |
| leukocyte receptor tyrosine kinase | NM_002344 | 2.19 | Down | 3.41E−06 | 2.07 | Down | 6.03E−06 |
| secretoglobin, family 2A, member 1 | NM_002407 | 5.25 | Down | 3.64E−07 | 4.34 | Down | 6.32E−07 |
| NK2 homeobox 2 | NM_002509 | 2.28 | Down | 2.60E−05 | 3.81 | Down | 3.47E−05 |
| neuronal pentraxin I | NM_002522 | 2.19 | Up | 1.52E−02 | 2.27 | Down | 2.96E−03 |
| pyruvate dehydrogenase kinase, isozyme 2 | NM_002611 | 2.18 | Down | 1.48E−05 | 2.12 | Down | 1.11E−06 |
| pleiotrophin | NM_002825 | 2.45 | Down | 2.56E−06 | 2.88 | Down | 8.76E−06 |
| protein tyrosine phosphatase, receptor type, N polypeptide 2 | NM_002847 | 2.4 | Down | 1.46E−06 | 3.13 | Down | 1.61E−07 |
| RAB3B, member RAS oncogene family | NM_002867 | 2.03 | Down | 1.50E−04 | 3.19 | Down | 8.90E−05 |
| chemokine (C-C motif) ligand 17 | NM_002987 | 2.28 | Up | 2.60E−05 | 5.2 | Up | 1.26E−05 |
| chemokine (C—X—C motif) ligand 5 | NM_002994 | 2.19 | Down | 8.41E−03 | 2.04 | Down | 1.87E−04 |
| tryptase alpha/beta 1; tryptase beta 2 | NM_003294 | 2.21 | Down | 2.47E−04 | 2.64 | Down | 1.62E−04 |
| vasoactive intestinal peptide | NM_003381 | 3.35 | Down | 4.54E−06 | 2.89 | Down | 4.18E−04 |
| zinc finger protein, Y-linked | NM_003411 | 5.08 | Up | 3.27E−02 | 5.45 | Up | 1.84E−02 |
| secretogranin II (chromogranin C) | NM_003469 | 2.76 | Down | 9.49E−06 | 2.57 | Down | 4.78E−04 |
| zinc finger protein 282 | NM_003575 | 2.06 | Down | 7.02E−06 | 2.18 | Down | 5.60E−05 |
| breast carcinoma amplified sequence 1 | NM_003657 | 3.45 | Down | 8.74E−07 | 2.2 | Down | 5.02E−06 |
| BAI1-associated protein 3 | NM_003933 | 2.18 | Down | 3.47E−05 | 2.95 | Down | 1.11E−06 |
| retinol binding protein 2, cellular | NM_004164 | 2.24 | Down | 7.86E−05 | 2.58 | Down | 1.02E−03 |
| kinesin family member 1A | NM_004321 | 2.96 | Down | 1.46E−06 | 4.67 | Down | 2.39E−06 |
| tetraspanin 7 | NM_004615 | 2.28 | Down | 1.95E−05 | 2.23 | Down | 5.60E−05 |
| vasoactive intestinal peptide receptor 1 | NM_004624 | 2.71 | Down | 1.65E−06 | 2.29 | Down | 5.02E−06 |
| patatin-like phospholipase domain containing 4 | NM_004650 | 2.73 | Down | 4.93E−07 | 2.78 | Down | 9.69E−08 |
| lysine (K)-specific demethylase 5D | NM_004653 | 3.71 | Up | 2.82E−02 | 2.98 | Up | 1.53E−02 |
| variable charge, Y-linked 1B; variable charge, Y-linked | NM_004679 | 2.19 | Down | 8.21E−06 | 2.31 | Down | 9.01E−07 |
| SPARC-like 1 (hevin) | NM_004684 | 2.11 | Down | 1.46E−06 | 2.21 | Down | 8.90E−05 |
| histone cluster 1, H1d | NM_005320 | 2.12 | Up | 7.02E−06 | 2.55 | Up | 9.01E−07 |
| histone cluster 1, H1a | NM_005325 | 5.33 | Up | 3.01E−05 | 2.83 | Up | 1.27E−02 |
| insulin-like 5 | NM_005478 | 2.2 | Down | 2.25E−02 | 28.45 | Down | 2.15E−04 |
| tetraspanin 2 | NM_005725 | 2.13 | Down | 8.79E−04 | 2.23 | Down | 8.02E−04 |
| T-box 10 | NM_005995 | 2.61 | Down | 1.71E−05 | 2.14 | Down | 1.48E−03 |
| nicotinamide N-methyltransferase | NM_006169 | 2.02 | Up | 5.24E−05 | 2.76 | Up | 6.54E−05 |
| neurotensin | NM_006183 | 5.71 | Down | 7.84E−07 | 2.05 | Down | 2.66E−03 |
| 6-phosphofructo-2-kinase/fructose-2,6-biphosphatase 2 | NM_006212 | 2.25 | Down | 1.46E−06 | 2.08 | Down | 1.11E−06 |
| peripherin | NM_006262 | 2.67 | Down | 7.02E−06 | 2.53 | Down | 2.91E−05 |
| transforming, acidic coiled-coil containing protein 3 | NM_006342 | 2.1 | Up | 5.24E−05 | 2.41 | Up | 6.03E−06 |
| ubiquitin D | NM_006398 | 2.07 | Up | 6.44E−03 | 2.22 | Up | 1.84E−02 |
| melanoma inhibitory activity | NM_006533 | 2.09 | Up | 4.51E−04 | 2.02 | Down | 2.96E−03 |
| insulin-like growth factor 2 mRNA binding protein 1 | NM_006546 | 4.28 | Up | 1.65E−06 | 14.18 | Up | 1.29E−07 |
| WNK lysine deficient protein kinase 2 | NM_006648 | 2.17 | Down | 3.41E−06 | 2.12 | Down | 8.76E−06 |

TABLE 9-continued

Gene list for 178 transcripts that were differentially-regulated in both terminal ileum and colon, exclusively in ASD$^{IC}$ samples.

| Gene Name | Gene Identifier | Terminal Ilium Ratio | Direction | adj. p-value | Colon Ratio | Direction | adj. p-value |
|---|---|---|---|---|---|---|---|
| retinol binding protein 4, plasma | NM_006744 | 2.93 | Down | 5.04E-04 | 2.48 | Down | 1.15E-02 |
| secretagogin, EF-hand calcium binding protein | NM_006998 | 2.54 | Down | 1.71E-05 | 3.69 | Down | 1.49E-05 |
| tryptase delta 1 | NM_012217 | 2.24 | Down | 3.16E-04 | 2.55 | Down | 1.21E-04 |
| PDZ domain containing ring finger 4 | NM_013377 | 2.12 | Up | 1.78E-02 | 2.89 | Down | 1.31E-03 |
| V-set and immunoglobulin domain containing 2 | NM_014312 | 2.47 | Down | 2.24E-05 | 2.88 | Down | 9.01E-07 |
| DNA segment on chr 4 (unique) 234 expressed sequence | NM_014392 | 3.27 | Down | 1.79E-07 | 2.38 | Down | 1.26E-05 |
| LIM homeobox 3 | NM_014564 | 2.68 | Down | 5.43E-07 | 2.18 | Down | 2.39E-06 |
| KIAA0644 gene product | NM_014817 | 3.67 | Down | 3.64E-07 | 4.2 | Down | 1.64E-06 |
| ATPase, Ca++ transporting, type 2C, member 2 | NM_014861 | 2.16 | Down | 1.89E-06 | 2.03 | Down | 8.90E-05 |
| pleckstrin homology domain containing, family A member 6 | NM_014935 | 2.7 | Down | 4.93E-07 | 2.73 | Down | 2.14E-07 |
| pleckstrin homology-like domain, family B, member 1 | NM_015157 | 2.14 | Down | 4.47E-07 | 2.36 | Down | 2.58E-07 |
| vacuolar protein sorting 13 homolog D (*S. cerevisiae*) | NM_015378 | 2.01 | Down | 7.38E-07 | 2.1 | Down | 3.28E-07 |
| sclerostin domain containing 1 | NM_015464 | 2.75 | Down | 3.98E-05 | 2.7 | Down | 6.54E-05 |
| peptidase inhibitor 15 | NM_015886 | 2.62 | Down | 3.70E-03 | 3.83 | Down | 2.96E-03 |
| family with sequence similarity 8, member A1 | NM_016255 | 2.1 | Down | 7.84E-07 | 2.77 | Down | 3.28E-07 |
| prenylcysteine oxidase 1 | NM_016297 | 2.06 | Down | 6.05E-06 | 2.24 | Down | 1.61E-07 |
| protocadherin 12 | NM_016580 | 2.01 | Down | 3.47E-05 | 2.14 | Down | 2.11E-03 |
| tumor necrosis factor receptor superfamily, member 12A | NM_016639 | 2.07 | Down | 4.58E-05 | 2.94 | Up | 2.11E-03 |
| intelectin 1 (galactofuranose binding) | NM_017625 | 3.49 | Down | 4.54E-06 | 2.1 | Down | 3.24E-04 |
| sema domain, immunoglobulin domain (Ig), transmembrane domain (TM) and short cytoplasmic domain, (semaphorin) 4G | NM_017893 | 2.29 | Down | 1.29E-06 | 2.04 | Down | 2.00E-06 |
| transmembrane protein 144 | NM_018342 | 3.08 | Down | 1.16E-06 | 2.11 | Down | 4.36E-08 |
| lysine (K)-specific demethylase 3A | NM_018433 | 2.06 | Down | 7.06E-07 | 2.21 | Down | 6.03E-06 |
| cytokine-like 1 | NM_018659 | 2.03 | Down | 3.98E-05 | 2.83 | Down | 4.08E-05 |
| SV2 related protein homolog (rat) | NM_018711 | 2.32 | Down | 3.98E-05 | 3.26 | Down | 1.64E-06 |
| protocadherin beta 10; protocadherin beta 9 | NM_018930 | 2.72 | Down | 7.02E-06 | 2.44 | Down | 8.02E-04 |
| protocadherin beta 14 | NM_018934 | 2.15 | Down | 6.05E-06 | 2.92 | Down | 9.01E-07 |
| homeobox A10 | NM_018951 | 2.06 | Down | 2.19E-06 | 2 | Down | 1.29E-07 |
| chromosome 15 open reading frame 17 | NM_020447 | 2.01 | Down | 1.50E-04 | 2.78 | Down | 5.02E-06 |
| reticulocalbin 3, EF-hand calcium binding domain | NM_020650 | 2.24 | Down | 6.05E-06 | 2.17 | Down | 4.18E-04 |
| KIAA1324 | NM_020775 | 2.18 | Down | 2.19E-06 | 2.2 | Down | 6.03E-06 |
| left-right determination factor 1 | NM_020997 | 3.42 | Down | 2.24E-05 | 3.26 | Down | 1.49E-05 |
| calcium channel, voltage-dependent, T type, alpha 1H subunit | NM_021098 | 2.01 | Down | 1.65E-06 | 2.13 | Down | 6.21E-04 |
| WAP four-disulfide core domain 1 | NM_021197 | 2.85 | Down | 1.79E-07 | 2.83 | Down | 2.39E-06 |
| egl nine homolog 3 (*C. elegans*) | NM_022073 | 2.79 | Down | 5.23E-06 | 2.41 | Down | 1.04E-04 |
| claspin homolog (*Xenopus laevis*) | NM_022111 | 2.01 | Up | 1.93E-04 | 2.93 | Up | 2.39E-06 |
| chromosome 4 open reading frame 31 | NM_024574 | 2.07 | Down | 1.50E-04 | 2.24 | Down | 2.91E-05 |
| NOL1/NOP2/Sun domain family, member 7 | NM_024677 | 2.15 | Down | 1.71E-05 | 2.01 | Down | 4.18E-06 |
| thrombospondin, type I, domain containing 4 | NM_024817 | 2.42 | Down | 5.23E-06 | 2.37 | Down | 1.64E-06 |
| phospholipase B domain containing 1 | NM_024829 | 2.22 | Down | 2.94E-06 | 2.44 | Down | 2.00E-06 |

TABLE 9-continued

Gene list for 178 transcripts that were differentially-regulated in both terminal ileum and colon, exclusively in ASD$^{IC}$ samples.

| Gene Name | Gene Identifier | Terminal Ilium | | | Colon | | |
|---|---|---|---|---|---|---|---|
| | | Ratio | Direction | adj. p-value | Ratio | Direction | adj. p-value |
| carboxylesterase 3 | NM_024922 | 2.57 | Down | 3.64E−07 | 2.35 | Down | 1.26E−05 |
| phosphatidylinositol glycan anchor biosynthesis, class Z | NM_025163 | 2.64 | Down | 2.47E−04 | 3.45 | Down | 8.76E−06 |
| tripartite motif-containing 45 | NM_025188 | 2.19 | Down | 3.41E−06 | 2.48 | Down | 2.58E−07 |
| coiled-coil domain containing 3 | NM_031455 | 2.15 | Down | 3.41E−06 | 2.27 | Down | 2.83E−04 |
| germ cell associated 2 (haspin) | NM_031965 | 2.24 | Up | 1.95E−05 | 3.97 | Up | 2.58E−07 |
| SLIT and NTRK-like family, member 6 | NM_032229 | 2.98 | Down | 8.74E−07 | 2.78 | Down | 5.60E−05 |
| resistin like beta | NM_032579 | 2.21 | Down | 2.29E−03 | 2.59 | Down | 1.67E−03 |
| CDC14 cell division cycle 14 homolog B (*S. cerevisiae*) | NM_033331 | 2.59 | Down | 4.93E−07 | 2.13 | Down | 1.49E−05 |
| ribosomal protein L39-like | NM_052969 | 2.09 | Up | 3.01E−05 | 2.12 | Up | 1.04E−04 |
| von Willebrand factor A domain containing 5B2 | NM_138345 | 2.11 | Down | 2.56E−06 | 2.58 | Down | 1.62E−04 |
| BCL2-like 14 (apoptosis facilitator) | NM_138722 | 2.84 | Down | 4.47E−07 | 2.37 | Down | 1.29E−07 |
| sperm flagellar 2 | NM_144722 | 2.11 | Down | 2.24E−05 | 2.1 | Down | 5.60E−05 |
| fibronectin type III and ankyrin repeat domains 1 | NM_145235 | 2.21 | Down | 7.84E−07 | 2.34 | Down | 7.72E−07 |
| activin A receptor, type IC | NM_145259 | 2.61 | Down | 5.24E−05 | 2.44 | Down | 3.50E−06 |
| ring finger protein 185 | NM_152267 | 2.09 | Down | 4.93E−07 | 2.03 | Down | 9.01E−07 |
| ubiquitin specific peptidase 54 | NM_152586 | 2.11 | Down | 1.29E−06 | 2.15 | Down | 1.29E−07 |
| tudor domain containing 9 | NM_153046 | 2.52 | Up | 2.19E−04 | 2.27 | Up | 2.60E−02 |
| K+ voltage-gated channel, KQT-like subfamily, member 2 | NM_172109 | 2.22 | Down | 7.06E−07 | 2.07 | Down | 1.11E−06 |
| interleukin 4 induced 1 | NM_172374 | 2.38 | Up | 3.98E−05 | 2.2 | Up | 1.88E−03 |
| chromosome 11 open reading frame 35 | NM_173573 | 2.14 | Down | 2.19E−06 | 2.26 | Down | 2.39E−06 |
| nudix (nucleoside diphosphate linked moiety X)-type motif 14 | NM_177533 | 2.54 | Down | 9.49E−06 | 2.07 | Down | 3.47E−05 |
| chromosome 17 open reading frame 55 | NM_178519 | 2.17 | Down | 4.54E−06 | 2.09 | Down | 4.18E−06 |
| myosin, light chain 9, regulatory | NM_181526 | 2.4 | Down | 3.97E−06 | 2.98 | Down | 6.54E−05 |
| bone morphogenetic protein 8a | NM_181809 | 2.43 | Down | 4.58E−05 | 2.19 | Down | 3.70E−03 |
| family with sequence similarity 131, member C | NM_182623 | 2.43 | Down | 1.29E−06 | 2.36 | Down | 1.64E−06 |
| potassium channel tetramerisation domain containing 4 | NM_198404 | 3.58 | Down | 5.23E−06 | 4.1 | Down | 2.46E−05 |
| G protein-coupled receptor 56 | NM_201525 | 2.13 | Down | 1.16E−06 | 2.05 | Down | 1.36E−06 |
| myoglobin | NM_203377 | 6.33 | Down | 1.89E−06 | 2.02 | Down | 8.58E−03 |
| LRRN4 C-terminal like | NM_203422 | 2.33 | Down | 7.84E−07 | 2.4 | Down | 2.91E−05 |
| synaptotagmin-like 2 | NM_206927 | 2.56 | Down | 7.84E−07 | 2.09 | Down | 7.72E−07 |
| G protein-coupled receptor 153 | NM_207370 | 2.49 | Down | 9.49E−06 | 2.05 | Down | 1.15E−02 |
| family with sequence similarity 72, member D; family with sequence similarity 72, member A | NM_207418 | 2.57 | Up | 1.02E−04 | 2.3 | Up | 1.41E−04 |
| MHC, class II, DR beta 6 (pseudogene) | NR_001298 | 5.1 | Down | 2.52E−03 | 3.97 | Down | 3.70E−03 |
| arginine-fifty homeobox pseudogene 2 | NR_002222 | 2.11 | Down | 2.94E−06 | 2.07 | Down | 2.66E−03 |
| small nucleolar RNA, H/ACA box 28 | NR_002964 | 2.31 | Down | 1.50E−04 | 2.69 | Down | 1.87E−04 |
| maternally expressed 3 (non-protein coding) | NR_003531 | 2.44 | Down | 9.49E−06 | 2.5 | Down | 3.68E−04 |
| hypothetical LOC253039 | NR_024408 | 2.18 | Down | 8.79E−04 | 2.88 | Down | 2.45E−04 |
| hypothetical protein FLJ23867 | NR_026900 | 2.3 | Down | 3.97E−06 | 2.08 | Down | 2.39E−06 |
| non-protein coding RNA 114 | NR_027066 | 2.3 | Down | 9.80E−04 | 2.76 | Up | 1.62E−04 |
| hypothetical LOC100128096 | XR_038688 | 2.02 | Up | 9.16E−03 | 2.07 | Up | 4.12E−03 |

TABLE 9-continued

Gene list for 178 transcripts that were differentially-regulated in both terminal ileum and colon, exclusively in ASD$^{IC}$ samples.

| Gene Name | Gene Identifier | Terminal Ilium Ratio | Terminal Ilium Direction | Terminal Ilium adj. p-value | Colon Ratio | Colon Direction | Colon adj. p-value |
|---|---|---|---|---|---|---|---|
| similar to ankyrin repeat domain 20 family, member A2 | XR_042306 | 2.41 | Down | 2.78E−03 | 2.71 | Down | 1.41E−04 |

TABLE 10

Gene list for 41 transcripts that were differentially-regulated in a comparison of ASD$^{IC}$ samples with LNH + ileitis

| Gene Name | Gene Identifier | Ratio | Direction | adj. p-value |
|---|---|---|---|---|
| Solute carrier family 5 (iodide transporter), member 8 | NM_145913 | 4.4 | Up | 0.04067667 |
| Chemokine (C-X-C motif) ligand 3 | NM_002090 | 4.13 | Up | 0.03602154 |
| Aquaporin 9 | NM_020980 | 4.05 | Up | 0.03223694 |
| Hemoglobin, delta | NM_000519 | 3.78 | Up | 0.04621986 |
| S100 calcium binding protein A8 | NM_002964 | 3.78 | Up | 0.03223694 |
| Hemoglobin, beta | NM_000518 | 3.75 | Up | 0.04067667 |
| Transcribed locus, weakly similar to NP_000616.3 nitric oxide synthase 2A [Homo sapiens] | BC044655 | 3.72 | Up | 0.03223694 |
| Nitric oxide synthase 2, inducible | NM_000625 | 3.67 | Up | 0.03602154 |
| CKLF-like MARVEL transmembrane domain containing 2 | NM_144673 | 3.63 | Up | 0.03223694 |
| Hemoglobin, alpha 2 | NM_000517 | 3.44 | Up | 0.04067667 |
| Chemokine (C-X-C motif) ligand 11 | NM_005409 | 3.28 | Up | 0.03602154 |
| MTD | AF495759 | 3.09 | Down | 0.03223694 |
| Chemokine (C-X-C motif) ligand 2 | NM_002089 | 3.01 | Up | 0.04067667 |
| S100 calcium binding protein A12 | NM_005621 | 2.93 | Up | 0.0405102 |
| Chemokine (C-X-C motif) ligand 10 | NM_001565 | 2.84 | Up | 0.03447354 |
| Collagen, type II, alpha 1 | NM_001844 | 2.83 | Down | 0.03223694 |
| Apolipoprotein B mRNA editing enzyme, catalytic polypeptide-like 3A | NM_145699 | 2.81 | Up | 0.03223694 |
| S100 calcium binding protein A9 | NM_002965 | 2.77 | Up | 0.03223694 |
| Leukocyte-associated immunoglobulin-like receptor 2 | NM_002288 | 2.75 | Down | 0.03602154 |
| Leukocyte immunoglobulin-like receptor, subfamily B (with TM and ITIM domains), member 3 | NM_024318 | 2.39 | Up | 0.03602154 |
| Interleukin 8 receptor, beta | NM_001557 | 2.39 | Up | 0.04621986 |
| Chromosome 1 open reading frame 125 | NM_144696 | 2.34 | Up | 0.04067667 |
| Copine II | AK126138 | 2.27 | Up | 0.0405102 |
| Serpin peptidase inhibitor, clade A (alpha-1 antiproteinase, antitrypsin), member 3 | NM_001085 | 2.25 | Up | 0.04067667 |
| Similar to hCG1816473 | AL162045 | 2.23 | Up | 0.03602154 |
| Chemokine (C-X-C motif) ligand 9 | NM_002416 | 2.19 | Up | 0.04067667 |
| Dermatopontin | NM_001937 | 2.19 | Down | 0.03223694 |
| Amphiregulin | NM_001657 | 2.18 | Up | 0.04067667 |
| Hydroxysteroid (11-beta) dehydrogenase 1 | NM_181755 | 2.16 | Up | 0.03602154 |
| Chromosome 5 open reading frame 23 | NM_024563 | 2.11 | Down | 0.03602154 |
| Hypothetical protein LOC100131001 | XM_001723720 | 2.1 | Up | 0.03223694 |
| Formyl peptide receptor 1 | NM_002029 | 2.1 | Up | 0.03602154 |
| Matrix metallopeptidase 12 (macrophage elastase) | NM_002426 | 2.09 | Up | 0.03223694 |
| Similar to hCG1816027 | DB461660 | 2.08 | Up | 0.04067667 |
| LOC100287547 | XM_002343714 | 2.08 | Up | 0.04067667 |
| hCG_2011852 | NM_001146197 | 2.07 | Up | 0.04067667 |
| LOC283392 | NR_026837 | 2.07 | Down | 0.03447354 |
| ADAM metallopeptidase with thrombospondin type 1 motif, 4 | NM_005099 | 2.06 | Up | 0.03602154 |
| Fc fragment of IgG, high affinity Ib, receptor (CD64) | NM_001017986 | 2.05 | Up | 0.03602154 |
| IQ motif containing F6 | NM_001143833 | 2.04 | Up | 0.03223694 |
| NLR family, pyrin domain containing 2 | NM_017852 | 2.02 | Up | 0.04067667 |

Comparison of eQTL in ASD Associated Ileocolitis and Inflammatory Bowel Disease

Ileocolitis in GI Symptomatic ASD Children Shares eQTL with Known Inflammatory Bowel Disease Using gene expression data from that study, together with a second dataset derived from SNP analysis of DNA from the same individuals, expression quantitative trait loci (eQTL) were explored. The goals of this study were two-fold: (1) to see if there is a statistical association between genetic expression data and genetic polymorphisms in these IBD and IBD-like conditions and, (2) to determine if individual eQTL track with individual IBD subtypes.

Numerous eQTL associations were identified in both terminal illium and colon tissues. The number of children analyzed varied by tissue and disease state. There were 18 ASD$^{IC}$, 12 UC/CD with colon samples and 22 ASD$^{IC}$, 12 UC/CD with terminal ileum samples. Within the terminal ileum, 20 SNP-transcript combinations met the $p<1\times10E-9$ and fold change >1.5 threshold without evidence of heterogeneity. These 20 SNP-transcript combinations reside in 3 regions with the strongest association being between rs1127155 and NM_152559 ($P=3.1\times10E-12$). This probe corresponds to Williams Beuren syndrome chromosome region 27 on chr 7q11.23—a 1.5 MB deletion that includes this gene and 26 other genes is known to cause the neurodevelopmental disorder Williams Beuren Syndrome. Within the colon, 34 SNP-transcript combinations met the p<1×10E-9 and fold change >1.5 threshold. The top SNP-transcript combination was rs6460055 and NM_152559 (8.0×10E-11), the same transcript and region found in the terminal illium. The rs1127155 and NM_152559 combination was ranked $4^{th}$ (P=1.6×10E-9). Rs 1127155 and rs6460055 are in linkage disequilibrium ($r^2$=0.90). Additional analyses have the potential to identify eQTL that associate in specific tissue and that have contrasting expression levels between disease groups and controls.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating a gastrointestinal disorder selected from the group consisting of ileocolitis, ileitis, and colitis, in a human child, wherein said child has an autism spectrum disorder, the method comprising
   obtaining a biological sample from the colon or ileum of the child by ileocolonoscopy;
   immediately storing the biological sample in RNA stabilizer solution;
   freezing the biological sample within 48 hours;
   measuring RNA to determine a level of IL2RA in the biological sample,
   wherein an increase in the level of IL2RA relative to a reference indicates that the child has a gastrointestinal disorder, and
   administering a treatment for the gastrointestinal disorder to the child with the gastrointestinal disorder.

2. The method of claim 1, wherein measuring comprises PCR assays or microarray analysis.

SEQUENCE LISTING

```
<160> NUMBER OF SEQ ID NOS: 3

<210> SEQ ID NO 1
<211> LENGTH: 8769
<212> TYPE: DNA
<213> ORGANISM: Homo sapiens

<400> SEQUENCE: 1
atttagaggc ggcgccaggg cggccgcgga gaaacgtgac acaccagccc tctcggaggg      60
gtttcggacc gaagggaaga agctgcgccg tgtcgtccgt ctccctgcgc gccgcgggca     120
cttctcctgg gctctccccg aactctcccg cgacctctgc gcgccctcag gccgccttcc     180
ccgccctggg ctcgggacaa cttctggggt ggggtgcaaa gaaagtttgc ggctcctgcc     240
gccggcctct ccgcctcttg gcctaggagg ctcgccgccc gcgcccgctc gttcggcctt     300
gcccgggacc gcgtcctgcc ccgagaccgc caccatgaac aagctttaca tcggcaacct     360
caacgagagc gtgaccccg cggacttgga gaaagtgttt gcggagcaca agatctccta     420
cagcggccag ttcttggtca aatccggcta cgccttcgtg gactgcccgg acgagcactg     480
ggcgatgaag gccatcgaaa cttcctccgg gaaagtagaa ttacaaggaa aacgcttaga     540
gattgaacat tcggtgccca aaaacaaag gagccggaaa attcaaatcc gaaatattcc     600
accccagctc cgatgggaag tactggacag cctgctggct cagtatggta cagtagagaa     660
ctgtgagcaa gtgaacaccg agagtgagac ggcagtggtg aatgtcacct attccaaccg     720
ggagcagacc aggcaagcca tcatgaagct gaatggccac cagttggaga accatgccct     780
gaaggtctcc tacatccccg atgagcagat agcacaggga cctgagaatg ggcgccgagg     840
gggctttggc tctcggggtc agccccgcca gggctcacct gtggcagcgg gggccccagc     900
caagcagcag caagtggaca tccccttcg gctcctggtg cccacccagt atgtgggtgc     960
cattattggc aaggaggggg ccaccatccg caacatcaca aaacagaccc agtccaagat    1020
agacgtgcat aggaaggaga acgcaggtgc agctgaaaaa gccatcagtg tgcactccac    1080
ccctgagggc tgctcctccg cttgtaagat gatcttggag attatgcata aagaggctaa    1140
ggacaccaaa acggctgacg aggttcccct gaagatcctg gcccataata actttgtagg    1200
gcgtctcatt ggcaaggaag gacggaacct gaagaaggta gagcaagata ccgagacaaa    1260
aatcaccatc tcctcgttgc aagaccttac cctttacaac cctgagagga ccatcactgt    1320 gaaggggcc atcgagaatt gttgcagggc cgagcaggaa ataatgaaga agttcgggga    1380
ggcctatgag aatgatgtgg ctgccatgag cctgcagtct cacctgatcc ctggcctgaa    1440
cctggctgct gtaggtcttt tcccagcttc atccagcgca gtcccgccgc ctcccagcag    1500
cgttactggg gctgctccct atagctcctt tatgcaggct cccgagcagg agatggtgca    1560 ggtgttatc cccgcccagg cagtgggcgc catcatcggc aagaaggggc agcacatcaa    1620
acagctctcc ggtttgcca gcgcctccat caagattgca ccacccgaaa cacctgactc    1680
caaagttcgt atggttatca tcactggacc gccagaggcc aattcaagg ctcagggaag    1740
```

```
aatctatggc aaactcaagg aggagaactt ctttggtccc aaggaggaag tgaagctgga    1800
gacccacata cgtgtgccag catcagcagc tggccgggtc attggcaaag gtggaaaaac    1860
ggtgaacgag ttgcagaatt tgacggcagc tgaggtggta gtaccaagag accagacccc    1920
tgatgagaac gaccaggtca tcgtgaaaat catcggacat ttctatgcca gtcagatggc    1980
tcaacggaag atccgagaca tcctggccca ggttaagcag cagcatcaga agggacagag    2040
taaccaggcc caggcacgga ggaagtgacc agcccctccc tgtcccttcg agtccaggac    2100
aacaacgggc agaaatcgag agtgtgctct ccccggcagg cctgagaatg agtgggaatc    2160
cgggacacct gggccgggct gtagatcagg tttgcccact tgattgagaa agatgttcca    2220
gtgaggaacc ctgatctctc agccccaaac acccacccaa ttggcccaac actgtctgcc    2280
cctcggggtg tcagaaattc tagcgcaagg cacttttaaa cgtggattgt ttaaagaagc    2340
tctccaggcc ccaccaagag ggtggatcac acctcagtgg gaagaaaaat aaaatttcct    2400
tcaggtttta aaaacatgca gagaggtgtt ttaatcagcc ttaaaggatg gttcatttct    2460
tgaccttaat gttttttccaa tcttcttccc cctacttggg taattgatta aaatacctcc    2520
atttacggcc tctttctata tttacactaa tttttttatc tttattgcta ccagaaaaaa    2580
atgcgaacga atgcattgct ttgcttacag tattgactca agggaaaaga actgtcagta    2640
tctgtagatt aattccaatc actccctaac caataggtac aatacggaat gaagaagagg    2700 ggaaatggg gagaaagatg gttaaaatac ataataatcc acgtttaaaa ggagcgcact    2760
tgtggctgat ctatgccaga tcaccatctt caaattggca caactgaaat ttccccactc    2820
tgttggggct tccccaccac attcatgtcc ctctcccgtg taggtttcac attatgtcca    2880
ggtgcacata ggtggtattg aatgctcagc agggtagggg ctgaccactg tccctgattc    2940
ccatcgttct caggcggatt ttatatttt ttaaagtcta ttttaatgat tggatatgag    3000
cactgggaag gggacgctaa ctccccttga taaagtctcg gttccatgga ggacttgagt    3060
ggccccaaag gctgccacgg tgccctcacc ccagcccatg tgctcccata agggctggtt    3120
cctagaggca ggggttgtgg ggcactccca gccacggcac tgttaccttg gtggtgggac    3180
ttggaaccca accctgagct cccgataaag ctaaagtcca tcatctggca aattcagtaa    3240
attggagagt acttgcttct gtttgtatct gagaggaatt tttaactgac ggcttctgtc    3300
tccatgaatc attatcagca tgatgaaagg tgtgtctaaa aaacaattca gaataccagc    3360
agcattgtac agcaagggt aaataagctt aatttattaa tttaccaggc ttaattaaga    3420
tcccatggag tgtttagccc ttgtgggaga cagaagccat cagttaaatg aggttaggcc    3480
tctcctccta atatactgat tgacaatgca tattagccag gtaatgcact ttagctaccc    3540
tggacaatgc tatcaagtgt gctgggaagg gaggaaggcc tctctacata tggaaaagcc    3600
catgcgtgga gttcccctcc tttcaacatt gcaacaacag taacaacaag acaaccgcaa    3660
catgtgggcg tagtcaggca atgctgtgtg cgaagtaaac tacctcaagg tatgaagtta    3720
cctcagcaat tattttcctt tttgttcccc ccaacccat taaaaaaatt tttttttgat    3780
ttttgttttt ttgcagcttg ctgatatttt atataaaaaa gaaaagcaaa gcaaagagaa    3840
agctgatagt cttgaatatt ttatttttt aatgaaaaga aaaacaaga aagttatgtt    3900 tcataatttc ttacaacatg agccagtaac cctttaggaa ctctctatgg agaacaggcc    3960
tggtgggaaa ggctttgggg gctgcccct taggaggagg ctagtgctaa gagggaaggc    4020
ccaggtttga gagagcccag aggggcagag cccagagcct tgtttggccc tgatctctga    4080
```

-continued

```
cttctagagc cccagctgct ggcggctgct ggaatatcct acctgatagg attaaaaggc    4140
ctagtggagc tgggggctct cagtggttaa acaatgccca acaaccaacc agctggccct    4200
tggtctcctc tctttcctcc tttggttaaa gagcatctca gccagctttt cccaccagtg    4260
gtgctgttga gatattttaa aatattgcct ccgttttatc gaggagagaa ataataacta    4320 aaaatatac cctttaaaaa aacctatatt tctctgtcta aaaatatggg agctgagatt    4380
ccgttcgtgg aaaaaagaca aggccaccct ctcgccctca gagaggtcca cctggtttgt    4440
cattgcaatg cttttcattt ttttttttg ttattgtttc atttcagttc cgtcttgcta    4500
ttcttcctaa tctatatcca tagatctaag gggcaaacag atactagtta actgccccca    4560
cctctgtctc cctgtcttct ttagatcggt ctgattgatt ttaaaagtgg acccaaactt    4620
agggaattct tgatttaggg tggctggtgg caaggagggg cagggatat ggggacgtga    4680 ctgggacagg ttcctgcctt atcatttct ccctaggaca ttcccttgta gccccagaa     4740 ttgtctggcc caaattgaat agaagcagaa aaacatttag ggataacatc aggccagtag    4800
aattaagcct ctccacctgt cccaaccata aaaagggtct cccagctttc catctctggc    4860
tctatatgct ttatcccaaa acaaagcaga taacgttcag acgtcggcca tttagtaatt    4920
taaagcgaat ttccagcagc aagcatgctt tgatatctgg ttcagactat catcaggaag    4980
aaaaaaaaat cccacagtac ctgaaatgtg attgttgcag tgttcagttt ccttggggc    5040 ctgctccctt cacaccttga gcccaagtcc ttttccgttg gctgattcag ctcccagaag    5100
agacgaggaa gtgtgtggca agggactgga aaacttcact tgcttggatt aggcaaggct    5160
ccactcattg ttgatatttg cccagcagga aaatcatgta agttataccca cagaaagca    5220 aaaggagcat ggtttggtgg ttaaggttta gtgggatgaa ggacctgtct tggtgggccg    5280
ggccctcttg tgccccgtag gctaggtctt agggcaactc cttgccctcc tgctcagcac    5340
ctccatttcc ccatccttgg tgagataaca agctatcgcg aaaagcactt gggagatttg    5400
gatgatttga gaagagtgac ttaaaaaaa tgcttctgtg ctctaagata tatatgtgtg    5460
tgtgtgtgct acatatatat ttttaagaaa ggaccatctc tttaggatat atttttaaat    5520
tctttgaaac acataaccaa aatggttga ttcactgact gactttgaag ctgcatctgc     5580
cagttacacc ccaaatggct ttaatcccct ctcgggtctg gttgcttttt gcagtttggg    5640
ttgtggactc agctcctgtg aggggtctgg ttaggagaga gccatttttta aggacaggga    5700 gttttatagc ccttttctac tttcctcccc tcctcccagt cctatcaat cttttttcct     5760 ttttcctgac cccctccttc tggaggcagt tgggagctat ccttgtttat gcctcactat    5820
tggcagaaaa gaccccattt aaaacccaga gaacactgga gggggatgct ctagttggtt    5880
ctgtgtccat tttcctctgt gccaaagaca gacagacaga ggctgagaga ggctgttcct    5940
gaatcaaagc aatagccagc tttcgacaca tacctggctg tctgaggagg aaggcctcct    6000
ggaaactggg agctaaggc gaggcccttc ccttcagagg ctcctggggg attagggtgt     6060
ggtgtttgcc aagccaaggg gtagggagcc gagaaattgg tctgtcggct cctggttgca    6120
ctttggggaa ggagaggaag tttggggctc caggtagctc cctgttgtgg gactgctctg    6180
tcccctgccc ctactgcaga gatagcactg ccgagttccc ttcaggcctg gcagacgggc    6240
agtgaggagg ggcctcagtt agctctcaag ggtgccttcc cctcctccca acccagacat    6300
accctctgcc aaactgggaa ccagcagtgc tagtaactac ctcacagagc cccagagggc    6360
ctgcttgagc cttcttgctc cacaggagaa gctggtgcct ctaggcaacc ccttcctccc    6420
acctctcatc aggggtgggg gttctccttt cttccccctg aagtgtttat ggggagatcc    6480
```

```
tagtggcttt gccattcaaa ccactcgact gtttgcctgt ttcttgaaaa ccagtagaag    6540
ggaaacagca cagcctgtca cagtaattgc aggaagattg aagaaaaatc ctcatcaatg    6600 ccagggaca taaaagccat ttcccttcca atactcgac aatttagatg cagaacattt      6660
ctctgtattc agacttagag taacaccagc tgaaaactgc agtttctttc ctttggatac    6720
ataaggcttc tctatcgggg tacgggacag ggaggaggcc tcatgtctga aggggattt    6780 aggggcgaga gccccagccc tgaccctcgg tcctgtgcac cgctttgggg cacagtctga    6840
tggcgccttt gctggcgcct tagtatggtt gactccggat ggacaaaaga aaaaaatt     6900 ttttcttga atgaaatagc aggaagctcc tcgggagcat gtgttttgat taaccgcagg    6960
tgatggatgc tacgagtata atggattaa ctacctcaat ccttacagta agattggaac    7020
taagggcagg gactcatgca taagggtatg aatcccagcc aggacaagtg agttgaggct    7080
tgtgccacaa aaggtttgtc cttggggaac aggcaggcct gccaggatcc cccccatatc    7140
gattgggctg ggagggctgg ccatgaggtc cccactttct gctttccttg cccatgtgtc    7200 accccttgg cctccagctt gtccctctct cactttctat agctttgttg gaccagatgg     7260
tgaggaaagg aatggcctct tcccttctag aggggggctgg ctggagtgag acctggggct    7320
tggcctggaa cccaccacac agccccaaag tcaggaagcc tggggaaacc agagctgaga    7380
cctcttcaac agggtttctt tgagatccta cacctccatt gggcccttttt tcagtcttca    7440 atgggggccc agttggctct agaaggagaa gaggtgaagc aggatccttt gccctgggg     7500 agtctgaggg cgcggtcctt ggactcattc aggccgtctt tgtagttggg ggagttccac    7560
tgggcgatcc cagcccctcc ccacccaccc tctaatggac ctcctcatag aagcccatt     7620 tcacttttgt tttatctacc tcttagcaaa acaatagata aattaggtag tggcagctcc    7680
acttgcttag gttaggggg gaaaaagatt tcttttttcca aaggaaaaaa atattacctt    7740
gagaatactt tccaaaaaat aaaattaaaa aaaaaaaaac caaaaaaaaa attttttt    7800 taaagggag acatttttcca gtgaccactg gattgtttta attttcccaag cttttttttc    7860 ccccataaat aagtttcact cttttggcgat tttcttcact tgtttaagat aacgtgctag    7920
ctattccaac aggtaacagc tttcacagtc tgcccctggc ctgtctcacc ccatccccca    7980
ccctattcct gccagtgagt ccttcctgtg cttctctccc ttctccctc ccagccagct     8040 gacttcagtc accccctgtcc cccctcccct gccaataagc tccccagga ataaaggctt    8100 tgttttgggg atgcttaaat cttgactggc acttcccggc tgtgggggct ggggagccac    8160
ttgtaacatt tctgtgcaga ttttatgtta gccactgcta tgtaaaagca cgttcaaaat    8220
gaatttcagc agattatgtg ttaccataat gaataaacgt cctctatcac catttggagt    8280
ctcccttttc tccaggatct tgatcctggt ccccaaaacc agagtgaatc aaaagagctt    8340 cctccctga ggcaaagtgg atttgtaagc agttctgaaa catcacttac tcagaagagg     8400
gaacgatgta ttttgatgag tgcaaattgg aagagctgg aggcctactg cttgggacag    8460 ttttttttt tttttttt ttaaatatga gtgctagctt attctgtaat tgcggcaact       8520
ttgaaaattg tatttactg gaaatctgcc agccatcacc accgatttt gattgtatcc      8580 ttcctcccat cctttaatct gttcattgct ttggggggag tggggcagct ggctcacacg    8640
ttggagtttg ttctttgatg gatgaacgaa cactccagtt ttctttcccg tgaaggttgt    8700
ttcagccaca aaccacttca ttttgctgtt tcaatttcaa aataaaagga aacttatatt    8760
gaaagacaa                                                            8769
```

<210> SEQ ID NO 2
<211> LENGTH: 3216
<212> TYPE: DNA
<213> ORGANISM: Homo sapiens

<400> SEQUENCE: 2

| | | | | | | |
|---|---|---|---|---|---|---|
| ggcagtttcc | tggctgaaca | cgccagccca | atacttaaag | agagcaactc | ctgactccga | 60 |
| tagagactgg | atggacccac | aagggtgaca | gcccaggcgg | accgatcttc | ccatcccaca | 120 |
| tcctccggcg | cgatgccaaa | agaggctga | cggcaactgg | gccttctgca | gagaaagacc | 180 |
| tccgcttcac | tgcccggct | ggtcccaagg | gtcaggaaga | tggattcata | cctgctgatg | 240 |
| tggggactgc | tcacgttcat | catggtgcct | ggctgccagg | cagagctctg | tgacgatgac | 300 |
| ccgccagaga | tcccacacgc | cacattcaaa | gccatggcct | acaaggaagg | aaccatgttg | 360 |
| aactgtgaat | gcaagagagg | tttccgcaga | ataaaaagcg | ggtcactcta | tatgctctgt | 420 |
| acaggaaact | ctagccactc | gtcctgggac | aaccaatgtc | aatgcacaag | ctctgccact | 480 |
| cggaacacaa | cgaaacaagt | gacacctcaa | cctgaagaac | agaaagaaag | gaaaaccaca | 540 |
| gaaatgcaaa | gtccaatgca | gccagtggac | caagcgagcc | ttccaggtca | ctgcagggaa | 600 |
| cctccaccat | gggaaaatga | agccacagag | agaatttatc | atttcgtggt | ggggcagatg | 660 |
| gtttattatc | agtgcgtcca | gggatacagg | gctctacaca | gaggtcctgc | tgagagcgtc | 720 |
| tgcaaaatga | cccacgggaa | gacaaggtgg | acccagcccc | agctcatatg | cacaggtgaa | 780 |
| atggagacca | gtcagtttcc | aggtgaagag | aagcctcagg | caagcccga | aggccgtcct | 840 |
| gagagtgaga | cttcctgcct | cgtcacaaca | acagattttc | aaatacagac | agaaatggct | 900 |
| gcaaccatgg | agacgtccat | atttacaaca | gagtaccagg | tagcagtggc | cggctgtgtt | 960 |
| ttcctgctga | tcagcgtcct | cctcctgagt | gggctcacct | ggcagcggag | acagaggaag | 1020 |
| agtagaagaa | caatctagaa | aaccaaaaga | acaagaattt | cttggtaaga | agccgggaac | 1080 |
| agacaacaga | agtcatgaag | cccaagtgaa | atcaaaggtg | ctaaatggtc | gcccaggaga | 1140 |
| catccgttgt | gcttgcctgc | gttttggaag | ctctgaagtc | acatcacagg | acacggggca | 1200 |
| gtggcaacct | tgtctctatg | ccagctcagt | cccatcagag | agcgagcgct | acccacttct | 1260 |
| aaatagcaat | ttcgccgttg | aagaggaagg | gcaaaaccac | tagaactctc | atcttatt | 1320 |
| tcatgtatat | gtgttcatta | aagcatgaat | ggtatggaac | tctctccacc | ctatatgtag | 1380 |
| tataaagaaa | agtaggttta | cattcatctc | attccaactt | cccagttcag | gagtcccaag | 1440 |
| gaaagcccca | gcactaacgt | aaatacacaa | cacacacact | ctaccctata | caactggaca | 1500 |
| ttgtctgcgt | ggttcctttc | tcagccgctt | ctgactgctg | attctcccgt | tcacgttgcc | 1560 |
| taataaacat | ccttcaagaa | ctctgggctg | ctacccagaa | atcattttac | ccttggctca | 1620 |
| atcctctaag | ctaaccccct | tctactgagc | cttcagtctt | gaatttctaa | aaaacagagg | 1680 |
| ccatggcaga | ataatctttg | ggtaacttca | aaacggggca | gccaaaccca | tgaggcaatg | 1740 |
| tcaggaacag | aaggatgaat | gaggtcccag | gcagagaatc | atacttagca | aagttttacc | 1800 |
| tgtgcgttac | taattggcct | ctttaagagt | tagtttcttt | gggattgcta | tgaatgatac | 1860 |
| cctgaatttg | gcctgcacta | atttgatgtt | tacaggtgga | cacacaaggt | gcaaatcaat | 1920 |
| gcgtacgttt | cctgagaagt | gtctaaaaac | accaaaaagg | gatccgtaca | ttcaatgttt | 1980 |
| atgcaaggaa | ggaaagaaag | aaggaagtga | agagggagaa | gggatggagg | tcacactggt | 2040 |
| agaacgtaac | cacggaaaag | agcgcatcag | gcctggcacg | gtggctcagg | cctataaccc | 2100 |
| cagctcccta | ggagaccaag | gcgggagcat | ctcttgaggc | caggagtttg | agaccagcct | 2160 |

```
gggcagcata gcaagacaca tccctacaaa aaattagaaa ttggctggat gtggtggcat      2220
acgcctgtag tcctagccac tcaggaggct gaggcaggag gattgcttga gcccaggagt      2280
tcgaggctgc agtcagtcat gatggcacca ctgcactcca gcctgggcaa cagagcaaga      2340
tcctgtcttt aaggaaaaaa agacaagatg agcataccag cagtccttga acattatcaa      2400
aaagttcagc atattagaat caccgggagg ccttgttaaa agagttcgct gggcccatct      2460
tcagagtctc tgagttgttg gtctggaata gagccaaatg ttttgtgtgt ctaacaattc      2520
ccaggtgctg ttgctgctgc tactattcca ggaacacact ttgagaacca ttgtgttatt      2580
gctctgcacg cccacccact ctcaactccc acgaaaaaaa tcaacttcca gagctaagat      2640
ttcggtggaa gtcctggttc catatctggt gcaagatctc ccctcacgaa tcagttgagt      2700
caacattcta gctcaacaac atcacacgat taacattaac gaaaattatt catttgggaa      2760
actatcagcc agttttcact tctgaagggg caggagagtg ttatgagaaa tcacggcagt      2820
tttcagcagg gtccagattc agattaaata actattttct gtcatttctg tgaccaacca      2880
catacaaaca gactcatctg tgcactctcc ccctccccct tcaggtatat gttttctgag      2940
taaagttgaa aagaatctca gaccagaaaa tatagatata tatttaaatc ttacttgagt      3000
agaactgatt acgacttttg ggtgttgagg ggtctataag atcaaaactt ttccatgata      3060
atactaagat gttatcgacc atttatctgt ccttctctca aaagtgtatg gtggaatttt      3120
ccagaagcta tgtgatacgt gatgatgtca tcactctgct gttaacatat aataaattta      3180
ttgctattgt ttataaaaga ataaatgata tttttt                                3216

<210> SEQ ID NO 3
<211> LENGTH: 1048
<212> TYPE: DNA
<213> ORGANISM: Homo sapiens

<400> SEQUENCE: 3
aaggcggggg cggggggcggg gcggcggccg tgggtccctg ccggccggcg gcgggcgcag        60
acagcggcgg gcgcaggacg tgcactatgg ctcggggctc gctgcgccgg ttgctgcggc       120
tcctcgtgct ggggctctgg ctggcgttgc tgcgctccgt ggccggggag caagcgccag       180
gcaccgcccc ctgctcccgc ggcagctcct ggagcgcgga cctggacaag tgcatggact       240
gcgcgtcttg cagggcgcga ccgcacagcg acttctgcct gggctgcgct gcagcacctc       300
ctgccccctt ccggctgctt tggcccatcc ttggggcgc tctgagcctg accttcgtgc       360
tggggctgct ttctggctttt ttggtctgga gacgatgccg caggagagag aagttcacca       420
cccccataga ggagaccggc ggagagggct gcccagctgt ggcgctgatc cagtgacaat       480 gtgcccctg ccagccgggg ctcgcccact catcattcat tcatccattc tagagccagt       540
ctctgcctcc cagacgcggc gggagccaag ctcctccaac cacaaggggg gtgggggggcg       600 gtgaatcacc tctgaggcct gggcccaggg ttcagggaa ccttccaagg tgtctggttg       660
ccctgcctct ggctccagaa cagaaaggga gcctcacgct ggctcacaca aaacagctga       720
cactgactaa ggaactgcag catttgcaca ggggagggg gtgccctcct tcctagaggc       780
cctgggggcc aggctgactt gggggcagga cttgacacta ggccccactc actcagatgt       840
cctgaaattc caccacgggg gtcaccctgg ggggttaggg acctatttt aacactaggg       900 ggctggccca ctaggagggc tggccctaag atacagaccc ccccaactcc ccaaagcggg       960
```

```
gaggagatat ttattttggg gagagtttgg aggggaggga gaatttatta ataaaagaat    1020
ctttaacttt aaaaaaaaaa aaaaaaa                                        1048
```